(12) United States Patent
Blackburn et al.

(10) Patent No.: US 12,378,198 B2
(45) Date of Patent: *Aug. 5, 2025

(54) CRYSTALLINE L-ARGININE SALT OF (R)-2-(7-(4-CYCLOPENTYL-3-(TRIFLUOROMETHYL)BENZYLOXY)-1,2,3,4-TETRAHYDROCYCLO-PENTA[B]INDOL-3-YL)ACETIC ACID(COMPOUND1) FOR USE IN SIPI RECEPTOR-ASSOCIATED DISORDERS

(71) Applicant: Arena Pharmaceuticals, Inc., New York, NY (US)

(72) Inventors: Anthony C. Blackburn, San Diego, CA (US); Ryan O. Castro, San Diego, CA (US); Mark Allen Hadd, San Diego, CA (US); You-An Ma, Poway, CA (US); Antonio Garrido Montalban, San Diego, CA (US); Jaimie Karyn Rueter, San Diego, CA (US); Lee Alani Selvey, Longview, WA (US); Sagar Raj Shakya, San Diego, CA (US); Marlon Carlos, Chula Vista, CA (US)

(73) Assignee: Arena Pharmaceuticals, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/542,913

(22) Filed: Dec. 18, 2023

(65) Prior Publication Data

US 2024/0140911 A1 May 2, 2024

Related U.S. Application Data

(63) Continuation of application No. 17/375,063, filed on Jul. 14, 2021, now Pat. No. 11,884,626, which is a continuation of application No. 16/862,681, filed on Apr. 30, 2020, now Pat. No. 11,091,435, which is a continuation of application No. 16/379,265, filed on Apr. 9, 2019, now Pat. No. 10,676,435, which is a continuation of application No. 15/738,175, filed as application No. PCT/US2016/038506 on Jun. 21, 2016, now Pat. No. 10,301,262.

(60) Provisional application No. 62/207,531, filed on Aug. 20, 2015, provisional application No. 62/182,841, filed on Jun. 22, 2015.

(51) Int. Cl.
C07D 209/70 (2006.01)
C07C 279/12 (2006.01)
C07D 209/94 (2006.01)

(52) U.S. Cl.
CPC .......... *C07D 209/94* (2013.01); *C07C 279/12* (2013.01); *C07B 2200/13* (2013.01)

(58) Field of Classification Search
CPC ........................... C07D 209/70; C07D 209/94
See application file for complete search history.

(56) References Cited

U.S. PATENT DOCUMENTS

| | | | | |
|---|---|---|---|---|
| 10,301,262 B2 * | 5/2019 | Blackburn | .............. | A61P 29/00 |
| 10,676,435 B2 * | 6/2020 | Blackburn | ................ | A61P 1/00 |
| 11,091,435 B2 * | 8/2021 | Blackburn | .............. | A61P 29/00 |
| 11,884,626 B2 * | 1/2024 | Blackburn | ................ | A61P 1/16 |

* cited by examiner

*Primary Examiner* — Brenda L Coleman
(74) *Attorney, Agent, or Firm* — Feng Shao

(57) ABSTRACT

The present invention relates to, inter alia, a novel crystalline free-plate habit or morphology, processes for preparing the crystalline free-plate habit, and uses of the crystalline free-plate habit of the L-arginine salt of (R)-2-(7-(4-cyclopentyl-3-(trifluoromethyl)benzyloxy)-1,2,3,4-tetrahydrocyclo-penta[b]indol-3-yl)acetic acid (Compound 1) in the treatment of $S1P_1$ receptor-associated disorders, for example, diseases and disorders mediated by lymphocytes, transplant rejection, autoimmune diseases and disorders, inflammatory diseases and disorders (e.g., acute and chronic inflammatory conditions), cancer, and conditions characterized by an underlying defect in the vascular integrity or that are associated with angiogenesis such as may be pathologic (e.g., as may occur in inflammation, tumor development, and atherosclerosis).

40 Claims, 24 Drawing Sheets

Scanning Electron Micrograph of Spherulites (See Example 1)

Polarized Light Micrograph of Spherulites (See Example 1)

Scanning Electron Micrograph of the Crystal Morphology from Example 2 (Lot J2)

Scanning Electron Micrograph of the Crystal
Morphology from Example 2 (Lot J1)

Polarized Light Micrograph of the Crystal
Plate Morphology from Example 3

Polarized Light Micrograph of the Crystal Plate Morphology from Example 3

Polarized Light Micrograph of the Crystal Plate Morphology (See Example 4)

Polarized Light Micrograph of the Crystal
Plate Morphology (See Example 4)

PLM for the Crystalline Material from Example 7,
Method 1 Step B (WO2011/094008)

Purification Flow Chart (See Example 8)

CRYSTALLINE L-ARGININE SALT OF (R)-2-(7-(4-CYCLOPENTYL-3-(TRIFLUOROMETHYL)BENZYLOXY)-1,2,3,4-TETRAHYDROCYCLO-PENTA[B]INDOL-3-YL)ACETIC ACID(COMPOUND1) FOR USE IN S1P1 RECEPTOR-ASSOCIATED DISORDERS

This application is a continuation of U.S. application Ser. No. 17/375,063, filed Jul. 14, 2021; which in turn is a continuation of U.S. application Ser. No. 16/862,681, filed Apr. 30, 2020, now U.S. Pat. No. 11,091,435, granted on Aug. 17, 2021; which in turn is a continuation of U.S. application Ser. No. 16/379,265, now U.S. Pat. No. 10,676,435, granted on Jun. 9, 2020; which in turn is a continuation of U.S. application Ser. No. 15/738,175 filed Dec. 20, 2017, now U.S. Pat. No. 10,301,262, granted on Apr. 28, 2019; which in turn is a national phase filing under 35 U.S.C. § 371 of international patent application number PCT/US2016/038506, filed Jun. 21, 2016; which in turn claims the benefit of priority to U.S. Provisional Patent Application Ser. Nos. 62/182,841, filed on Jun. 22, 2015 and 62/207,531, filed Aug. 20, 2015, the disclosure of each of the foregoing applications is hereby incorporated by reference in its entirety.

FIELD OF THE INVENTION

The present invention relates to, inter alia, a novel crystalline free-plate habit or morphology, processes for preparing the crystalline free-plate habit, and uses of the crystalline free-plate habit of the L-arginine salt of (R)-2-(7-(4-cyclopentyl-3-(trifluoromethyl)benzyloxy)-1,2,3,4-tetrahydrocyclo-penta[b]indol-3-yl)acetic acid (Compound 1) in the treatment of $S1P_1$ receptor-associated disorders, for example, diseases and disorders mediated by lymphocytes, transplant rejection, autoimmune diseases and disorders, inflammatory diseases and disorders (e.g., acute and chronic inflammatory conditions), cancer, and conditions characterized by an underlying defect in the vascular integrity or that are associated with pathological angiogenesis (e.g., as may occur in inflammation, tumor development, and atherosclerosis).

BACKGROUND OF THE INVENTION

The sphingosine-1-phosphate (S1P) receptors 1-5 constitute a family of G protein-coupled receptors with a seven-transmembrane domain. These receptors, referred to as $S1P_1$ to $S1P_5$ (formerly termed endothelial differentiation gene (EDG) receptor-1, -5, -3, -6, and -8, respectively; Chun et. al., Pharmacological Reviews, 54:265-269, 2002), are activated via binding by sphingosine-1-phosphate, which is produced by the sphingosine kinase-catalyzed phosphorylation of sphingosine. $S1P_1$, $S1P_4$, and $S1P_5$ receptors activate Gi but not Gq, whereas $S1P_2$ and $S1P_3$ receptors activate both Gi and Gq. The $S1P_3$ receptor, but not the $S1P_1$ receptor, responds to an agonist with an increase in intracellular calcium.

The compound (R)-2-(7-(4-cyclopentyl-3-(trifluoromethyl)benzyloxy)-1,2,3,4-tetrahydrocyclopenta[b]indol-3-yl)acetic acid (Compound 1) is a potent ($EC_{50}$ cAMP, 0.093 nM (human)) and selective ($EC_{50}$ β-arrestin, 6.10 nM ($S1P_1$), >10,000 nM ($S1P_2$), >10,000 nM, ($S1P_3$), 147 nM ($S1P_4$), and 24.4 nM ($S1P_5$)), orally available investigational drug candidate for the $S1P_1$ receptor.

In preclinical studies, Compound 1 showed calculated lymphocyte lowering $IC_{50}$ values in four different species: 0.101 μM (mouse), 0.051 μM (rat), 0.058 μM (dog), and 0.098 μM (monkey). Notably, the calculated lymphocyte lowering $IC_{50}$ values reflect total plasma concentration wherein Compound 1 is highly protein bound (97.8% human, 98.0% rat). Compound 1 was shown to be efficacious in the murine experimental autoimmune encephalomyelitis (EAE) model that mimics multiple sclerosis. Prophylactically, Compound 1 prevented the onset and severity of disease relative to vehicle up to day 25, at which time dosing was discontinued. All treatment arms went on to develop severe disease. Therapeutic administration of Compound 1 was also examined. Treatment began at day 18, by which time all animals had developed severe disease. Compound 1 was administered from day 18 to day 37 and showed to reverse the disease relative to vehicle and was similar to the efficacy observed with fingolimod (i.e., GILENYA® was approved in September 2010 for the treatment of patients with relapsing forms of multiple sclerosis). Similarly, Compound 1 was efficacious in a collagen induced arthritis (CIA) model. Prophylactic oral administration in female Lewis rats resulted in a significant reduction in ankle diameters on day 17 following a daily oral dose and was similar to that observed in rats treated with fingolimod or methotrexate. Improvement in histological parameters in the knees and ankles of CIA rats was also observed, suggesting that inhibiting lymphocyte entry into arthritic joints with Compound 1 treatment suppresses CIA in rodents. Additional details can be found in the following, PCT application, serial number PCT/US2009/004265, filed 22 Jul. 2009 (International Publication Number WO2010/011316); PCT application, serial number PCT/US2011/000153, filed 27 Jan. 2011 (International Publication Number WO2011/094008); and Buzard: D. J., et. al., *ACS Med. Chem. Lett.* 2014, 5, 1313-1317; each hereby incorporated by reference in its entirety.

The L-arginine salt of Compound 1 was selected for clinical evaluation. A randomized, double-blind, placebo-controlled Phase 1b clinical trial was conducted to evaluate the safety, tolerability, pharmacodynamics, and pharmacokinetics of multiple-ascending doses of the L-arginine salt of Compound 1 in five different dosing cohorts. A total of 50 healthy volunteers received the L-arginine salt of Compound 1 and 10 healthy volunteers received placebo for 21 days. In the Phase 1b clinical trial, the administration of the L-arginine salt of Compound 1 demonstrated a dose-dependent effect on lymphocyte count lowering in blood, with a mean decrease from baseline of up to 69%. Lymphocyte counts, on average, recovered to baseline within one week of the conclusion of dosing.

In view of the growing demand for compounds useful in the treatment of $S1P_1$ receptor-associated disorders, the L-arginine salt of (R)-2-(7-(4-cyclopentyl-3-(trifluoromethyl)benzyloxy)-1,2,3,4-tetrahydrocyclopenta[b]indol-3-yl)acetic acid (Compound 1) has emerged as an important new compound.

Accordingly, new and efficient methods are needed for the preparation of the L-arginine salt of Compound 1 and crystalline morphologies related thereto. Several improvements have now been discovered in this regard. These improvements are described herein.

Citation of any reference throughout this application is not to be construed as an admission that such reference is prior art to the present application.

SUMMARY OF THE INVENTION

The present invention relates to, inter alia, a novel crystalline free-plate habit or morphology, processes for preparing the crystalline free-plate habit, and uses of the crystalline free-plate habit of the L-arginine salt of (R)-2-(7-(4-cyclopentyl-3-(trifluoromethyl)benzyloxy)-1,2,3,4-tetrahydrocyclopenta[b]indol-3-yl)acetic acid (Compound 1) in the treatment of $S1P_1$ receptor-associated disorders, such as, those described herein.

Compound 1

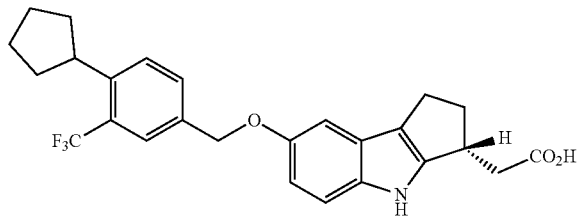

Discovery of the novel crystalline plate habit, referred to as "free-plate habit" herein, led to certain advantageous properties, such as, improved in-process filtrations, formulation stability and/or stability to degradation, higher degree of crystallinity, and lower degree of hygroscopicity, see Example 8 for details.

Certain processes for the preparation of the L-arginine salt of (R)-2-(7-(4-cyclopentyl-3-(trifluoromethyl)benzyloxy)-1,2,3,4-tetrahydrocyclopenta[b]indol-3-yl)acetic acid have been previously described; see WO2010/011316 and WO2011/094008.

One aspect of the present invention relates to methods for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid, the method comprising the steps of:
a) hydrolyzing a compound of Formula (IIa):

(IIa)

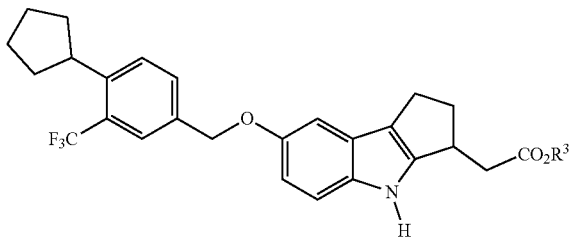

wherein $R^3$ is $C_1$-$C_6$ alkyl; in the presence of a hydrolyzing mixture comprising a lipase and a hydrolyzing-step solvent to form (R)-2-(7-(4-cyclopentyl-3-(trifluoromethyl)benzyloxy)-1,2,3,4-tetrahydrocyclopenta[b]indol-3-yl)acetic acid;
b) adding L-arginine to a salt-forming mixture comprising (R)-2-(7-(4-cyclopentyl-3-(trifluoromethyl)benzyloxy)-1,2,3,4-tetrahydrocyclopenta[b]indol-3-yl)acetic acid, a water-miscible anti-solvent, and $H_2O$ to form a first mixture comprising L-arginine salt of (R)-2-(7-(4-cyclopentyl-3-(trifluoromethyl)benzyloxy)-1,2,3,4-tetrahydrocyclopenta[b]indol-3-yl)acetic acid;
c) heating the first mixture to a first heating temperature;
d) adding a first additional amount of the water-miscible anti-solvent to the first mixture to form a suspension; and
e) cooling the suspension to form the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid.

One aspect of the present invention relates to methods for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid, said method comprising the steps of:
a) hydrolyzing a compound of Formula (IIa):

(IIa)

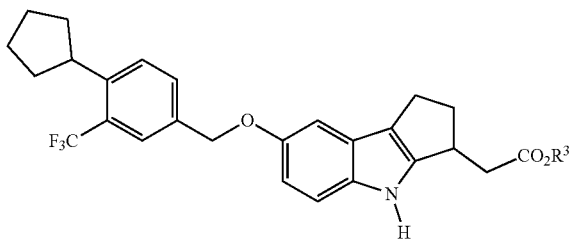

wherein $R^3$ is $C_1$-$C_6$ alkyl; in the presence of a hydrolyzing mixture comprising a lipase and a hydrolyzing-step solvent to form (R)-2-(7-(4-cyclopentyl-3-(trifluoromethyl)benzyloxy)-1,2,3,4-tetrahydrocyclopenta[b]indol-3-yl)acetic acid;
b) forming a first mixture comprising L-arginine salt of (R)-2-(7-(4-cyclopentyl-3-(trifluoromethyl)benzyloxy)-1,2,3,4-tetrahydrocyclopenta[b]indol-3-yl)acetic acid, a water-miscible anti-solvent, and $H_2O$;
c) heating the first mixture to a first heating temperature to form a second mixture;
d) adding a first additional amount of said water-miscible anti-solvent to said second mixture while maintaining said first heating temperature to form a suspension;
e) cooling said suspension to a first cooling temperature and thereafter heating to a second heating temperature;
f) cycling Step e) optionally one or more times, wherein said first cooling temperature at each cycle may be the same or different and said second heating temperature at each cycle may be the same or different; and
g) cooling said suspension to a final cooling temperature to form said crystalline free-plate habit of L-arginine salt of (R)-2-(7-(4-cyclopentyl-3-(trifluoromethyl)benzyloxy)-1,2,3,4-tetrahydrocyclopenta[b]indol-3-yl) acetic acid.

One aspect of the present invention relates to methods for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid, the method comprising the steps of:
a) adding L-arginine to a salt-forming mixture comprising (R)-2-(7-(4-cyclopentyl-3-(trifluoromethyl)benzyloxy)-1,2,3,4-tetrahydrocyclopenta[b]indol-3-yl)acetic acid, a water-miscible anti-solvent, and $H_2O$ to form a first mixture comprising L-arginine salt of (R)-2-(7-(4-cyclopentyl-3-(trifluoromethyl)benzyloxy)-1,2,3,4-tetrahydrocyclopenta[b]indol-3-yl)acetic acid;
b) heating the first mixture to a first temperature;
c) adding a first additional amount of the water-miscible anti-solvent to the first mixture to form a suspension; and
d) cooling the suspension to form the crystalline free-plate habit of L-arginine salt of (R)-2-(7-(4-cyclopentyl-3-

(trifluoromethyl)benzyloxy)-1,2,3,4-tetrahydrocyclopenta[b]indol-3-yl)acetic acid.

One aspect of the present invention relates to methods for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid, the method comprising the steps of:
  a) heating a first mixture comprising L-arginine salt of (R)-2-(7-(4-cyclopentyl-3-(trifluoromethyl)benzyloxy)-1,2,3,4-tetrahydrocyclopenta[b]indol-3-yl)acetic acid, a water-miscible anti-solvent, and water to a first heating temperature to form a second mixture;
  b) cooling the second mixture to a first cooling temperature followed by adding a first additional amount of the water-miscible anti-solvent to the second mixture while maintaining the first cooling temperature and thereafter heating to a second heating temperature to form a suspension; c) cycling Step b) optionally once or twice; and
  d) cooling the suspension to a second cooling temperature to form the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid.

One aspect of the present invention relates to methods for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid, said method comprising the steps of:
  a) forming a first mixture comprising L-arginine salt of (R)-2-(7-(4-cyclopentyl-3-(trifluoromethyl)benzyloxy)-1,2,3,4-tetrahydrocyclopenta[b]indol-3-yl)acetic acid, a water-miscible anti-solvent, and $H_2O$;
  b) heating the first mixture to a first heating temperature to form a second mixture;
  c) adding a first additional amount of said water-miscible anti-solvent to said second mixture while maintaining said first heating temperature to form a suspension;
  d) cooling the suspension to a first cooling temperature and thereafter heating to a second heating temperature;
  e) cycling Step d) optionally one or more times, wherein the first cooling temperature at each cycle may be the same or different and the second heating temperature at each cycle may be the same or different; and
  f) cooling said suspension to a final cooling temperature to form said crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid.

One aspect of the present invention relates to methods for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid further comprising the step of formulating the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid to form a pharmaceutical composition.

One aspect of the present invention relates to methods for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid further comprising the step of admixing the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid with a pharmaceutical excipient to form a pharmaceutical composition.

One aspect of the present invention relates to pharmaceutical compositions prepared according to any of the methods described herein.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid prepared according to any of the methods described herein.

One aspect of the present invention relates to compositions comprising a crystalline free-plate habit of L-arginine salt of (R)-2-(7-(4-cyclopentyl-3-(trifluoromethyl)benzyloxy)-1,2,3,4-tetrahydrocyclo-penta[b]indol-3-yl)acetic acid prepared according to any of the methods described herein.

One aspect of the present invention relates to pharmaceutical compositions comprising a crystalline free-plate habit of L-arginine salt of (R)-2-(7-(4-cyclopentyl-3-(trifluoromethyl)benzyloxy)-1,2,3,4-tetrahydrocyclo-penta[b]indol-3-yl)acetic acid prepared according to any of the methods described herein and a pharmaceutical excipient.

One aspect of the present invention relates to pharmaceutical compositions comprising a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid (Compound 1) in an amount equivalent to a therapeutically effective amount of Compound 1 of the crystalline free-plate habit, wherein the pharmaceutical composition further comprises a diluent, a disintegrant, and a lubricant.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid having a powder X-ray diffraction pattern comprising peaks, in terms of 2θ, at 8.2°±0.2°, 16.4°±0.2°, and 20.5°±0.2°.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid having a differential scanning calorimetry trace comprising an endotherm with an extrapolated onset temperature of 205.0° C. to 208.5° C. when scanned at 10° C. per minute.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid having a dynamic moisture sorption (DMS) profile with an adsorption phase from 30% RH to 90% RH wherein said crystalline free-plate habit gains about 0.3% weight or less at 90% RH.

One aspect of the present invention relates to compositions comprising a crystalline free-plate habit of L-arginine salt of (R)-2-(7-(4-cyclopentyl-3-(trifluoromethyl)benzyloxy)-1,2,3,4-tetrahydrocyclo-penta[b]indol-3-yl)acetic acid as described herein.

One aspect of the present invention relates to pharmaceutical compositions comprising a crystalline free-plate habit of L-arginine salt of (R)-2-(7-(4-cyclopentyl-3-(trifluoromethyl)benzyloxy)-1,2,3,4-tetrahydrocyclo-penta[b]indol-3-yl)acetic acid as described herein and a pharmaceutical excipient.

One aspect of the present invention relates to methods for treating an $S1P_1$ receptor-associated disorder in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein.

One aspect of the present invention relates to uses of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of an S1P$_1$ receptor-associated disorder.

One aspect of the present invention relates to uses of a composition comprising a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein and an excipient in the manufacture of a medicament for administration in the treatment of an S1P$_1$ receptor-associated disorder.

One aspect of the present invention relates to uses of a composition comprising a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein and an excipient for preparation a medicament for administration in the treatment of an S1P$_1$ receptor-associated disorder.

One aspect of the present invention relates to uses of a composition comprising a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein and an excipient for compounding a medicament for administration in the treatment of an S1P$_1$ receptor-associated disorder.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of the human or animal body by therapy.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of an S1P$_1$ receptor-associated disorder.

In some embodiments, the S1P$_1$ receptor-associated disorder is selected from: primary biliary cirrhosis, psoriasis, psoriatic arthritis, rheumatoid arthritis, Crohn's disease, multiple sclerosis, inflammatory bowel disease, systemic lupus erythematosus, and ulcerative colitis.

These and other aspects of the invention disclosed herein will be set forth in greater detail as the patent disclosure proceeds.

DETAILED DESCRIPTION OF THE INVENTION

Definitions

For clarity and consistency, the following definitions will be used throughout this patent document.

The phrase "L-arginine salt of Compound 1" refers to the L-arginine salt of (R)-2-(7-(4-cyclopentyl-3-(trifluoromethyl)benzyloxy)-1,2,3,4-tetrahydrocyclo-penta[b]indol-3-yl)acetic acid:

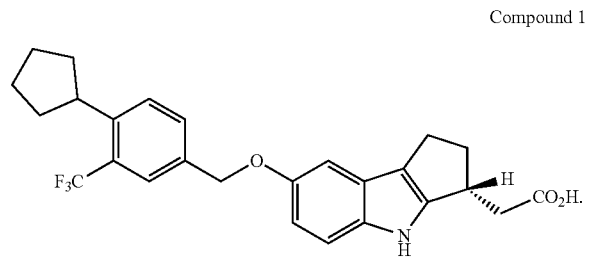 [SMILES: O=C(O)C[C@H]1CCc2c1[nH]c1ccc(OCc3ccc(C4CCCC4)c(C(F)(F)F)c3)cc21]

Compound 1

The phrase "as depicted in" with reference to a Figure refers to the crystal form and/or morphology as being characterized by graphical data "as depicted in" the Figure. Such data include, for example, powder X-ray diffractograms, differential scanning calorimetry traces, and dynamic moisture sorption graphs. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and/or morphology (habit) and confirm whether the two sets of graphical data are characterizing the same crystal form (or morphology) or two different crystal forms (or morphologies). A crystalline free-plate habit of the L-arginine salt of (R)-2-(7-(4-cyclopentyl-3-(trifluoromethyl)-benzyloxy)-1,2,3,4-tetrahydrocyclopenta[b]indol-3-yl)acetic acid (Compound 1) referred to herein as being characterized by graphical data "as depicted in" a Figure will thus be understood to include any morphologies characterized with the graphical data having such small variations, as are well known to the skilled person, in comparison with the Figure.

The term "composition" refers to a compound or salt thereof, such as, L-arginine salt of (R)-2-(7-(4-cyclopentyl-3-(trifluoromethyl)-benzyloxy)-1,2,3,4-tetrahydrocyclopenta[b]indol-3-yl)acetic acid, in combination with at least one additional component.

The term "formulating" as used herein refers to the step(s) to transform the bulk active pharmaceutical agent (i.e., API) into the drug substance or drug product for use in an individual for the treatment of a disease, wherein "treatment" and "individual" has the same definitions as described herein.

The phrase "free-plate habit" refers to the general shape of an independent substantially flat crystal with a length and width of the crystal being similar and substantially greater than the thickness and wherein the plate is not part of a radial cluster such as a spherulite. It is appreciated that due to the thin characteristic of the crystals, the phrase "free-plate habit" encompasses complete plates, substantially complete plates, fragments/broken pieces of plates, and mixtures thereof that are free or substantially free of radial clusters or spherulites.

Figure 1:
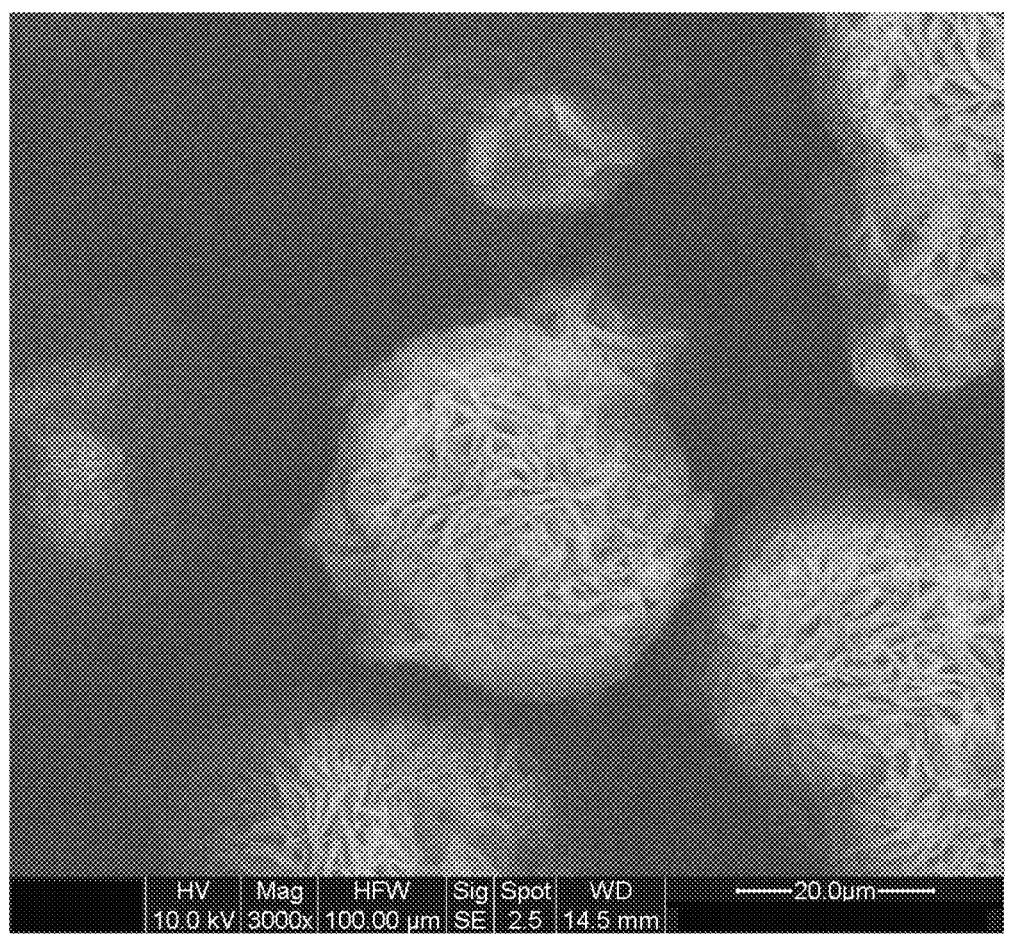
FIG. 1 shows a micrograph of spherulites/radial clusters using scanning electron microscopy (SEM), see Example 1 for additional details.
Figure 2:
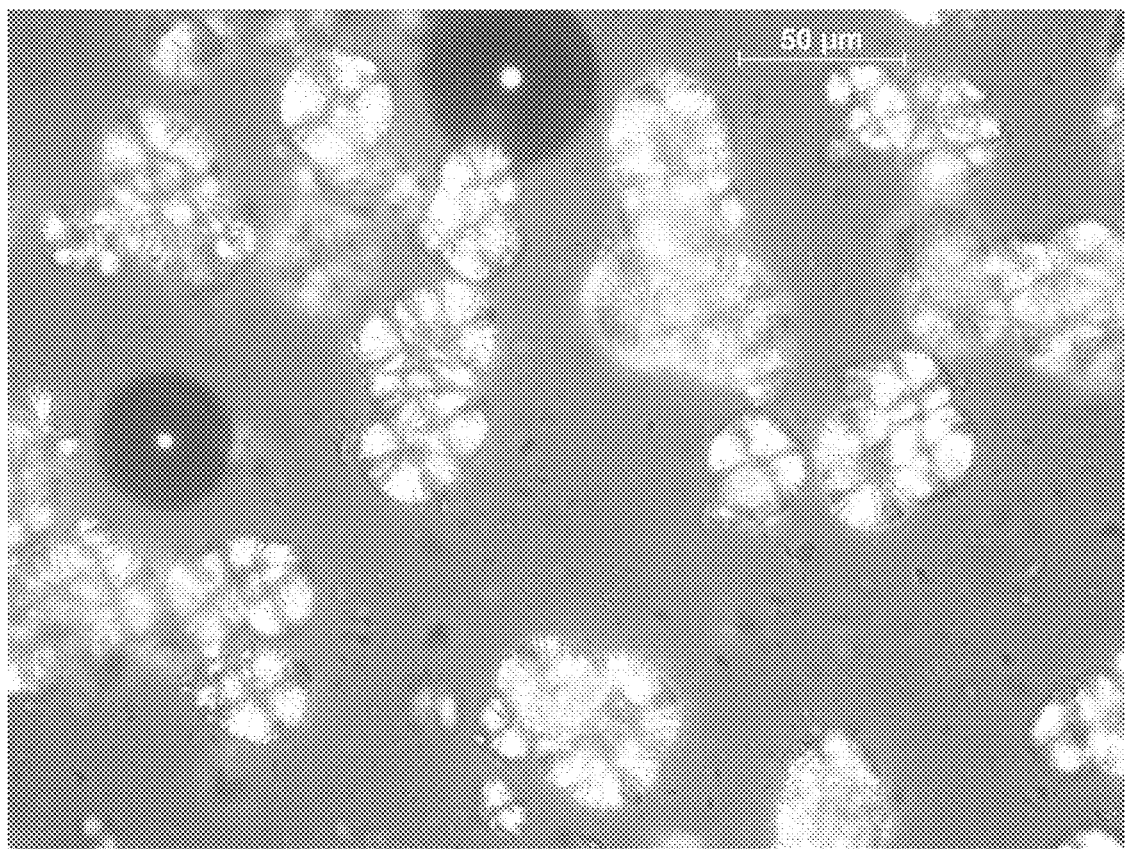
FIG. 2 shows a micrograph of spherulites/radial clusters using polarized light microscopy (PLM), see Example 1 for additional details.

The term "spherulite" and "radial cluster" refers to a crystal habit consisting of thin plates or flakes that are clustered in a radial manner around a nucleation site that exhibit a cross when viewed using crossed-polarized light, see FIG. 1 and FIG. 2 for micrographs of representative spherulites/radial clusters. Typically the length of the thin plates making up the radial cluster is less than 10 μm.

The term "length" in the context of a crystalline habit refers to the longest dimension from edge to edge of a particle oriented parallel to the ocular scale.

The term "width" in the context of a crystalline habit refers to the longest dimension of the particle measured at right angles to the length.

The term "individual" as used herein refers to any animal, including mammals, preferably mice, rats, other rodents, rabbits, dogs, cats, swine, cattle, sheep, horses, or primates and most preferably humans.

The term "inert atmosphere" as used herein refers to an atmosphere substantially free of oxygen. Examples of an inert atmosphere include, for example, argon and nitrogen.

The term "pharmaceutical composition" as used herein refers to a composition comprising at least one active ingredient; such as Compound 1 and the L-arginine salt thereof, whereby the composition is amenable to investigation for a specified pharmacological outcome in a mammal (for example, without limitation, a human) or the treatment of a disease or disorder as described herein. Those of ordinary skill in the art will understand and appreciate the techniques appropriate for determining whether an active ingredient has a desired efficacious outcome based upon the needs of the artisan.

The term "treatment" or "treating" as used herein includes one or more of the following:

(1) prevention of a disease, for example, prevention of a disease, condition or disorder in an individual that may be predisposed to the disease, condition or disorder but does not yet experience or display the pathology or symptomatology of the disease;

(2) inhibition of a disease, for example, inhibition of a disease, condition or disorder in an individual that is experiencing or displaying the pathology or symptomatology of the disease, condition or disorder (i.e., arresting further development of the pathology and/or symptomatology); and (3) amelioration of a disease, for example, amelioration of a disease, condition or disorder in an individual that is experiencing or displaying the pathology or symptomatology of the disease, condition or disorder (i.e., reversing the pathology and/or symptomatology).

Whether an individual is in need of treatment is a judgment made by a caregiver (e.g. nurse practitioner, physician, physician assistant, nurse, etc. in the case of humans; veterinarian in the case of animals, including non-human mammals) that an individual or animal requires or will benefit from treatment. This judgment is made based on a variety of factors that are in the realm of a caregivers expertise, but that includes the knowledge that the individual or animal is ill, or will become ill, as the result of a disease, condition or disorder that is treatable by Compound 1 or a pharmaceutically acceptable salt, solvate, and hydrate thereof, such as, the L-arginine salt of Compound 1. Accordingly, Compound 1 and/or pharmaceutically acceptable salts, solvates and hydrates thereof, such as, the L-arginine salt of Compound 1, can be used in a protective or preventive manner; or Compound 1 and pharmaceutically acceptable salts, solvates and hydrates thereof, such as, the L-arginine salt of Compound 1, can be used to alleviate, inhibit, or ameliorate a disease, condition, or disorder.

The phrase "water-miscible anti-solvent" as used herein refers to a water soluble solvent in which the product, such as the L-arginine salt of (R)-2-(7-(4-cyclopentyl-3-(trifluoromethyl)-benzyloxy)-1,2,3,4-tetrahydrocyclopenta[b]indol-3-yl)acetic acid, has limited solubility.

Chemical Group, Moiety or Radical

The term "$C_2$-$C_4$ alkanol" refers to a straight or branched carbon radical containing 2 to 4 carbons bonded to an —OH group. Some embodiments are 2 to 3 carbons and some embodiments are 3 to 4 carbons. Examples of a $C_2$-$C_4$ alkanol include, but are not limited to, ethanol, 1-propanol, 2-propanol, 1-butanol, 2-butanol, and the like.

The term "$C_1$-$C_6$ alkyl" refers to a straight or branched carbon radical containing 1 to 6 carbons. Some embodiments are 1 to 5 carbons, some embodiments are 1 to 4 carbons, some embodiments are 1 to 3 carbons and some embodiments are 1 or 2 carbons. Examples of an alkyl include, but are not limited to, methyl, ethyl, n-propyl, isopropyl, n-butyl, sec-butyl, isobutyl, tert-butyl, pentyl, isopentyl, tert-pentyl, neo-pentyl, 1-methylbutyl [i.e., $CH(CH_3)Cl_2CH_2CH_3$], 2-methylbutyl [i.e., $CH_2CH(CH_3)CH_2CH_3$], n-hexyl and the like.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. In addition, subcombinations of uses and medical indications listed in the embodiments describing such uses and medical indications described herein, are also specifically embraced by the present invention just as if each and every subcombination of uses and medical indications was individually and explicitly recited herein.

Certain Methods of the Invention

Described herein are methods for preparing the crystalline plate morphology of the L-arginine salt of (R)-2-(7-(4-cyclopentyl-3-(trifluoromethyl)benzyloxy)-1,2,3,4-tetrahydrocyclo-penta[b]indol-3-yl)acetic acid using an enzymatic hydrolysis of the corresponding (R/S)-ethyl ester to the (R)-acid followed by a modified L-arginine salt-forming procedure compared to what was previously disclosed in WO2011/094008 and isolating the L-arginine salt of Compound 1 as the crystalline free-plate habit or morphology.

Accordingly, one aspect of the present invention relates to methods for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid, the method comprising the steps of:

a) hydrolyzing a compound of Formula (IIa):

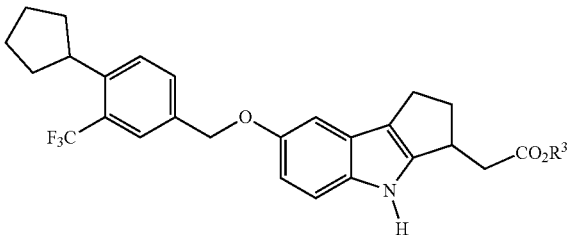

(IIa)

wherein $R^3$ is $C_1$-$C_6$ alkyl; in the presence of a hydrolyzing mixture comprising a lipase and a hydrolyzing-step solvent to form (R)-2-(7-(4-cyclopentyl-3-(trifluoromethyl)benzyloxy)-1,2,3,4-tetrahydrocyclopenta[b]indol-3-yl)acetic acid;

b) adding L-arginine to a salt-forming mixture comprising (R)-2-(7-(4-cyclopentyl-3-(trifluoromethyl)benzyloxy)-1,2,3,4-tetrahydrocyclopenta[b]indol-3-yl)acetic acid, a water-miscible anti-solvent, and $H_2O$ to form a first mixture comprising L-arginine salt of (R)-2-(7-(4-cyclopentyl-3-(trifluoromethyl)benzyloxy)-1,2,3,4-tetrahydrocyclopenta[b]indol-3-yl)acetic acid;

c) heating the first mixture to a first heating temperature;

d) adding a first additional amount of the water-miscible anti-solvent to the first mixture to form a suspension; and e) cooling the suspension to form the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid.

In some embodiments, the method for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid is conducted under an inert atmosphere. In some embodiments, the method is conducted under an inert atmosphere comprising nitrogen or argon. In some embodiments, the method is conducted under an inert atmosphere comprising nitrogen.

Step a)—Hydrolyzing a Compound of Formula (IIa)

In some embodiments, the hydrolyzing in Step a) is conducted under an inert atmosphere. In some embodiments, the hydrolyzing in Step a) is conducted under an inert atmosphere comprising nitrogen or argon. In some embodiments, the hydrolyzing in Step a) is conducted under an inert atmosphere comprising nitrogen.

In some embodiments, $R^3$ is methyl or ethyl. In some embodiments, $R^3$ is ethyl.

In some embodiments, the lipase is *Candida antarctica* lipase B. In some embodiments, the lipase is immobilized *Candida antarctica* lipase B.

In some embodiments, the hydrolyzing-step solvent comprises dimethylformamide (DMF), dimethylacetamide (DMA), dimethylsulfoxide (DMSO), tetrahydrofuran (THF), or acetonitrile. In some embodiments, the hydrolyzing-step solvent comprises acetonitrile.

In some embodiments, the compound of Formula (IIa) is:

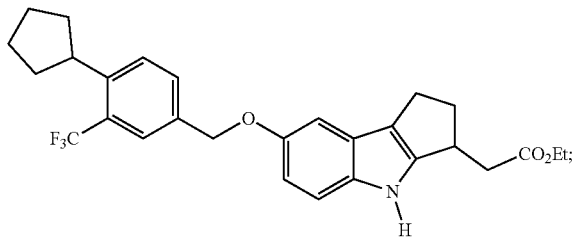 [SMILES: CCOC(=O)CC1CCc2c1[nH]c1ccc(OCc3ccc(C4CCCC4)c(C(F)(F)F)c3)cc21]

the lipase is immobilized *Candida antarctica* lipase B; and the hydrolyzing-step solvent comprises acetonitrile.

In some embodiments, the hydrolyzing in Step a) is conducted in the presence of a phosphate buffer. In some embodiments, the hydrolyzing in Step a) is conducted in the presence of a phosphate buffer at a pH of about 6.0 to about 9.0. In some embodiments, the hydrolyzing in Step a) is conducted in the presence of a phosphate buffer at a pH of about 7.0 to about 8.5. In some embodiments, the hydrolyzing in Step a) is conducted in the presence of a phosphate buffer at a pH of about 7.3 to about 8.3. In some embodiments, the hydrolyzing in Step a) is conducted in the presence of a phosphate buffer at a pH of about 7.6 to about 8.0. In some embodiments, the hydrolyzing in Step a) is conducted in the presence of a phosphate buffer at a pH of about 7.8. In some embodiments, the phosphate buffer is a sodium phosphate buffer. In some embodiments, the phosphate buffer is a potassium phosphate buffer.

In some embodiments, the hydrolyzing in Step a) is conducted at a temperature of about 0° C. to about 75° C. In some embodiments, the hydrolyzing in Step a) is conducted at a temperature of about 20° C. to about 65° C. In some embodiments, the hydrolyzing in Step a) is conducted at a temperature of about 30° C. to about 55° C. In some embodiments, the hydrolyzing in Step a) is conducted at a temperature of about 35° C. to about 45° C.

In some embodiments, the hydrolyzing in Step a) further comprises the step of isolating the (R)-2-(7-(4-cyclopentyl-3-(trifluoromethyl)benzyloxy)-1,2,3,4-tetrahydrocyclopenta[b]indol-3-yl)acetic acid.

In some embodiments, after isolating, the (R)-2-(7-(4-cyclopentyl-3-(trifluoromethyl)-benzyloxy)-1,2,3,4-tetrahydrocyclopenta[b]indol-3-yl)acetic acid has an enantiomeric excess of about 95% or greater. In some embodiments, after isolating, the (R)-2-(7-(4-cyclopentyl-3-(trifluoromethyl)-benzyloxy)-1,2,3,4-tetrahydrocyclopenta[b]indol-3-yl)acetic acid has an enantiomeric excess of about 98% or greater. In some embodiments, after isolating, the (R)-2-(7-(4-cyclopentyl-3-(trifluoromethyl)-benzyloxy)-1,2,3,4-tetrahydrocyclopenta[b]indol-3-yl)acetic acid has an enantiomeric excess of about 99% or greater.

Step b)—Adding L-Arginine to a Salt-Forming Mixture

In some embodiments, the adding in Step b) is conducted under an inert atmosphere. In some embodiments, the adding in Step b) is conducted under an inert atmosphere comprising argon or nitrogen. In some embodiments, the adding in Step b) is conducted under an inert atmosphere comprising nitrogen.

In some embodiments, the water-miscible anti-solvent in Step b) comprises a solvent selected from the group consisting of: acetonitrile, acetone, tetrahydrofuran, and $C_2$-$C_4$ alkanol. In some embodiments, the water-miscible anti-solvent in Step b) comprises a solvent selected from the group consisting of: acetonitrile, acetone, tetrahydrofuran, ethanol, 1-propanol, 2-propanol, and 1-butanol. In some embodiments, the water-miscible anti-solvent in Step b) comprises 2-propanol.

In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:0.95 to about 1.0:1.2. In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:1.0 to about 1.0:1.2. In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:1.0.

In some embodiments, the salt-forming mixture prior to the adding L-arginine is at a temperature of about 15° C. to about 83° C. In some embodiments, the salt-forming mixture prior to the adding L-arginine is at a temperature of about 18° C. to about 80° C. In some embodiments, the salt-forming mixture prior to the adding L-arginine is at a temperature of about 20° C. to about 40° C.

One aspect of the present invention allows for the L-arginine to be added to the salt-forming mixture as a solid.

In some embodiments, the adding L-arginine in Step b) is conducted by adding L-arginine as a solid to the salt-forming mixture.

In some embodiments, the adding L-arginine in Step b) is conducted by adding L-arginine as a solid to the salt-forming mixture substantially all at once. The phrase "substantially all at once" or "all at once" refers to the addition of all of the L-arginine to the salt-forming mixture at one time with the only limitation that is placed on the addition is by any limitation associated with the equipment used.

In some embodiments, the adding L-arginine in Step b) is conducted by adding L-arginine as a solid to the salt-forming mixture over a period of 30 minutes. In some embodiments, the adding L-arginine in Step b) is conducted by adding L-arginine as a solid to the salt-forming mixture over a period of 1 hour. In some embodiments, the adding L-arginine in Step b) is conducted by adding L-arginine as a solid to the salt-forming mixture over a period of 2 hours.

In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.00:4.98:0.94 to about 1.00:7.46:1.40. In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.00:5.29:0.99 to about 1.00:7.15:1.35. In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.00:5.60:1.05 to about 1.00:6.84:1.29. In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.00:5.72:1.08 to about 1.00:6.72:1.26. In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.00:5.85:1.10 to about 1.00:6.59:1.24. In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.00:5.97:1.12 to about 1.00:6.47:1.22. In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.00:6.10:1.15 to about 1.00:6.34:1.19. In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.00:6.22:1.17.

In some embodiments, the salt-forming mixture during the adding L-arginine is at a temperature of about 15° C. to about 83° C. In some embodiments, the salt-forming mixture during the adding L-arginine is at a temperature of about 18° C. to about 80° C. In some embodiments, the salt-forming mixture during the adding L-arginine is at a temperature of about 20° C. to about 40° C.

One aspect of the present invention allows for the L-arginine to be added to the salt-forming mixture as an aqueous solution.

In some embodiments, the adding L-arginine in Step b) is conducted by adding L-arginine as an aqueous solution to the salt-forming mixture.

In some embodiments, the adding L-arginine in Step b) is conducted by adding L-arginine to the salt-forming mixture wherein L-arginine is a solution of about 2.1M to about 2.3M aqueous solution at a temperature of about 50° C. to about 75° C. In some embodiments, the adding L-arginine in Step b) is conducted by adding L-arginine to the salt-forming mixture wherein L-arginine is a solution of about 2.26 M to about 2.28 M aqueous solution at a temperature of about 55° C. to about 65° C.

In some embodiments, after adding L-arginine as an aqueous solution in Step b) the weight ratio of (R)-2-(7-(4-cyclopentyl-3-(trifluoromethyl)benzyloxy)-1,2,3,4-tetrahydro-cyclopenta[b]indol-3-yl)acetic acid, 2-propanol, and $H_2O$ is about 1.00:4.98:0.94 to about 1.00:7.46:1.40. In some embodiments, after adding L-arginine as an aqueous solution in Step b) the weight ratio of (R)-2-(7-(4-cyclopentyl-3-(trifluoromethyl)benzyloxy)-1,2,3,4-tetrahydro-cyclopenta[b]indol-3-yl)acetic acid, 2-propanol, and $H_2O$ is about 1.00:5.29:0.99 to about 1.00:7.15:1.35. In some embodiments, after adding L-arginine as an aqueous solution in Step b) the weight ratio of (R)-2-(7-(4-cyclopentyl-3-(trifluoro-methyl)benzyloxy)-1,2,3,4-tetrahydro-cyclopenta[b]indol-3-yl)acetic acid, 2-propanol, and $H_2O$ is about 1.00:5.60:1.05 to about 1.00:6.84:1.29. In some embodiments, after adding L-arginine as an aqueous solution in Step b) the weight ratio of (R)-2-(7-(4-cyclopentyl-3-(trifluoromethyl)benzyloxy)-1,2,3,4-tetrahydro-cyclopenta[b]indol-3-yl)acetic acid, 2-propanol, and $H_2O$ is about 1.00:5.72:1.08 to about 1.00:6.72:1.26. In some embodiments, after adding L-arginine as an aqueous solution in Step b) the weight ratio of (R)-2-(7-(4-cyclopentyl-3-(trifluoromethyl)benzyloxy)-1,2,3,4-tetrahydro-cyclo-penta[b]indol-3-yl)acetic acid, 2-propanol, and $H_2O$ is about 1.00:5.85:1.10 to about 1.00:6.59:1.24. In some embodiments, after adding L-arginine as an aqueous solution in Step b) the weight ratio of (R)-2-(7-(4-cyclopentyl-3-(trifluoromethyl)benzyloxy)-1,2,3,4-tetrahydro-cyclopenta[b]indol-3-yl)acetic acid, 2-propanol, and $H_2O$ is about 1.00:5.97:1.12 to about 1.00:6.47:1.22. In some embodiments, after adding L-arginine as an aqueous solution in Step b) the weight ratio of (R)-2-(7-(4-cyclopentyl-3-(trifluoromethyl)benzyloxy)-1,2,3,4-tetrahydro-cyclopenta[b]indol-3-yl)acetic acid, 2-propanol, and $H_2O$ is about 1.00:6.10:1.15 to about 1.00:6.34:1.19. In some embodiments, after adding L-arginine as an aqueous solution in Step b) the weight ratio of (R)-2-(7-(4-cyclopentyl-3-(trifluoromethyl)benzyl-oxy)-1,2,3,4-tetrahydro-cyclopenta[b]indol-3-yl)acetic acid, 2-propanol, and $H_2O$ is about 1.00:6.22:1.17.

In some embodiments, Step b) is conducted at a stir rate of about 100 rpm to about 200 rpm. In some embodiments, Step b) is conducted at a stir rate of about 125 rpm to about 175 rpm. In some embodiments, Step b) is conducted at a stir rate of about 150 rpm.

Step c)—Heating the First Mixture to a First Heating Temperature

In some embodiments, the first heating temperature is about 20° C. to about 83° C. In some embodiments, the first heating temperature is about 20° C. to about 55° C. In some embodiments, the first heating temperature is about 25° C. to about 45° C. In some embodiments, the first heating temperature is about 50° C. to about 83° C. In some embodiments, the first heating temperature is about 60° C. to about 80° C. In some embodiments, the first heating temperature is about 70° C. to about 80° C.

In some embodiments, the first mixture is substantially a homogeneous solution.

In some embodiments, Step c) is conducted at a stir rate of about 100 rpm to about 200 rpm. In some embodiments, Step c) is conducted at a stir rate of about 125 rpm to about 175 rpm. In some embodiments, Step c) is conducted at a stir rate of about 150 rpm.

Step d)—Adding a First Additional Amount of the Water-Miscible Anti-Solvent to the First Mixture to Form a Suspension In some embodiments, the water-miscible anti-solvent in Step b) comprises a solvent selected from the group consisting of: acetonitrile, acetone, tetrahydrofuran, and $C_2$-$C_4$ alkanol. In some embodiments, the water-miscible anti-solvent in Step b) comprises a solvent selected from the group consisting of: acetonitrile, acetone, tetrahydrofuran, ethanol, 1-propanol, 2-propanol, and 1-butanol. In some embodiments, the water-miscible anti-solvent in Step b) comprises 2-propanol.

In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:5.46 to about 1.00:8.20. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:5.81 to about 1.00:7.86. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:6.15 to about 1.00:7.51. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:6.28 to about 1.00:7.38. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:6.42 to about 1.00:7.24. In some embodiments, the weight ratio of L-arginine salt of (R)-2-(7-(4-cyclopentyl-3-(trifluoromethyl)benzyloxy)-1,2,3,4-tetrahydrocyclopenta[b]indol-3-yl)acetic acid to the first additional amount of 2-propanol is about 1.00:6.56 to about 1.00:7.10. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:6.69 to about 1.00:6.97. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:6.83.

In some embodiments, adding the first additional amount of 2-propanol to the first mixture is conducted at a rate to complete the addition in about 5.00 hours to about 10.00 hours. In some embodiments, adding the first additional amount of 2-propanol to the first mixture is conducted at a rate to complete the addition in about 6.75 hours to about 8.25 hours. In some embodiments, adding the first additional amount of 2-propanol to the first mixture is conducted at a rate to complete the addition in about 6.90 hours to about 8.10 hours. In some embodiments, adding the first additional amount of 2-propanol to the first mixture is conducted at a rate to complete the addition in about 7.05 hour to about 7.95 hour. In some embodiments, adding the first additional amount of 2-propanol to the first mixture is conducted at a rate to complete the addition in about 7.20 hours to about 7.80 hours. In some embodiments, adding the first additional amount of 2-propanol to the first mixture is conducted at a rate to complete the addition in about 7.35 hours to about 7.65 hours. In some embodiments, adding the first additional amount of 2-propanol to the first mixture is conducted at a rate to complete the addition in about 7.50 hours.

In some embodiments, the first heating temperature is maintained during adding the first additional amount of 2-propanol to the first mixture.

In some embodiments, after adding the first additional amount of 2-propanol to the first mixture in Step c), the method further comprises forming a second mixture while maintaining the first heating temperature, wherein the second mixture is formed prior to forming the suspension.

In some embodiments, the method further comprises cooling the second mixture to a first cooling temperature followed by heating to a second heating temperature to form the suspension.

In some embodiments, cooling the second mixture to the first cooling temperature is conducted at a rate of about 8.80° C./hour to about 14.40° C./hour. In some embodiments, cooling the second mixture to the first cooling temperature is conducted at a rate of about 9.35° C./hour to about 13.80° C./hour. In some embodiments, cooling the second mixture to the first cooling temperature is conducted at a rate of about 9.90° C./hour to about 13.20° C./hour. In some embodiments, cooling the second mixture to the first cooling temperature is conducted at a rate of about 10.45° C./hour to about 12.60° C./hour. In some embodiments, cooling the second mixture to the first cooling temperature is conducted at a rate of about 10° C./hour to about 12° C./hour.

In some embodiments, the first cooling temperature is about 15° C. to about 40° C. In some embodiments, the first cooling temperature is about 20° C. to about 30° C. In some embodiments, the first cooling temperature is about 22° C. to about 24° C.

In some embodiments, the first cooling temperature is maintained for at least 1 hour prior to heating to the second heating temperature.

In some embodiments, the second heating temperature is about 65° C. to about 83° C. In some embodiments, the second heating temperature is about 70° C. to about 80° C. In some embodiments, the second heating temperature is about 70° C. to about 75° C.

In some embodiments, after heating to the second heating temperature, the second heating temperature is maintained for at least 30 minutes.

In some embodiments, Step d) is conducted at a stir rate of about 100 rpm to about 200 rpm. In some embodiments, Step d) is conducted at a stir rate of about 125 rpm to about 175 rpm. In some embodiments, Step d) is conducted at a stir rate of about 150 rpm.

Step e)—Cooling the Suspension to Form the Crystalline Free-Plate Habit of L-Arginine Salt of (R)-2-(7-(4-Cyclopentyl-3-(trifluoromethyl)benzyloxy)-1,2,3,4-tetrahydrocyclo-penta[b]indol-3-yl)acetic Acid In some embodiments, cooling the suspension in Step e) is conducted at a rate of about 8.8° C./hour to about 14.4° C./hour. In some embodiments, cooling the suspension in Step e) is conducted at a rate of about 9.4° C./hour to about 13.8° C./hour. In some embodiments, cooling the suspension in Step e) is conducted at a rate of about 9.9° C./hour to about 13.2° C./hour. In some embodiments, cooling the suspension in Step e) is conducted at a rate of about 10.5° C./hour to about 12.6° C./hour. In some embodiments, cooling the suspension in Step e) is conducted at a rate of about 10° C./hour to about 12° C./hour.

In some embodiments, after cooling in Step e) the temperature of the suspension is about 15° C. to about 40° C. In some embodiments, after cooling in Step e) the temperature of the suspension is about 20° C. to about 30° C. In some embodiments, after cooling in Step e) the temperature of the suspension is about 22° C. to about 24° C.

In some embodiments, Step e) is conducted at a stir rate of about 100 rpm to about 200 rpm. In some embodiments, Step e) is conducted at a stir rate of about 125 rpm to about 175 rpm. In some embodiments, Step e) is conducted at a stir rate of about 150 rpm.

In some embodiments, the method further comprises the step of isolating the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid.

In some embodiments, the step of isolating comprises filtering the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid from the suspension. In some embodiments, the step of isolating comprises filtering the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid from the suspension and drying the crystalline free-plate habit of L-arginine salt at a reduced pressure.

In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has an onset temperature of 205.0° C. to 208.5° C. as determined by differential scanning calorimetry at a scan rate of 10° C./minute. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has an onset temperature of 205.5° C. to 208.5° C. as determined by differential scanning calorimetry at a scan rate of 10° C./minute. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has an onset temperature of 206.5° C. to 208.5° C. as determined by differential scanning calorimetry at a scan rate of 10° C./minute. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has an onset temperature of 207.0° C. to 208.1° C. as determined by differential scanning calorimetry at a scan rate of 10° C./minute. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a differential scanning calorimetry trace conducted at a scan rate of 10° C./minute comprising an endotherm substantially as depicted in any one of FIGS. 6 to 10. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a differential scanning calorimetry trace conducted at a scan rate of 10° C./minute comprising an endotherm substantially as depicted in any one of FIGS. 6 to 10 and FIGS. 22 to 25. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a dynamic moisture sorption (DMS) profile with an adsorption phase from 30% RH to 90% RH wherein the crystalline free-plate habit gains about 0.3% weight or less at 90% RH. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a dynamic moisture sorption (DMS) profile with an adsorption phase from 30% RH to 90% RH wherein the crystalline free-plate habit gains about 0.2% weight or less at 90% RH. The DMS features reported herein can also vary by plus or minus about 0.15% weight change (i.e., ±0.15% weight change).

In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a total impurity profile by achiral HPLC of less than or equal to 0.5% by area. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a total impurity profile by achiral HPLC of less than or equal to 0.3% by area. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a total impurity profile by achiral HPLC of less than or equal to 0.2% by area.

In some embodiments, the method further comprises the step of formulating the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid to form a pharmaceutical composition.

In some embodiments, the method further comprises the step of admixing the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid with a pharmaceutical excipient to form a pharmaceutical composition.

One aspect of the present invention relates to methods for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid, the method comprising the steps of:

a) hydrolyzing a compound of Formula (IIa):

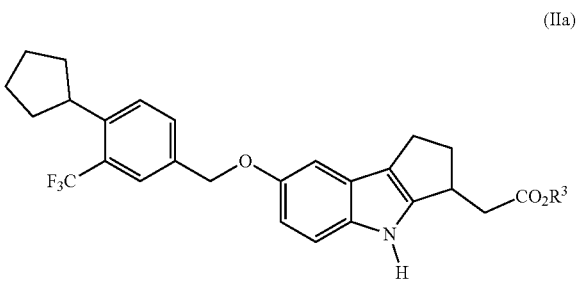

(IIa)

wherein $R^3$ is $C_1$-$C_6$ alkyl; in the presence of a hydrolyzing mixture comprising a lipase and a hydrolyzing-step solvent to form (R)-2-(7-(4-cyclopentyl-3-(trifluoromethyl)benzyloxy)-1,2,3,4-tetrahydrocyclopenta[b]indol-3-yl)acetic acid;

b) adding L-arginine to a salt-forming mixture comprising (R)-2-(7-(4-cyclopentyl-3-(trifluoromethyl)benzyloxy)-1,2,3,4-tetrahydrocyclopenta[b]indol-3-yl)acetic acid, 2-propanol, and $H_2O$ to form a first mixture comprising L-arginine salt of (R)-2-(7-(4-cyclopentyl-3-(trifluoromethyl)benzyloxy)-1,2,3,4-tetrahydrocyclopenta[b]indol-3-yl)acetic acid;

c) heating the first mixture to a first heating temperature;

d) adding a first additional amount of the 2-propanol to the first mixture to form a suspension; and e) cooling the suspension to form the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid. Further description of the embodiments for these methods as related to Steps a) to e) can be found herein, for example, see Steps a) to e) respectively, supra.

Also described herein are methods for preparing a crystalline free-plate habit of the L-arginine salt of (R)-2-(7-(4-cyclopentyl-3-(trifluoromethyl)benzyloxy)-1,2,3,4-tetrahydrocyclo-penta[b]indol-3-yl)acetic acid starting from (R)-2-(7-(4-cyclopentyl-3-(trifluoromethyl)benzyloxy)-1,2,3,4-tetrahydrocyclopenta[b]indol-3-yl)acetic acid.

Accordingly, one aspect of the present invention relates to methods for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid, the method comprising the steps of:

a) adding L-arginine to a salt-forming mixture comprising (R)-2-(7-(4-cyclopentyl-3-(trifluoromethyl)benzyloxy)-1,2,3,4-tetrahydrocyclopenta[b]indol-3-yl)acetic acid, a water-miscible anti-solvent, and $H_2O$ to form a first mixture comprising L-arginine salt of (R)-2-(7-(4-cyclopentyl-3-(trifluoromethyl)benzyloxy)-1,2,3,4-tetrahydrocyclopenta[b]indol-3-yl)acetic acid;

b) heating the first mixture to a first temperature;

c) adding a first additional amount of the water-miscible anti-solvent to the first mixture to form a suspension; and d) cooling the suspension to form the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid. Further description of the embodiments for these methods as related to Steps a) to d) can be found herein, for example, see Steps b) to e) respectively, supra.

Another aspect of the present invention relates to methods for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid, the method comprising the steps of:
  a) adding L-arginine to a salt-forming mixture comprising (R)-2-(7-(4-cyclopentyl-3-(trifluoromethyl)benzyloxy)-1,2,3,4-tetrahydrocyclopenta[b]indol-3-yl)acetic acid, 2-propanol, and $H_2O$ to form a first mixture comprising L-arginine salt of (R)-2-(7-(4-cyclopentyl-3-(trifluoromethyl)benzyloxy)-1,2,3,4-tetrahydrocyclopenta[b]indol-3-yl)acetic acid;
  b) heating the first mixture to a first temperature;
  c) adding a first additional amount of 2-propanol to the first mixture to form a suspension; and
  d) cooling the suspension to form the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid. Further description of the embodiments for these methods as related to Steps a) to d) can be found herein, for example, see Steps b) to e) respectively, supra.

One aspect of the present invention relates to methods for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid, the method comprising the steps of:
  a) hydrolyzing a compound of Formula (IIa):

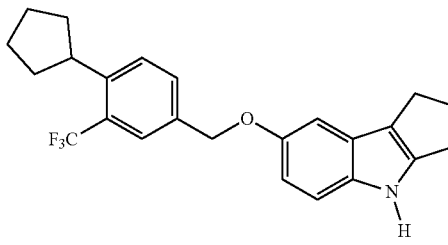

(IIa)

wherein $R^3$ is $C_1$-$C_6$ alkyl; in the presence of a hydrolyzing mixture comprising a lipase and a hydrolyzing-step solvent to form (R)-2-(7-(4-cyclopentyl-3-(trifluoromethyl)benzyloxy)-1,2,3,4-tetrahydrocyclopenta[b]indol-3-yl)acetic acid;
  b) forming a first mixture comprising L-arginine salt of (R)-2-(7-(4-cyclopentyl-3-(trifluoromethyl)benzyloxy)-1,2,3,4-tetrahydrocyclopenta[b]indol-3-yl)acetic acid, a water-miscible anti-solvent, and $H_2O$;
  c) heating the first mixture to a first heating temperature to form a second mixture;
  d) adding a first additional amount of the water-miscible anti-solvent to the second mixture while maintaining the first heating temperature to form a suspension;
  e) cooling the suspension to a first cooling temperature and thereafter heating to a second heating temperature;
  f) cycling Step e) optionally one or more times, wherein the first cooling temperature at each cycle may be the same or different and the second heating temperature at each cycle may be the same or different; and
  g) cooling the suspension to a final cooling temperature to form the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid.

In some embodiments, the method for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid is conducted under an inert atmosphere. In some embodiments, the method is conducted under an inert atmosphere comprising nitrogen or argon. In some embodiments, the method is conducted under an inert atmosphere comprising nitrogen.

Step a)—Hydrolyzing a Compound of Formula (IIa)

In some embodiments, the hydrolyzing in Step a) is conducted under an inert atmosphere. In some embodiments, the hydrolyzing in Step a) is conducted under an inert atmosphere comprising nitrogen or argon. In some embodiments, the hydrolyzing in Step a) is conducted under an inert atmosphere comprising nitrogen.

In some embodiments, $R^3$ is methyl or ethyl. In some embodiments, $R^3$ is ethyl.

In some embodiments, the lipase is *Candida antarctica* lipase B. In some embodiments, the lipase is immobilized *Candida antarctica* lipase B.

In some embodiments, the hydrolyzing-step solvent comprises dimethylformamide (DMF), dimethylacetamide (DMA), dimethylsulfoxide (DMSO), tetrahydrofuran (THF), or acetonitrile. In some embodiments, the hydrolyzing-step solvent comprises acetonitrile.

In some embodiments, the compound of Formula (IIa) is:

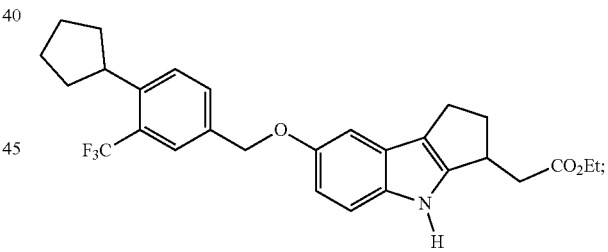

the lipase is immobilized *Candida antarctica* lipase B; and the hydrolyzing-step solvent comprises acetonitrile.

In some embodiments, the hydrolyzing is conducted in the presence of a phosphate buffer. In some embodiments, the hydrolyzing is conducted in the presence of a phosphate buffer at a pH of about 6.0 to about 9.0. In some embodiments, the hydrolyzing is conducted in the presence of a phosphate buffer at a pH of about 6.9 to about 8.1. In some embodiments, the hydrolyzing is conducted in the presence of a phosphate buffer at a pH of about 7.0 to about 8.5. In some embodiments, the hydrolyzing is conducted in the presence of a phosphate buffer at a pH of about 7.3 to about 8.3. In some embodiments, the hydrolyzing is conducted in the presence of a phosphate buffer at a pH of about 7.6 to about 8.0. In some embodiments, the hydrolyzing is conducted in the presence of a phosphate buffer at a pH of about 7.8. In some embodiments, the phosphate buffer is a sodium phosphate buffer. In some embodiments, the phosphate buffer is a potassium phosphate buffer.

In some embodiments, the hydrolyzing is conducted at a temperature of about 0° C. to about 75° C. In some embodiments, the hydrolyzing is conducted at a temperature of about 20° C. to about 65° C. In some embodiments, the hydrolyzing is conducted at a temperature of about 30° C. to about 55° C. In some embodiments, the hydrolyzing is conducted at a temperature of about 35° C. to about 45° C.

In some embodiments, the hydrolyzing further comprises the step of isolating the (R)-2-(7-(4-cyclopentyl-3-(trifluoromethyl)benzyloxy)-1,2,3,4-tetrahydrocyclopenta[b]indol-3-yl)acetic acid.

In some embodiments, after the isolating, the (R)-2-(7-(4-cyclopentyl-3-(trifluoromethyl)benzyloxy)-1,2,3,4-tetrahydrocyclopenta[b]indol-3-yl)acetic acid has an enantiomeric excess of about 95% or greater. In some embodiments, after the isolating, the (R)-2-(7-(4-cyclopentyl-3-(trifluoromethyl)benzyloxy)-1,2,3,4-tetrahydrocyclopenta[b]indol-3-yl)acetic acid has an enantiomeric excess of about 98% or greater. In some embodiments, after the isolating, the (R)-2-(7-(4-cyclopentyl-3-(trifluoromethyl)benzyloxy)-1,2,3,4-tetrahydrocyclopenta[b]indol-3-yl)acetic acid has an enantiomeric excess of about 99% or greater.

In some embodiments, after hydrolyzing in Step a), the (R)-2-(7-(4-cyclopentyl-3-(trifluoromethyl)benzyloxy)-1,2,3,4-tetrahydrocyclopenta[b]indol-3-yl)acetic acid is not isolated.

In some embodiments, after hydrolyzing in Step a), the (R)-2-(7-(4-cyclopentyl-3-(trifluoromethyl)benzyloxy)-1,2,3,4-tetrahydrocyclopenta[b]indol-3-yl)acetic acid is present in an amount of at least 40% as determined by HPLC. In some embodiments, after the hydrolyzing, the (R)-2-(7-(4-cyclopentyl-3-(trifluoromethyl)benzyloxy)-1,2,3,4-tetrahydrocyclopenta[b]indol-3-yl)acetic acid is present in an amount of at least 45% as determined by HPLC.

Step b)—Forming a First Mixture

In some embodiments, forming a first mixture in Step b) is conducted under an inert atmosphere. In some embodiments, forming a first mixture in Step b) is conducted under an inert atmosphere comprising argon or nitrogen. In some embodiments, forming a first mixture in Step b) is conducted under an inert atmosphere comprising nitrogen.

It is understood that forming a first mixture comprising L-arginine salt of (R)-2-(7-(4-cyclopentyl-3-(trifluoromethyl)benzyloxy)-1,2,3,4-tetrahydrocyclopenta[b]indol-3-yl)acetic acid, a water-miscible anti-solvent, and H$_2$O, may be performed in any manner routine to the skilled artisan.

By way of example, forming the first mixture may comprise forming the L-arginine salt by reacting L-arginine with (R)-2-(7-(4-cyclopentyl-3-(trifluoromethyl)benzyloxy)-1,2,3,4-tetrahydrocyclopenta[b]indol-3-yl)acetic acid; and mixing the L-arginine salt, the water-miscible anti-solvent, and H$_2$O.

By way of example, forming the first mixture may comprise forming a mixture of (R)-2-(7-(4-cyclopentyl-3-(trifluoromethyl)benzyloxy)-1,2,3,4-tetrahydrocyclopenta[b]indol-3-yl)acetic acid, the water-miscible anti-solvent and H$_2$O; and reacting the L-arginine with (R)-2-(7-(4-cyclopentyl-3-(trifluoromethyl)benzyloxy)-1,2,3,4-tetrahydrocyclopenta[b]indol-3-yl)acetic acid to form the first mixture.

By way of example, forming the first mixture may comprise forming a mixture of (R)-2-(7-(4-cyclopentyl-3-(trifluoromethyl)benzyloxy)-1,2,3,4-tetrahydrocyclopenta[b]indol-3-yl)acetic acid and the water-miscible anti-solvent; and reacting the L-arginine as an aqueous slurry or solution with (R)-2-(7-(4-cyclopentyl-3-(trifluoromethyl)benzyloxy)-1,2,3,4-tetrahydrocyclopenta[b]indol-3-yl)acetic acid to form the first mixture.

By way of example, forming the first mixture may comprise forming a mixture of (R)-2-(7-(4-cyclopentyl-3-(trifluoromethyl)benzyloxy)-1,2,3,4-tetrahydrocyclopenta[b]indol-3-yl)acetic acid, the water-miscible anti-solvent and the L-arginine; and adding H$_2$O to form the first mixture.

Accordingly, in some embodiments, forming the first mixture in Step b) comprises the step of adding L-arginine and H$_2$O, either together or separately in any order, to a salt-forming mixture comprising (R)-2-(7-(4-cyclopentyl-3-(trifluoromethyl)benzyloxy)-1,2,3,4-tetrahydrocyclopenta[b]indol-3-yl)acetic acid and the water-miscible anti-solvent to form the first mixture.

In some embodiments, the adding L-arginine and H$_2$O is conducted under an inert atmosphere.

In some embodiments, the adding L-arginine and H$_2$O is conducted under an inert atmosphere comprising argon or nitrogen. In some embodiments, the adding L-arginine and H$_2$O is conducted under an inert atmosphere comprising nitrogen.

In some embodiments, the water-miscible anti-solvent comprises a solvent selected from the group consisting of: acetonitrile, acetone, tetrahydrofuran, and $C_2$-$C_4$ alkanol. In some embodiments, the water-miscible anti-solvent comprises a solvent selected from the group consisting of: acetonitrile, acetone, tetrahydrofuran, ethanol, 1-propanol, 2-propanol, and 1-butanol. In some embodiments, the water-miscible anti-solvent comprises 2-propanol.

In some embodiments, prior to adding the L-arginine and H$_2$O, the salt-forming mixture comprises (R)-2-(7-(4-cyclopentyl-3-(trifluoromethyl)benzyloxy)-1,2,3,4-tetrahydrocyclopenta[b]indol-3-yl)acetic acid and 2-propanol in a weight ratio of about 1.0:3.0 to about 1.0:11.0.

In some embodiments, prior to adding the L-arginine and H$_2$O, the salt-forming mixture comprises (R)-2-(7-(4-cyclopentyl-3-(trifluoromethyl)benzyloxy)-1,2,3,4-tetrahydrocyclopenta[b]indol-3-yl)acetic acid and 2-propanol in a weight ratio of about 1.0:4.0 to about 1.0:10.0. In some embodiments, prior to adding the L-arginine and H$_2$O, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid and 2-propanol in a weight ratio of about 1.0:5.0 to about 1.0:9.0. In some embodiments, prior to adding the L-arginine and H$_2$O, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid and 2-propanol in a weight ratio of about 1.0:6.0 to about 1.0:8.0.

In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:0.8 to about 1.0:1.2.

In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:0.9 to about 1.0:1.2. In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:1.0 to about 1.0:1.2. In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:0.93 to about 1.0:1.01. In some embodiments, the molar ratio between (R)-2-(7-(4-cyclopentyl-3-

(trifluoromethyl)benzyloxy)-1,2,3,4-tetrahydrocyclopenta[b]indol-3-yl)acetic acid and L-arginine is about 1.0:0.93 to about 1.0:0.97. In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:1.0. In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:0.95.

In some embodiments, the weight ratio of L-arginine and $H_2O$ is about 1.0:0.4 to about 1.0:2.3. In some embodiments, the weight ratio of L-arginine and $H_2O$ is about 1.0:1.6 to about 1.0:2.1. In some embodiments, the weight ratio of L-arginine and $H_2O$ is about 1.0:0.8 to about 1.0:1.9. In some embodiments, the weight ratio of L-arginine and $H_2O$ is about 1.0:1.0 to about 1.0:1.7. In some embodiments, the weight ratio of L-arginine and $H_2O$ is about 1.0:1.1 to about 1.0:1.6. In some embodiments, the weight ratio of L-arginine and $H_2O$ is about 1.0:1.2 to about 1.0:1.5.

In some embodiments, the salt-forming mixture prior to the adding L-arginine is at a temperature of about 15° C. to about 83° C. In some embodiments, the salt-forming mixture prior to the adding L-arginine is at a temperature of about 18° C. to about 80° C. In some embodiments, the salt-forming mixture prior to the adding L-arginine is at a temperature of about 20° C. to about 40° C. In some embodiments, the salt-forming mixture prior to the adding L-arginine is at a temperature of about 18° C. to about 30° C.

In some embodiments, the adding L-arginine is conducted by adding L-arginine as an aqueous slurry to the salt-forming mixture.

In some embodiments, the adding L-arginine is conducted by adding L-arginine as a solid to the salt-forming mixture.

In some embodiments, the adding L-arginine to the salt-forming mixture is conducted by adding L-arginine as a solid to the salt-forming mixture substantially all at once. The phrase "substantially all at once" or "all at once" refers to the addition of all of the L-arginine to the salt-forming mixture at one time with the only limitation that is placed on the addition is by any limitation associated with the equipment used.

In some embodiments, the adding L-arginine to the salt-forming mixture is conducted by adding L-arginine as a solid to the salt-forming mixture over a period of about 30 minutes. In some embodiments, the adding L-arginine to the salt-forming mixture is conducted by adding L-arginine as a solid to the salt-forming mixture over a period of about 1 hour. In some embodiments, the adding L-arginine to the salt-forming mixture is conducted by adding L-arginine as a solid to the salt-forming mixture over a period of about 2 hours.

In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.0:3.0:0.05 to about 1.0:11.0:1.0. In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.0:4.0:0.1 to about 1.0:10.0:0.9. In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.0:5.0:0.15 to about 1.0:9.0:0.8. In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.0:6.0:0.25 to about 1.0:8.0:0.7.

In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.00:4.98:0.94 to about 1.00:7.46:1.40, about 1.00:5.29:0.99 to about 1.00:7.15:1.35, about 1.00:5.60:1.05 to about 1.00:6.84:1.29, about 1.00:5.72:1.08 to about 1.00:6.72:1.26, about 1.00:5.85:1.10 to about 1.00:6.59:1.24, about 1.00:5.97:1.12 to about 1.00:6.47:1.22, about 1.00:6.10:1.15 to about 1.00:6.34:1.19, or about 1.00:6.22:1.17.

In some embodiments, the salt-forming mixture during the adding L-arginine is at a temperature of about 15° C. to about 83° C. In some embodiments, the salt-forming mixture during the adding L-arginine is at a temperature of about 18° C. to about 80° C. In some embodiments, the salt-forming mixture during the adding L-arginine is at a temperature of about 20° C. to about 40° C. In some embodiments, the salt-forming mixture during the adding L-arginine is at a temperature of about 18° C. to about 30° C.

In some embodiments, the adding L-arginine is conducted by adding L-arginine as an aqueous solution to the salt-forming mixture.

In some embodiments, the adding L-arginine is conducted by adding L-arginine to the salt-forming mixture wherein L-arginine is a solution of about 2.1M to about 2.3M aqueous solution at a temperature of about 50° C. to about 75° C.

In some embodiments, forming the first mixture in Step b) is conducted at a stir rate of about 100 rpm to about 200 rpm. In some embodiments, forming the first mixture in Step b) is conducted at a stir rate of about 125 rpm to about 175 rpm. In some embodiments, forming the first mixture in Step b) is conducted at a stir rate of about 150 rpm.

Step c)—Heating the First Mixture to a First Heating Temperature to Form a Second Mixture In some embodiments, the first heating temperature is about 20° C. to about 85° C. In some embodiments, the first heating temperature is about 20° C. to about 83° C. In some embodiments, the first heating temperature is about 20° C. to about 55° C. In some embodiments, the first heating temperature is about 25° C. to about 45° C. In some embodiments, the first heating temperature is about 50° C. to about 83° C. In some embodiments, the first heating temperature is about 60° C. to about 80° C. In some embodiments, the first heating temperature is about 70° C. to about 80° C. In some embodiments, the first heating temperature is about 79° C. to about 85° C.

In some embodiments, an optional amount of $H_2O$ is added to the second mixture.

In some embodiments, when the optional amount of $H_2O$ is added to the second mixture, the weight amount of water added is about 0.4 to about 2.3 times the weight of L-arginine originally added in forming the first mixture.

In some embodiments, when the optional amount of $H_2O$ is added to the second mixture, the weight amount of water added is about 1.0:1.6 to about 1.0:2.1 times the weight of L-arginine originally added in forming the first mixture. In some embodiments, when water is added to the second mixture, the weight amount of water added is about 1.0:0.8 to about 1.0:1.9 times the weight of L-arginine originally added in forming the first mixture. In some embodiments, when water is added to the second mixture, the weight amount of water added is about 1.0:1.0 to about 1.0:1.7 times the weight of L-arginine originally added in forming the first mixture. In some embodiments, when water is added to the second mixture, the weight amount of water added is about 1.0:1.1 to about 1.0:1.6 times the weight of L-arginine originally added in forming the first mixture. In some embodiments, when water is added to the second mixture, the weight amount of water added is about 1.0:1.2 to about 1.0:1.5 times the weight of L-arginine originally added in forming the first mixture.

In some embodiments, the second mixture is substantially a homogeneous solution.

In some embodiments, Step c) is conducted at a stir rate of about 100 rpm to about 200 rpm. In some embodiments, Step c) is conducted at a stir rate of about 125 rpm to about 175 rpm. In some embodiments, Step c) is conducted at a stir rate of about 150 rpm.

Step d)—Adding a First Additional Amount of the Water-Miscible Anti-Solvent to the Second Mixture while Maintaining the First Heating Temperature to Form a Suspension In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:5.46 to about 1.00:8.20.

In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:4.70 to about 1.00:7.50. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:5.20 to about 1.00:7.00. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:5.70 to about 1.00:6.50. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:5.90 to about 1.00:6.30. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:5.95 to about 1.00:6.25. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:6.00 to about 1.00:6.20.

In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:5.46 to about 1.00:8.20, about 1.00:5.81 to about 1.00:7.86, about 1.00:6.15 to about 1.00:7.51, about 1.00:6.28 to about 1.00:7.38, about 1.00:6.42 to about 1.00:7.24, about 1.00:6.56 to about 1.00:7.10, about 1.00:6.69 to about 1.00:6.97, or about 1.00:6.83.

In some embodiments, the first additional amount of the water-miscible anti-solvent is added during a first time point and a second time point.

In some embodiments, about 5% to about 15% of the first additional amount of the water-miscible anti-solvent is added at the first time point.

In some embodiments, about 7% to about 13% of the first additional amount of the water-miscible anti-solvent is added at the first time point.

In some embodiments, about 8% to about 12% of the first additional amount of the water-miscible anti-solvent is added at the first time point. In some embodiments, about 9% to about 11% of the first additional amount of the water-miscible anti-solvent is added at the first time point.

In some embodiments, the first additional amount of the water-miscible anti-solvent is added at the first time point to form a cloudy mixture.

In some embodiments, prior to the second time point, a seed crystal of L-arginine salt of (R)-2-(7-(4-cyclopentyl-3-(trifluoromethyl)benzyloxy)-1,2,3,4-tetrahydrocyclopenta[b]indol-3-yl)acetic acid is optionally added.

In some embodiments, the first additional amount of the water-miscible anti-solvent is added at the second time point at a rate to complete the addition in about 1.00 hour or greater. In some embodiments, the first additional amount of the water-miscible anti-solvent is added at the second time point at a rate to complete the addition in about 1.00 hour to about 6.00 hours. In some embodiments, the first additional amount of the water-miscible anti-solvent is added at the second time point at a rate to complete the addition in about 1.00 hour to about 5.00 hours. In some embodiments, the first additional amount of the water-miscible anti-solvent is added at the second time point at a rate to complete the addition in about 1.00 hour to about 4.00 hours. In some embodiments, the first additional amount of the water-miscible anti-solvent is added at the second time point at a rate to complete the addition in about 1.00 hour to about 3.00 hours. In some embodiments, the first additional amount of the water-miscible anti-solvent is added at the second time point at a rate to complete the addition in about 1.00 hour to about 2.00 hours.

In some embodiments, the first heating temperature is maintained during the addition of the first additional amount of 2-propanol to the second mixture.

In some embodiments, Step d) is conducted at a stir rate of about 100 rpm to about 200 rpm. In some embodiments, Step d) is conducted at a stir rate of about 125 rpm to about 175 rpm. In some embodiments, Step d) is conducted at a stir rate of about 150 rpm.

Step e)—Cooling the Suspension to a First Cooling Temperature and Thereafter Heating to a Second Heating Temperature In some embodiments, cooling the suspension to the first cooling temperature in Step e) is conducted at a rate of about 8.80° C./hour to about 14.40° C./hour. In some embodiments, cooling the suspension to the first cooling temperature in Step e) is conducted at a rate of about 9.35° C./hour to about 13.80° C./hour. In some embodiments, cooling the suspension to the first cooling temperature in Step e) is conducted at a rate of about 9.90° C./hour to about 13.20° C./hour. In some embodiments, cooling the suspension to the first cooling temperature in Step e) is conducted at a rate of about 10.45° C./hour to about 12.60° C./hour. In some embodiments, cooling the suspension to the first cooling temperature in Step e) is conducted at a rate of about 10° C./hour to about 12° C./hour. In some embodiments, cooling the suspension to the first cooling temperature in Step e) is conducted at a rate of about 9° C./hour to about 11° C./hour.

In some embodiments, cooling the suspension to the first cooling temperature in Step e) is conducted at a rate of about 9.5° C./hour to about 10.5° C./hour.

In some embodiments, the first cooling temperature in Step e) is about 15° C. to about 40° C. In some embodiments, the first cooling temperature in Step e) is about 20° C. to about 30° C. In some embodiments, the first cooling temperature in Step e) is about 22° C. to about 24° C. In some embodiments, the first cooling temperature in Step e) is about 18° C. to about 22° C.

In some embodiments, the first cooling temperature is maintained for at least 1 hour prior to heating to the second heating temperature.

In some embodiments, the second heating temperature in Step e) is about 65° C. to about 83° C. In some embodiments, the second heating temperature in Step e) is about 70° C. to about 80° C. In some embodiments, the second heating temperature in Step e) is about 70° C. to about 75° C. In some embodiments, the second heating temperature in Step e) is about 69° C. to about 73° C.

In some embodiments, after heating to the second heating temperature, the second heating temperature is maintained for at least 30 minutes.

In some embodiments, Step e) is conducted at a stir rate of about 100 rpm to about 200 rpm. In some embodiments, Step e) is conducted at a stir rate of about 125 rpm to about 175 rpm. In some embodiments, Step e) is conducted at a stir rate of about 150 rpm.

Step f)—Cycling Step e) Optionally One or More Times

It is understood that when cycling Step e) more than once that the first cooling temperature at each cycle may be the same or different and said second heating temperature at each cycle may be the same or different.

Two Cycles

In some embodiments, the cycling in Step f) comprises the cycling Step e) two times.

In some embodiments, cycling Step e) two times comprises cooling the suspension to a first cycling cooling temperature, heating the suspension to a first cycling heating temperature, cooling the suspension to a second cycling cooling temperature, and heating the suspension to a second cycling heating temperature.

In some embodiments, the first cycling cooling temperature is about 16° C. to about 26° C., the first heating cycling temperature is about 55° C. to about 65° C., the second cycling cooling temperature is about 26° C. to about 36° C., and the second cycling heating temperature is about 45° C. to about 55° C. In some embodiments, the first cycling cooling temperature is about 19° C. to about 23° C., the first heating cycling temperature is about 58° C. to about 62° C., the second cycling cooling temperature is about 29° C. to about 33° C., and the second cycling heating temperature is about 48° C. to about 52° C.

In some embodiments, cooling to each cooling temperature is conducted at a substantially different cooling rate. In some embodiments, cooling to each cooling temperature is conducted at a different cooling rate.

In some embodiments, the cycling in Step f) comprises the cycling Step e) two times. In some embodiments, cooling to the first cycling cooling temperature is conducted at a rate of about 10.0° C./hour to about 15.0° C./hour. In some embodiments, cooling to the first cycling cooling temperature is conducted at a rate of about 11.0° C./hour to about 14.0° C./hour. In some embodiments, cooling to the first cycling cooling temperature is conducted at a rate of about 12.0° C./hour to about 13.0° C./hour. In some embodiments, cooling to the first cycling cooling temperature is conducted at a rate of about 12.5° C./hour.

In some embodiments, the cycling in Step f) comprises the cycling Step e) two times. In some embodiments, cooling to the second cycling cooling temperature is conducted at a rate of about 7.5° C./hour to about 12.5° C./hour. In some embodiments, cooling to the second cycling cooling temperature is conducted at a rate of about 8.5° C./hour to about 11.5° C./hour. In some embodiments, cooling to the second cycling cooling temperature is conducted at a rate of about 9.5° C./hour to about 10.5° C./hour. In some embodiments, cooling to the second cycling cooling temperature is conducted at a rate of about 10.0° C./hour.

Three Cycles

In some embodiments, the cycling in Step f) comprises the cycling Step e) three times.

In some embodiments, cycling Step e) three times comprises: cooling the suspension to a first cycling cooling temperature, heating the suspension to a first cycling heating temperature, cooling the suspension to a second cycling cooling temperature, heating the suspension to a second cycling heating temperature, cooling the suspension to a third cycling cooling temperature, and heating the suspension to a third cycling heating temperature.

In some embodiments, the first cycling cooling temperature is about 16° C. to about 26° C., the first heating cycling temperature is about 66° C. to about 76° C., the second cycling cooling temperature is about 16° C. to about 26° C., the second cycling heating temperature is about 55° C. to about 65° C., the third cycling cooling temperature is about 26° C. to about 36° C., and the third cycling heating temperature is about 45° C. to about 55° C. In some embodiments, the first cycling cooling temperature is about 19° C. to about 23° C., the first heating cycling temperature is about 69° C. to about 73° C., the second cycling cooling temperature is about 19° C. to about 23° C., the second cycling heating temperature is about 58° C. to about 62° C., the third cycling cooling temperature is about 29° C. to about 33° C., and the third cycling heating temperature is about 48° C. to about 52° C.

In some embodiments, cooling to each cooling temperature is conducted at a substantially different cooling rate. In some embodiments, cooling to each cooling temperature is conducted at a different cooling rate.

In some embodiments, cooling to the first cycling cooling temperature and the second cycling cooling temperature are each conducted at substantially the same cooling rate.

In some embodiments, the cycling in Step f) comprises the cycling Step e) three times. In some embodiments, cooling to the first cycling cooling temperature is conducted at a rate of about 10.0° C./hour to about 15.0° C./hour. In some embodiments, cooling to the first cycling cooling temperature is conducted at a rate of about 11.0° C./hour to about 14.0° C./hour. In some embodiments, cooling to the first cycling cooling temperature is conducted at a rate of about 12.0° C./hour to about 13.0° C./hour. In some embodiments, cooling to the first cycling cooling temperature is conducted at a rate of about 12.5° C./hour.

In some embodiments, the cycling in Step f) comprises the cycling Step e) three times. In some embodiments, cooling to the second cycling cooling temperature is conducted at a rate of about 10.0° C./hour to about 15.0° C./hour. In some embodiments, cooling to the second cycling cooling temperature is conducted at a rate of about 11.0° C./hour to about 14.0° C./hour. In some embodiments, cooling to the second cycling cooling temperature is conducted at a rate of about 12.0° C./hour to about 13.0° C./hour. In some embodiments, cooling to the first cycling cooling temperature is conducted at a rate of about 12.5° C./hour.

In some embodiments, the cycling in Step f) comprises the cycling Step e) three times. In some embodiments, cooling to the third cycling cooling temperature is conducted at a rate of about 7.5° C./hour to about 12.5° C./hour. In some embodiments, cooling to the third cycling cooling temperature is conducted at a rate of about 8.5° C./hour to about 11.5° C./hour. In some embodiments, cooling to the third cycling cooling temperature is conducted at a rate of about 9.5° C./hour to about 10.5° C./hour. In some embodiments, cooling to the second cycling cooling temperature is conducted at a rate of about 10.0° C./hour.

Four Cycles

In some embodiments, the cycling in Step f) comprises the cycling Step e) four times.

In some embodiments, cycling Step e) four times comprises: cooling the suspension to a first cycling cooling temperature, heating the suspension to a first cycling heating temperature, cooling the suspension to a second cycling cooling temperature, heating the suspension to a second cycling heating temperature, cooling the suspension to a third cycling cooling temperature, heating the suspension to a third cycling heating temperature, cooling the suspension to a fourth cycling cooling temperature, and heating the suspension to a fourth cycling heating temperature.

In some embodiments, the first cycling cooling temperature is about 16° C. to about 26° C., the first heating cycling temperature is about 66° C. to about 76° C., the second cycling cooling temperature is about 16° C. to about 26° C., the second cycling heating temperature is about 66° C. to about 76° C., the third cycling cooling temperature is about 16° C. to about 26° C., the third cycling heating temperature is about 55° C. to about 65° C., the fourth cycling cooling temperature is about 26° C. to about 36° C., and the fourth cycling heating temperature is about 45° C. to about 55° C. In some embodiments, the first cycling cooling temperature is about 19° C. to about 23° C., the first heating cycling temperature is about 69° C. to about 73° C., the second cycling cooling temperature is about 19° C. to about 23° C., the second cycling heating temperature is about 69° C. to about 73° C., the third cycling cooling temperature is about 19° C. to about 23° C., the third cycling heating temperature is about 58° C. to about 62° C., the fourth cycling cooling temperature is about 29° C. to about 33° C., and the fourth cycling heating temperature is about 48° C. to about 52° C.

In some embodiments, cooling to each cooling temperature is conducted at a substantially different cooling rate. In some embodiments, cooling to each cooling temperature is conducted at a different cooling rate.

In some embodiments, cooling to the first cycling cooling temperature, the second cycling cooling temperature, and the third cycling cooling temperature are each conducted at substantially the same cooling rate.

In some embodiments, the cycling in Step f) comprises the cycling Step e) four times. In some embodiments, cooling to the first cycling cooling temperature is conducted at a rate of about 10.0° C./hour to about 15.0° C./hour. In some embodiments, cooling to the first cycling cooling temperature is conducted at a rate of about 11.0° C./hour to about 14.0° C./hour. In some embodiments, cooling to the first cycling cooling temperature is conducted at a rate of about 12.0° C./hour to about 13.0° C./hour. In some embodiments, cooling to the first cycling cooling temperature is conducted at a rate of about 12.5° C./hour.

In some embodiments, the cycling in Step f) comprises the cycling Step e) four times. In some embodiments, cooling to the second cycling cooling temperature is conducted at a rate of about 10.0° C./hour to about 15.0° C./hour. In some embodiments, cooling to the second cycling cooling temperature is conducted at a rate of about 11.0° C./hour to about 14.0° C./hour. In some embodiments, cooling to the second cycling cooling temperature is conducted at a rate of about 12.0° C./hour to about 13.0° C./hour. In some embodiments, cooling to the first cycling cooling temperature is conducted at a rate of about 12.5° C./hour.

In some embodiments, the cycling in Step f) comprises the cycling Step e) four times. In some embodiments, cooling to the third cycling cooling temperature is conducted at a rate of about 10.0° C./hour to about 15.0° C./hour. In some embodiments, cooling to the third cycling cooling temperature is conducted at a rate of about 11.0° C./hour to about 14.0° C./hour. In some embodiments, cooling to the third cycling cooling temperature is conducted at a rate of about 12.0° C./hour to about 13.0° C./hour. In some embodiments, cooling to the first cycling cooling temperature is conducted at a rate of about 12.5° C./hour.

In some embodiments, the cycling in Step f) comprises the cycling Step e) four times. In some embodiments, cooling to the fourth cycling cooling temperature is conducted at a rate of about 7.5° C./hour to about 12.5° C./hour. In some embodiments, cooling to the fourth cycling cooling temperature is conducted at a rate of about 8.5° C./hour to about 11.5° C./hour. In some embodiments, cooling to the fourth cycling cooling temperature is conducted at a rate of about 9.5° C./hour to about 10.5° C./hour. In some embodiments, cooling to the second cycling cooling temperature is conducted at a rate of about 10.0° C./hour.

In some embodiments, Step f) is conducted at a stir rate of about 100 rpm to about 200 rpm. In some embodiments, Step f) is conducted at a stir rate of about 125 rpm to about 175 rpm. In some embodiments, Step f) is conducted at a stir rate of about 150 rpm.

Step g)—Cooling the Suspension to a Final Cooling Temperature to Form the Crystalline Free-Plate Habit of L-Arginine Salt of (R)-2-(7-(4-Cyclopentyl-3-(trifluoromethyl)benzyloxy)-1,2,3,4-tetrahydrocyclo-penta[b]indol-3-yl)acetic Acid In some embodiments, cooling the suspension in Step g) is conducted at a rate of about 7.5° C./hour to about 12.5° C./hour. In some embodiments, cooling the suspension in Step g) is conducted at a rate of about 8.5° C./hour to about 11.5° C./hour. In some embodiments, cooling the suspension in Step g) is conducted at a rate of about 9.5° C./hour to about 10.5° C./hour. In some embodiments, cooling the suspension in Step g) is conducted at a rate of about 10.0° C./hour.

In some embodiments, cooling the suspension in Step g) is conducted at a rate of about 8.8° C./hour to about 14.4° C./hour. In some embodiments, cooling the suspension in Step g) is conducted at a rate of about 9.4° C./hour to about 13.8° C./hour. In some embodiments, cooling the suspension in Step g) is conducted at a rate of about 9.9° C./hour to about 13.2° C./hour. In some embodiments, cooling the suspension in Step g) is conducted at a rate of about 10.5° C./hour to about 12.6° C./hour. In some embodiments, cooling the suspension in Step g) is conducted at a rate of about 10° C./hour to about 12° C./hour.

In some embodiments, after cooling in Step g) the temperature of the suspension is about 15° C. to about 40° C. In some embodiments, after cooling in Step g) the temperature of the suspension is about 20° C. to about 30° C. In some embodiments, after cooling in Step g) the temperature of the suspension is about 22° C. to about 24° C. In some embodiments, after cooling in Step g) the temperature of said suspension is about 18° C. to about 22° C.

In some embodiments, Step g) is conducted at a stir rate of about 100 rpm to about 200 rpm. In some embodiments, Step g) is conducted at a stir rate of about 125 rpm to about 175 rpm. In some embodiments, Step g) is conducted at a stir rate of about 150 rpm.

In some embodiments, the method further comprises the step of isolating the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid.

In some embodiments, the step of isolating comprises filtering the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid from the suspension. In some embodiments, the step of isolating comprises filtering the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid from the suspension and drying the crystalline free-plate habit of L-arginine salt at a reduced pressure.

In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has any one or more of the characteristics as described herein. For example, In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has an onset temperature of 205.0° C. to 208.5° C. as determined by differential scanning calorimetry at a scan rate of 10° C./minute. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has an onset temperature of 205.5° C. to 208.5° C. as determined by differential scanning calorimetry at a scan rate of 10° C./minute. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has an onset temperature of 206.5° C. to 208.5° C. as determined by differential scanning calorimetry at a scan rate of 10° C./minute. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has an onset temperature of 207.0° C. to 208.1° C. as determined by differential scanning calorimetry at a scan rate of 10° C./minute. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a differential scanning calorimetry trace conducted at a scan rate of 10° C./minute comprising an endotherm substantially as depicted in any one of FIGS. 6 to 10. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a differential scanning calorimetry trace conducted at a scan rate of 10° C./minute comprising an endotherm substantially as depicted in any one of FIGS. 6 to 10 and FIGS. 22 to 25. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a dynamic moisture sorption (DMS) profile with an adsorption phase from 30% RH to 90% RH wherein the crystalline free-plate habit gains about 0.3% weight or less at 90% RH. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a dynamic moisture sorption (DMS) profile with an adsorption phase from 30% RH to 90% RH wherein the crystalline free-plate habit gains about 0.2% weight or less at 90% RH. The DMS features reported herein can also vary by plus or minus about 0.15% weight change (i.e., ±0.15% weight change).

In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a total impurity profile by achiral HPLC of less than or equal to 0.5% by area. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a total impurity profile by achiral HPLC of less than or equal to 0.3% by area. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a total impurity profile by achiral HPLC of less than or equal to 0.2% by area.

In some embodiments, the method further comprises the step of formulating the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid to form a pharmaceutical composition.

In some embodiments, the method further comprises the step of admixing the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid with a pharmaceutical excipient to form a pharmaceutical composition.

In some embodiments, the method further comprises the step of admixing the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid with a pharmaceutical excipient to form a pharmaceutical composition suitable for oral, rectal, nasal, topical, buccal, sub-lingual, or vaginal, or in a form suitable for administration by inhalation, insufflation, or by a transdermal patch. In some embodiments, the pharmaceutical composition is suitable for oral administration.

Also described herein are methods for preparing a crystalline free-plate habit of the L-arginine salt of (R)-2-(7-(4-cyclopentyl-3-(trifluoromethyl)benzyloxy)-1,2,3,4-tetrahydrocyclo-penta[b]indol-3-yl)acetic acid starting from a different morphology, such as, but not limited to, spherulites/radial clusters, fine particles, agglomerates, flakes, or a mixture thereof.

Accordingly, one aspect of the present invention relates to methods for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid, the method comprising the steps of:

a) heating a first mixture comprising L-arginine salt of (R)-2-(7-(4-cyclopentyl-3-(trifluoromethyl)benzyloxy)-1,2,3,4-tetrahydrocyclopenta[b]indol-3-yl)acetic acid, a water-miscible anti-solvent, and water to a first heating temperature to form a second mixture;

b) cooling the second mixture to a first cooling temperature followed by adding a first additional amount of the water-miscible anti-solvent to the second mixture while maintaining the first cooling temperature and thereafter heating to a second heating temperature to form a suspension;

c) cycling Step b) optionally once or twice; and d) cooling the suspension to a second cooling temperature to form the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid.

In some embodiments, the water-miscible anti-solvent comprises a solvent selected from the group consisting of: acetonitrile, acetone, tetrahydrofuran, and $C_2$-$C_4$ alkanol. In some embodiments, the water-miscible anti-solvent comprises a solvent selected from the group consisting of: acetonitrile, acetone, tetrahydrofuran, ethanol, 1-propanol, 2-propanol, and 1-butanol. In some embodiments, the water-miscible anti-solvent comprises 2-propanol.

In some embodiments, the L-arginine salt of (R)-2-(7-(4-cyclopentyl-3-(trifluoromethyl)-benzyloxy)-1,2,3,4-tetrahydrocyclopenta[b]indol-3-yl)acetic acid in Step a) is a spherulite, a radial cluster, a fine particle, an agglomerate, a flake, or a mixture thereof.

In some embodiments, the L-arginine salt of (R)-2-(7-(4-cyclopentyl-3-(trifluoromethyl)-benzyloxy)-1,2,3,4-tetrahydrocyclopenta[b]indol-3-yl)acetic acid in Step a) is a crystalline spherulite habit or a mixture comprising a crystalline spherulite habit.

In some embodiments, the method for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid is conducted under an inert atmosphere. In some embodiments, the method is conducted under an inert atmosphere comprising nitrogen or argon. In some embodiments, the method is conducted under an inert atmosphere comprising nitrogen.

Step a)—Heating a First Mixture

In some embodiments, the first mixture comprises L-arginine salt of (R)-2-(7-(4-cyclopentyl-3-(trifluoromethyl)benzyloxy)-1,2,3,4-tetrahydrocyclopenta[b]indol-3-yl)acetic acid, 2-propanol, and water in a weight ratio of about 1.00:3.35:0.75 to about 1.00:5.03:1.13. In some embodiments, the first mixture comprises L-arginine salt of (R)-2-(7-(4-cyclopentyl-3-(trifluoromethyl)benzyloxy)-1,2,3,4-tetrahydrocyclopenta[b]indol-3-yl)acetic acid, 2-propanol, and water in a weight ratio of about 1.00:3.56:0.80 to about 1.00:4.82:1.08. In some embodiments, the first mixture comprises L-arginine salt of (R)-2-(7-(4-cyclopentyl-3-(trifluoromethyl)benzyloxy)-1,2,3,4-tetrahydrocyclopenta[b]indol-3-yl)acetic acid, 2-propanol, and water in a weight ratio of about 1.00:3.77:0.85 to about 1.00:4.61:1.03. In some embodiments, the first mixture comprises L-arginine salt of (R)-2-(7-(4-cyclopentyl-3-(trifluoromethyl)benzyloxy)-1,2,3,4-tetrahydrocyclopenta[b]indol-3-yl)acetic acid, 2-propanol, and water in a weight ratio of about 1.00:3.85:0.86 to about 1.00:4.52:1.02. In some embodiments, the first mixture comprises L-arginine salt of (R)-2-(7-(4-cyclopentyl-3-(trifluoromethyl)benzyloxy)-1,2,3,4-tetrahydrocyclopenta[b]indol-3-yl)acetic acid, 2-propanol, and water in a weight ratio of about 1.00:3.94:0.88 to about 1.00:4.44:1.00. In some embodiments, the first mixture comprises L-arginine salt of (R)-2-(7-(4-cyclopentyl-3-(trifluoromethyl)benzyloxy)-1,2,3,4-tetrahydrocyclopenta[b]indol-3-yl)acetic acid, 2-propanol, and water in a weight ratio of about 1.00:4.02:0.90 to about 1.00:4.36:0.98. In some embodiments, the first mixture comprises L-arginine salt of (R)-2-(7-(4-cyclopentyl-3-(trifluoromethyl)benzyloxy)-1,2,3,4-tetrahydrocyclopenta[b]indol-3-yl)acetic acid, 2-propanol, and water in a weight ratio of about 1.00:4.11:0.92 to about 1.00:4.27:0.96. In some embodiments, the first mixture comprises L-arginine salt of (R)-2-(7-(4-cyclopentyl-3-(trifluoromethyl)benzyloxy)-1,2,3,4-tetrahydrocyclopenta[b]indol-3-yl)acetic acid, 2-propanol, and water in a weight ratio of about 1.00:4.19:0.94.

In some embodiments, the first mixture is at a temperature of about 10° C. to about 30° C. prior to heating to the first heating temperature. In some embodiments, the first mixture is at a temperature of about 15° C. to about 25° C. prior to heating to the first heating temperature.

In some embodiments, the first heating temperature is about 60° C. to about 83° C. In some embodiments, the first heating temperature is about 70° C. to about 83° C. In some embodiments, the first heating temperature is about 75° C. to about 80° C.

In some embodiments, after heating to the first heating temperature the second mixture is substantially a homogeneous solution.

In some embodiments, Step a) is conducted at a stir rate of about 50 rpm to about 250 rpm. In some embodiments, Step a) is conducted at a stir rate of about 75 rpm to about 150 rpm.

Step b)—Cooling the Second Mixture to a First Cooling Temperature

In some embodiments, the first cooling temperature is about 50° C. to about 70° C. In some embodiments, the first cooling temperature is about 60° C. to about 70° C. In some embodiments, the first cooling temperature is about 63° C. to about 67° C.

In some embodiments, the first cooling temperature is maintained for at least 30 minutes.

In some embodiments, adding the first additional amount of 2-propanol to the second mixture is conducted at a rate of about 107.20 g/minute to about 160.80 g/minute. In some embodiments, adding the first additional amount of 2-propanol to the second mixture is conducted at a rate of about 113.90 g/minute to about 154.10 g/minute. In some embodiments, adding the first additional amount of 2-propanol to the second mixture is conducted at a rate of about 120.60 g/minute to about 147.40 g/minute. In some embodiments, adding the first additional amount of 2-propanol to the second mixture is conducted at a rate of about 127.30 g/minute to about 140.70 g/minute. In some embodiments, adding the first additional amount of 2-propanol to the second mixture is conducted at a rate of about 134 g/minute.

In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:0.98 to about 1.00:1.47. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:1.04 to about 1.00:1.41. In some embodiments, the weight ratio of L-arginine salt of (R)-2-(7-(4-cyclopentyl-3-(trifluoromethyl)benzyloxy)-1,2,3,4-tetrahydrocyclopenta[b]indol-3-yl)acetic acid to the first additional amount of 2-propanol is about 1.00:1.10 to about 1.00:1.35. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:1.13 to about 1.00:1.32. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:1.15 to about 1.00:1.30. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:1.18 to about 1.00:1.27. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:1.20 to about 1.00:1.25. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:1.23.

In some embodiments, after adding the first additional amount of 2-propanol, the first cooling temperature is maintained for at least 1 hour prior to heating to the second heating temperature.

In some embodiments, the second heating temperature is about 65° C. to about 83° C. In some embodiments, the second heating temperature is about 70° C. to about 80° C. In some embodiments, the second heating temperature is about 70° C. to about 75° C.

In some embodiments, the second heating temperature is at a temperature to retain the suspension.

In some embodiments, after heating to the second heating temperature, the second heating temperature is maintained for at least 30 minutes while retaining the suspension.

In some embodiments, Step b) is conducted at a stir rate of about 50 rpm to about 150 rpm. In some embodiments, Step b) is conducted at a stir rate of about 70 rpm to about 110 rpm.

Step c)—Cycling Step b)

In some embodiments, cycling Step b) is conducted once.
In some embodiments, cycling Step b) is conducted once, wherein the cycling conditions are substantially the same conditions as used for Step b).
In some embodiments, cycling Step b) is conducted once, wherein the cycling conditions are different from the conditions used for Step b); it is understood that the selected cycling conditions are still within the embodiments as described herein for Step b).
In some embodiments, cycling Step b) is conducted twice.
In some embodiments, cycling Step b) is conducted twice, wherein the cycling conditions for the first cycle and the second cycle are substantially the same conditions as used for Step b).
In some embodiments, cycling Step b) is conducted twice, wherein at least one of the conditions for the first cycle, the second cycle, or Step b) is different; it is understood that whether or not the first cycle and/or the second cycle is different from each other or one or both of the cycles are different from Step b) that each of selected conditions for the first cycle and the second cycle are still within the embodiments as described herein for Step b).

Step d)—Cooling the Suspension to a Second Cooling Temperature to Form the Crystalline Free-Plate Habit of L-Arginine Salt of (R)-2-(7-(4-Cyclopentyl-3-(trifluoro-methyl)benzyloxy)-1,2,3,4-tetrahydrocyclopenta[b]indol-3-yl)acetic Acid In some embodiments, the second cooling temperature is about 50° C. to about 70° C. In some embodiments, the second cooling temperature is about 60° C. to about 70° C. In some embodiments, the second cooling temperature is about 63° C. to about 67° C.

In some embodiments, the second cooling temperature is maintained for at least 30 minutes.

In some embodiments, Step d) is conducted at a stir rate of about 25 rpm to about 105 rpm. In some embodiments, Step d) is conducted at a stir rate of about 45 rpm to about 85 rpm.

In some embodiments, after cooling to the second cooling temperature, the method further comprises the step of cooling the suspension to a third cooling temperature.

In some embodiments, after cooling to the second cooling temperature, the method further comprises the step of cooling the suspension to a third cooling temperature of about 10° C. to about 30° C. In some embodiments, after cooling to the second cooling temperature, the method further comprises the step of cooling the suspension to a third cooling temperature of about 15° C. to about 25° C.

In some embodiments, the cooling rate from the second cooling temperature to the third cooling temperature is about 5° C. per hour to about 15° C. per hour. In some embodiments, the cooling rate from the second cooling temperature to the third cooling temperature is about 8° C. per hour to about 12° C. per hour. In some embodiments, the cooling rate from the second cooling temperature to the third cooling temperature is about 10° C. per hour.

In some embodiments, the method further comprises the step of isolating the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid.

In some embodiments, the step of isolating comprises filtering the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid from the suspension. In some embodiments, the step of isolating comprises filtering the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid from the suspension and drying the crystalline free-plate habit of L-arginine salt at a reduced pressure.

In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has an onset temperature of 205.0° C. to 208.5° C. as determined by differential scanning calorimetry at a scan rate of 10° C./minute. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has an onset temperature of 205.5° C. to 208.5° C. as determined by differential scanning calorimetry at a scan rate of 10° C./minute. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has an onset temperature of 206.5° C. to 208.5° C. as determined by differential scanning calorimetry at a scan rate of 10° C./minute. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has an onset temperature of 207.0° C. to 208.1° C. as determined by differential scanning calorimetry at a scan rate of 10° C./minute. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a differential scanning calorimetry trace conducted at a scan rate of 10° C./minute comprising an endotherm substantially as depicted in any one of FIGS. 6 to 10. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a differential scanning calorimetry trace conducted at a scan rate of 10° C./minute comprising an endotherm substantially as depicted in any one of FIGS. 6 to 10 and FIGS. 22 to 25. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a dynamic moisture sorption (DMS) profile with an adsorption phase from 30% RH to 90% RH wherein the crystalline free-plate habit gains about 0.3% weight or less at 90% RH. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a dynamic moisture sorption (DMS) profile with an adsorption phase from 30% RH to 90% RH wherein the crystalline free-plate habit gains about 0.2% weight or less at 90% RH. The DMS features reported herein can also vary by plus or minus about 0.15% weight change (i.e., f 0.15% weight change).

In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a total impurity profile by achiral HPLC of less than or equal to 0.5% by area. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a total impurity profile by achiral HPLC of less than or equal to 0.3% by area. In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has a total impurity profile by achiral HPLC of less than or equal to 0.2% by area.

In some embodiments, the method further comprises the step of formulating the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid to form a pharmaceutical composition.

In some embodiments, the method further comprises the step of admixing the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid with a pharmaceutical excipient to form a pharmaceutical composition.

One aspect of the present invention relates to methods for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid, the method comprising the steps of:

a) forming a first mixture comprising L-arginine salt of (R)-2-(7-(4-cyclopentyl-3-(trifluoromethyl)benzyloxy)-1,2,3,4-tetrahydrocyclopenta[b]indol-3-yl)acetic acid, a water-miscible anti-solvent, and H$_2$O;

b) heating the first mixture to a first heating temperature to form a second mixture;

c) adding a first additional amount of the water-miscible anti-solvent to the second mixture while maintaining the first heating temperature to form a suspension;

d) cooling the suspension to a first cooling temperature and thereafter heating to a second heating temperature;

e) cycling Step d) optionally one or more times, wherein the first cooling temperature at each cycle may be the same or different and the second heating temperature at each cycle may be the same or different; and f) cooling the suspension to a final cooling temperature to form the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid.

Step a)—Forming a First Mixture

In some embodiments, forming a first mixture in Step a) is conducted under an inert atmosphere. In some embodiments, forming a first mixture in Step a) is conducted under an inert atmosphere comprising argon or nitrogen. In some embodiments, forming a first mixture in Step a) is conducted under an inert atmosphere comprising nitrogen.

It is understood that forming a first mixture comprising L-arginine salt of (R)-2-(7-(4-cyclopentyl-3-(trifluoromethyl)benzyloxy)-1,2,3,4-tetrahydrocyclopenta[b]indol-3-yl)acetic acid, a water-miscible anti-solvent, and H$_2$O, may be performed in any manner routine to the skilled artisan, such as, the examples described supra.

In some embodiments, forming the first mixture in Step a) comprises the step of adding L-arginine and H$_2$O, either together or separately in any order, to a salt-forming mixture comprising (R)-2-(7-(4-cyclopentyl-3-(trifluoromethyl)benzyloxy)-1,2,3,4-tetrahydrocyclopenta[b]indol-3-yl)acetic acid and the water-miscible anti-solvent to form the first mixture.

In some embodiments, the adding L-arginine and H$_2$O is conducted under an inert atmosphere.

In some embodiments, the adding L-arginine and H$_2$O is conducted under an inert atmosphere comprising argon or nitrogen. In some embodiments, the adding L-arginine and H$_2$O is conducted under an inert atmosphere comprising nitrogen.

In some embodiments, the water-miscible anti-solvent comprises a solvent selected from the group consisting of: acetonitrile, acetone, tetrahydrofuran, and C$_2$-C$_4$ alkanol. In some embodiments, the water-miscible anti-solvent comprises a solvent selected from the group consisting of: acetonitrile, acetone, tetrahydrofuran, ethanol, 1-propanol, 2-propanol, and 1-butanol. In some embodiments, the water-miscible anti-solvent comprises 2-propanol.

In some embodiments, prior to adding the L-arginine and H$_2$O, the salt-forming mixture comprises (R)-2-(7-(4-cyclopentyl-3-(trifluoromethyl)benzyloxy)-1,2,3,4-tetrahydrocyclopenta[b]indol-3-yl)acetic acid and 2-propanol in a weight ratio of about 1.0:3.0 to about 1.0:11.0.

In some embodiments, prior to adding the L-arginine and H$_2$O, the salt-forming mixture comprises (R)-2-(7-(4-cyclopentyl-3-(trifluoromethyl)benzyloxy)-1,2,3,4-tetrahydrocyclopenta[b]indol-3-yl)acetic acid and 2-propanol in a weight ratio of about 1.0:4.0 to about 1.0:10.0. In some embodiments, prior to adding the L-arginine and H$_2$O, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid and 2-propanol in a weight ratio of about 1.0:5.0 to about 1.0:9.0. In some embodiments, prior to adding the L-arginine and H$_2$O, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid and 2-propanol in a weight ratio of about 1.0:6.0 to about 1.0:8.0.

In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:0.8 to about 1.0:1.2. In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:0.9 to about 1.0:1.2. In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:1.0 to about 1.0:1.2. In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:0.93 to about 1.0:1.01. In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:0.93 to about 1.0:0.97. In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:1.0. In some embodiments, the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:0.95.

In some embodiments, the weight ratio of L-arginine and H$_2$O is about 1.0:0.4 to about 1.0:2.3. In some embodiments, the weight ratio of L-arginine and H$_2$O is about 1.0:1.6 to about 1.0:2.1. In some embodiments, the weight ratio of L-arginine and H$_2$O is about 1.0:0.8 to about 1.0:1.9. In some embodiments, the weight ratio of L-arginine and H$_2$O is about 1.0:1.0 to about 1.0:1.7. In some embodiments, the weight ratio of L-arginine and H$_2$O is about 1.0:1.1 to about 1.0:1.6. In some embodiments, the weight ratio of L-arginine and H$_2$O is about 1.0:1.2 to about 1.0:1.5.

In some embodiments, the salt-forming mixture prior to the adding L-arginine is at a temperature of about 15° C. to about 83° C. In some embodiments, the salt-forming mixture prior to the adding L-arginine is at a temperature of about 18° C. to about 80° C. In some embodiments, the salt-forming mixture prior to the adding L-arginine is at a temperature of about 20° C. to about 40° C. In some embodiments, the salt-forming mixture prior to the adding L-arginine is at a temperature of about 18° C. to about 30° C.

In some embodiments, the adding L-arginine is conducted by adding L-arginine as an aqueous slurry to the salt-forming mixture.

In some embodiments, the adding L-arginine is conducted by adding L-arginine as a solid to the salt-forming mixture.

In some embodiments, the adding L-arginine to the salt-forming mixture is conducted by adding L-arginine as a solid to the salt-forming mixture substantially all at once. The phrase "substantially all at once" or "all at once" refers to the addition of all of the L-arginine to the salt-forming mixture at one time with the only limitation that is placed on the addition is by any limitation associated with the equipment used.

In some embodiments, the adding L-arginine to the salt-forming mixture is conducted by adding L-arginine as a solid to the salt-forming mixture over a period of about 30 minutes. In some embodiments, the adding L-arginine to the salt-forming mixture is conducted by adding L-arginine as a solid to the salt-forming mixture over a period of about 1 hour. In some embodiments, the adding L-arginine to the salt-forming mixture is conducted by adding L-arginine as a solid to the salt-forming mixture over a period of about 2 hours.

In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.0:3.0:0.05 to about 1.0:11.0:1.0. In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.0:4.0:0.1 to about 1.0:10.0:0.9. In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.0:5.0:0.15 to about 1.0:9.0:0.8. In some embodiments, the salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.0:6.0:0.25 to about 1.0:8.0:0.7.

In some embodiments, the salt-forming mixture during the adding L-arginine is at a temperature of about 15° C. to about 83° C. In some embodiments, the salt-forming mixture during the adding L-arginine is at a temperature of about 18° C. to about 80° C. In some embodiments, the salt-forming mixture during the adding L-arginine is at a temperature of about 20° C. to about 40° C. In some embodiments, the salt-forming mixture during the adding L-arginine is at a temperature of about 18° C. to about 30° C.

In some embodiments, the salt-forming mixture during the adding L-arginine is at a temperature of about 15° C. to about 83° C. In some embodiments, the salt-forming mixture during the adding L-arginine is at a temperature of about 18° C. to about 80° C. In some embodiments, the salt-forming mixture during the adding L-arginine is at a temperature of about 20° C. to about 40° C. In some embodiments, the salt-forming mixture during the adding L-arginine is at a temperature of about 18° C. to about 30° C.

In some embodiments, the adding L-arginine is conducted by adding L-arginine as an aqueous solution to the salt-forming mixture.

In some embodiments, the adding L-arginine is conducted by adding L-arginine to the salt-forming mixture wherein L-arginine is a solution of about 2.1M to about 2.3M aqueous solution at a temperature of about 50° C. to about 75° C.

In some embodiments, forming the first mixture in Step a) is conducted at a stir rate of about 100 rpm to about 200 rpm. In some embodiments, forming the first mixture in Step a) is conducted at a stir rate of about 125 rpm to about 175 rpm. In some embodiments, forming the first mixture in Step a) is conducted at a stir rate of about 150 rpm.

Step b)—Heating the First Mixture to a First Heating Temperature to Form a Second Mixture In some embodiments, the first heating temperature is about 20° C. to about 85° C. In some embodiments, the first heating temperature is about 20° C. to about 83° C. In some embodiments, the first heating temperature is about 20° C. to about 55° C. In some embodiments, the first heating temperature is about 25° C. to about 45° C. In some embodiments, the first heating temperature is about 50° C. to about 83° C. In some embodiments, the first heating temperature is about 60° C. to about 80° C. In some embodiments, the first heating temperature is about 70° C. to about 80° C. In some embodiments, the first heating temperature is about 79° C. to about 85° C.

In some embodiments, an optional amount of H$_2$O is added to the second mixture.

In some embodiments, when water is added to the second mixture, the weight amount of water added is about 0.4 to about 2.3 times the weight of L-arginine originally added in forming the first mixture.

In some embodiments, when water is added to the second mixture, the weight amount of water added is about 1.0:1.6 to about 1.0:2.1 times the weight of L-arginine originally added in forming the first mixture. In some embodiments, when water is added to the second mixture, the weight amount of water added is about 1.0:0.8 to about 1.0:1.9 times the weight of L-arginine originally added in forming the first mixture. In some embodiments, when water is added to the second mixture, the weight amount of water added is about 1.0:1.0 to about 1.0:1.7 times the weight of L-arginine originally added in forming the first mixture. In some embodiments, when water is added to the second mixture, the weight amount of water added is about 1.0:1.1 to about 1.0:1.6 times the weight of L-arginine originally added in forming the first mixture. In some embodiments, when water is added to the second mixture, the weight amount of water added is about 1.0:1.2 to about 1.0:1.5 times the weight of L-arginine originally added in forming the first mixture.

In some embodiments, the second mixture is substantially a homogeneous solution.

In some embodiments, Step b) is conducted at a stir rate of about 100 rpm to about 200 rpm. In some embodiments, Step b) is conducted at a stir rate of about 125 rpm to about 175 rpm. In some embodiments, Step b) is conducted at a stir rate of about 150 rpm.

Step c)—Adding a First Additional Amount of the Water-Miscible Anti-Solvent to the Second Mixture while Maintaining the First Heating Temperature to Form a Suspension In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:5.46 to about 1.00:8.20.

In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:4.70 to about 1.00:7.50. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:5.20 to about 1.00:7.00. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:5.70 to about 1.00:6.50. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:5.90 to about 1.00:6.30. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:5.95 to about 1.00:6.25. In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:6.00 to about 1.00:6.20.

In some embodiments, the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to the first additional amount of 2-propanol is about 1.00:5.46 to about 1.00:8.20, about 1.00:5.81 to about 1.00:7.86, about 1.00:6.15 to about 1.00:7.51, about 1.00:6.28 to about 1.00:7.38, about 1.00:6.42 to about 1.00:7.24, about 1.00:6.56 to about 1.00:7.10, about 1.00:6.69 to about 1.00:6.97, or about 1.00:6.83.

In some embodiments, the first additional amount of the water-miscible anti-solvent is added during a first time point and a second time point.

In some embodiments, about 5% to about 15% of the first additional amount of the water-miscible anti-solvent is added at the first time point. In some embodiments, about 7% to about 13% of the first additional amount of the water-miscible anti-solvent is added at the first time point. In some embodiments, about 8% to about 12% of the first additional amount of the water-miscible anti-solvent is added at the first time point. In some embodiments, about 9% to about 11% of the first additional amount of the water-miscible anti-solvent is added at the first time point.

In some embodiments, the first additional amount of the water-miscible anti-solvent is added at the first time point to form a cloudy mixture.

In some embodiments, prior to the second time point, a seed crystal of L-arginine salt of (R)-2-(7-(4-cyclopentyl-3-(trifluoromethyl)benzyloxy)-1,2,3,4-tetrahydrocyclopenta[b]indol-3-yl)acetic acid is optionally added.

In some embodiments, the first additional amount of the water-miscible anti-solvent is added at the second time point at a rate to complete the addition in about 1.00 hour or greater. In some embodiments, the first additional amount of the water-miscible anti-solvent is added at the second time point at a rate to complete the addition in about 1.00 hour to about 6.00 hours. In some embodiments, the first additional amount of the water-miscible anti-solvent is added at the second time point at a rate to complete the addition in about 1.00 hour to about 5.00 hours. In some embodiments, the first additional amount of the water-miscible anti-solvent is added at the second time point at a rate to complete the addition in about 1.00 hour to about 4.00 hours. In some embodiments, the first additional amount of the water-miscible anti-solvent is added at the second time point at a rate to complete the addition in about 1.00 hour to about 3.00 hours. In some embodiments, the first additional amount of the water-miscible anti-solvent is added at the second time point at a rate to complete the addition in about 1.00 hour to about 2.00 hours.

In some embodiments, the first heating temperature is maintained during the addition of the first additional amount of 2-propanol to the second mixture.

In some embodiments, Step c) is conducted at a stir rate of about 100 rpm to about 200 rpm. In some embodiments, Step c) is conducted at a stir rate of about 125 rpm to about 175 rpm. In some embodiments, Step c) is conducted at a stir rate of about 150 rpm.

Step d)—Cooling the Suspension to a First Cooling Temperature and Thereafter Heating to a Second Heating Temperature In some embodiments, cooling the suspension to the first cooling temperature in Step d) is conducted at a rate of about 8.80° C./hour to about 14.40° C./hour. In some embodiments, cooling the suspension to the first cooling temperature in Step d) is conducted at a rate of about 9.35° C./hour to about 13.80° C./hour. In some embodiments, cooling the suspension to the first cooling temperature in Step d) is conducted at a rate of about 9.90° C./hour to about 13.20° C./hour. In some embodiments, cooling the suspension to the first cooling temperature in Step d) is conducted at a rate of about 10.45° C./hour to about 12.60° C./hour. In some embodiments, cooling the suspension to the first cooling temperature in Step d) is conducted at a rate of about 10° C./hour to about 12° C./hour. In some embodiments, cooling the suspension to the first cooling temperature in Step d) is conducted at a rate of about 9° C./hour to about 11° C./hour. In some embodiments, cooling the suspension to the first cooling temperature in Step d) is conducted at a rate of about 9.5° C./hour to about 10.5° C./hour.

In some embodiments, the first cooling temperature in Step d) is about 15° C. to about 40° C. In some embodiments, the first cooling temperature in Step d) is about 20° C. to about 30° C. In some embodiments, the first cooling temperature in Step d) is about 22° C. to about 24° C. In some embodiments, the first cooling temperature in Step d) is about 18° C. to about 22° C.

In some embodiments, the first cooling temperature is maintained for at least 1 hour prior to heating to the second heating temperature.

In some embodiments, the second heating temperature in Step d) is about 65° C. to about 83° C. In some embodiments, the second heating temperature in Step d) is about 70° C. to about 80° C. In some embodiments, the second heating temperature in Step d) is about 70° C. to about 75° C. In some embodiments, the second heating temperature in Step d) is about 69° C. to about 73° C.

In some embodiments, after heating to the second heating temperature, the second heating temperature is maintained for at least 30 minutes.

In some embodiments, Step d) is conducted at a stir rate of about 100 rpm to about 200 rpm. In some embodiments, Step d) is conducted at a stir rate of about 125 rpm to about 175 rpm. In some embodiments, Step d) is conducted at a stir rate of about 150 rpm.

Step e)—Cycling Step d) Optionally One or More Times

It is understood that when cycling Step d) more than once that the first cooling temperature at each cycle may be the same or different and the second heating temperature at each cycle may be the same or different.

Two Cycles

In some embodiments, the cycling in Step e) comprises the cycling Step d) two times.

In some embodiments, cycling Step d) two times comprises cooling the suspension to a first cycling cooling temperature, heating the suspension to a first cycling heating temperature, cooling the suspension to a second cycling cooling temperature, and heating the suspension to a second cycling heating temperature.

In some embodiments, the first cycling cooling temperature is about 16° C. to about 26° C., the first heating cycling temperature is about 55° C. to about 65° C., the second cycling cooling temperature is about 26° C. to about 36° C., and the second cycling heating temperature is about 45° C. to about 55° C. In some embodiments, the first cycling cooling temperature is about 19° C. to about 23° C., the first heating cycling temperature is about 58° C. to about 62° C., the second cycling cooling temperature is about 29° C. to about 33° C., and the second cycling heating temperature is about 48° C. to about 52° C.

In some embodiments, cooling to each cooling temperature is conducted at a substantially different cooling rate. In some embodiments, cooling to each cooling temperature is conducted at a different cooling rate.

In some embodiments, the cycling in Step e) comprises the cycling Step d) two times. In some embodiments, cooling to the first cycling cooling temperature is conducted at a rate of about 10.0° C./hour to about 15.0° C./hour. In some embodiments, cooling to the first cycling cooling temperature is conducted at a rate of about 11.0° C./hour to about 14.0° C./hour. In some embodiments, cooling to the first cycling cooling temperature is conducted at a rate of about 12.0° C./hour to about 13.0° C./hour. In some embodiments, cooling to the first cycling cooling temperature is conducted at a rate of about 12.5° C./hour.

In some embodiments, the cycling in Step e) comprises the cycling Step d) two times. In some embodiments, cooling to the second cycling cooling temperature is conducted at a rate of about 7.5° C./hour to about 12.5° C./hour. In some embodiments, cooling to the second cycling cooling temperature is conducted at a rate of about 8.5° C./hour to about 11.5° C./hour. In some embodiments, cooling to the second cycling cooling temperature is conducted at a rate of about 9.5° C./hour to about 10.5° C./hour. In some embodiments, cooling to the second cycling cooling temperature is conducted at a rate of about 10.0° C./hour.

Three Cycles

In some embodiments, the cycling in Step e) comprises the cycling Step d) three times.

In some embodiments, cycling Step d) three times comprises: cooling the suspension to a first cycling cooling temperature, heating the suspension to a first cycling heating temperature, cooling the suspension to a second cycling cooling temperature, heating the suspension to a second cycling heating temperature, cooling the suspension to a third cycling cooling temperature, and heating the suspension to a third cycling heating temperature.

In some embodiments, the first cycling cooling temperature is about 16° C. to about 26° C., the first heating cycling temperature is about 66° C. to about 76° C., the second cycling cooling temperature is about 16° C. to about 26° C., the second cycling heating temperature is about 55° C. to about 65° C., the third cycling cooling temperature is about 26° C. to about 36° C., and the third cycling heating temperature is about 45° C. to about 55° C. In some embodiments, the first cycling cooling temperature is about 19° C. to about 23° C., the first heating cycling temperature is about 69° C. to about 73° C., the second cycling cooling temperature is about 19° C. to about 23° C., the second cycling heating temperature is about 58° C. to about 62° C., the third cycling cooling temperature is about 29° C. to about 33° C., and the third cycling heating temperature is about 48° C. to about 52° C.

In some embodiments, cooling to each cooling temperature is conducted at a substantially different cooling rate. In some embodiments, cooling to each cooling temperature is conducted at a different cooling rate.

In some embodiments, cooling to the first cycling cooling temperature and the second cycling cooling temperature are each conducted at substantially the same cooling rate.

In some embodiments, the cycling in Step e) comprises the cycling Step d) three times. In some embodiments, cooling to the first cycling cooling temperature is conducted at a rate of about 10.0° C./hour to about 15.0° C./hour. In some embodiments, cooling to the first cycling cooling temperature is conducted at a rate of about 11.0° C./hour to about 14.0° C./hour. In some embodiments, cooling to the first cycling cooling temperature is conducted at a rate of about 12.0° C./hour to about 13.0° C./hour. In some embodiments, cooling to the first cycling cooling temperature is conducted at a rate of about 12.5° C./hour.

In some embodiments, the cycling in Step e) comprises the cycling Step d) three times. In some embodiments, cooling to the second cycling cooling temperature is conducted at a rate of about 10.0° C./hour to about 15.0° C./hour. In some embodiments, cooling to the second cycling cooling temperature is conducted at a rate of about 11.0° C./hour to about 14.0° C./hour. In some embodiments, cooling to the second cycling cooling temperature is conducted at a rate of about 12.0° C./hour to about 13.0° C./hour. In some embodiments, cooling to the first cycling cooling temperature is conducted at a rate of about 12.5° C./hour.

In some embodiments, the cycling in Step e) comprises the cycling Step d) three times. In some embodiments, cooling to the third cycling cooling temperature is conducted at a rate of about 7.5° C./hour to about 12.5° C./hour. In some embodiments, cooling to the third cycling cooling temperature is conducted at a rate of about 8.5° C./hour to about 11.5° C./hour. In some embodiments, cooling to the third cycling cooling temperature is conducted at a rate of about 9.5° C./hour to about 10.5° C./hour. In some embodiments, cooling to the second cycling cooling temperature is conducted at a rate of about 10.0° C./hour.

Four Cycles

In some embodiments, the cycling in Step e) comprises the cycling Step d) four times.

In some embodiments, cycling Step d) four times comprises: cooling the suspension to a first cycling cooling temperature, heating the suspension to a first cycling heating temperature, cooling the suspension to a second cycling cooling temperature, heating the suspension to a second cycling heating temperature, cooling the suspension to a third cycling cooling temperature, heating the suspension to a third cycling heating temperature, cooling the suspension to a fourth cycling cooling temperature, and heating the suspension to a fourth cycling heating temperature.

In some embodiments, the first cycling cooling temperature is about 16° C. to about 26° C., the first heating cycling temperature is about 66° C. to about 76° C., the second cycling cooling temperature is about 16° C. to about 26° C., the second cycling heating temperature is about 66° C. to about 76° C., the third cycling cooling temperature is about 16° C. to about 26° C., the third cycling heating temperature is about 55° C. to about 65° C., the fourth cycling cooling temperature is about 26° C. to about 36° C., and the fourth cycling heating temperature is about 45° C. to about 55° C. In some embodiments, the first cycling cooling temperature is about 19° C. to about 23° C., the first heating cycling temperature is about 69° C. to about 73° C., the second cycling cooling temperature is about 19° C. to about 23° C., the second cycling heating temperature is about 69° C. to about 73° C., the third cycling cooling temperature is about 19° C. to about 23° C., the third cycling heating temperature is about 58° C. to about 62° C., the fourth cycling cooling temperature is about 29° C. to about 33° C., and the fourth cycling heating temperature is about 48° C. to about 52° C.

In some embodiments, cooling to each cooling temperature is conducted at a substantially different cooling rate. In some embodiments, cooling to each cooling temperature is conducted at a different cooling rate.

In some embodiments, cooling to the first cycling cooling temperature, the second cycling cooling temperature, and the third cycling cooling temperature are each conducted at substantially the same cooling rate.

In some embodiments, the cycling in Step e) comprises the cycling Step d) four times. In some embodiments, cooling to the first cycling cooling temperature is conducted at a rate of about 10.0° C./hour to about 15.0° C./hour. In some embodiments, cooling to the first cycling cooling temperature is conducted at a rate of about 11.0° C./hour to about 14.0° C./hour. In some embodiments, cooling to the first cycling cooling temperature is conducted at a rate of about 12.0° C./hour to about 13.0° C./hour. In some embodiments, cooling to the first cycling cooling temperature is conducted at a rate of about 12.5° C./hour.

In some embodiments, the cycling in Step e) comprises the cycling Step d) four times. In some embodiments, cooling to the second cycling cooling temperature is conducted at a rate of about 10.0° C./hour to about 15.0° C./hour. In some embodiments, cooling to the second cycling cooling temperature is conducted at a rate of about 11.0° C./hour to about 14.0° C./hour. In some embodiments, cooling to the second cycling cooling temperature is conducted at a rate of about 12.0° C./hour to about 13.0° C./hour. In some embodiments, cooling to the first cycling cooling temperature is conducted at a rate of about 12.5° C./hour.

In some embodiments, the cycling in Step e) comprises the cycling Step d) four times. In some embodiments, cooling to the third cycling cooling temperature is conducted at a rate of about 10.0° C./hour to about 15.0° C./hour. In some embodiments, cooling to the third cycling cooling temperature is conducted at a rate of about 11.0° C./hour to about 14.0° C./hour. In some embodiments, cooling to the third cycling cooling temperature is conducted at a rate of about 12.0° C./hour to about 13.0° C./hour. In some embodiments, cooling to the first cycling cooling temperature is conducted at a rate of about 12.5° C./hour.

In some embodiments, the cycling in Step e) comprises the cycling Step d) four times. In some embodiments, cooling to the fourth cycling cooling temperature is conducted at a rate of about 7.5° C./hour to about 12.5° C./hour. In some embodiments, cooling to the fourth cycling cooling temperature is conducted at a rate of about 8.5° C./hour to about 11.5° C./hour. In some embodiments, cooling to the fourth cycling cooling temperature is conducted at a rate of about 9.5° C./hour to about 10.5° C./hour. In some embodiments, cooling to the second cycling cooling temperature is conducted at a rate of about 10.0° C./hour.

In some embodiments, Step e) is conducted at a stir rate of about 100 rpm to about 200 rpm. In some embodiments, Step e) is conducted at a stir rate of about 125 rpm to about 175 rpm. In some embodiments, Step e) is conducted at a stir rate of about 150 rpm.

Step f)—Cooling the Suspension to a Final Cooling Temperature to Form the Crystalline Free-Plate Habit of L-Arginine Salt of (R)-2-(7-(4-Cyclopentyl-3-(trifluoromethyl)benzyloxy)-1,2,3,4-tetrahydrocyclo-penta[b]indol-3-yl)acetic Acid In some embodiments, cooling the suspension in Step f) is conducted at a rate of about 7.5° C./hour to about 12.5° C./hour. In some embodiments, cooling the suspension in Step f) is conducted at a rate of about 8.5° C./hour to about 11.5° C./hour. In some embodiments, cooling the suspension in Step f) is conducted at a rate of about 9.5° C./hour to about 10.5° C./hour. In some embodiments, cooling the suspension in Step f) is conducted at a rate of about 10.0° C./hour.

In some embodiments, cooling the suspension in Step f) is conducted at a rate of about 8.8° C./hour to about 14.4° C./hour. In some embodiments, cooling the suspension in Step f) is conducted at a rate of about 9.4° C./hour to about 13.8° C./hour. In some embodiments, cooling the suspension in Step f) is conducted at a rate of about 9.9° C./hour to about 13.2° C./hour. In some embodiments, cooling the suspension in Step f) is conducted at a rate of about 10.5° C./hour to about 12.6° C./hour. In some embodiments, cooling the suspension in Step f) is conducted at a rate of about 10° C./hour to about 12° C./hour.

In some embodiments, after cooling in Step f) the temperature of the suspension is about 15° C. to about 40° C. In some embodiments, after cooling in Step f) the temperature of the suspension is about 20° C. to about 30° C. In some embodiments, after cooling in Step f) the temperature of the suspension is about 22° C. to about 24° C. In some embodiments, after cooling in Step f) the temperature of said suspension is about 18° C. to about 22° C.

In some embodiments, Step f) is conducted at a stir rate of about 100 rpm to about 200 rpm. In some embodiments, Step f) is conducted at a stir rate of about 125 rpm to about 175 rpm. In some embodiments, Step f) is conducted at a stir rate of about 150 rpm.

In some embodiments, the method further comprises the step of isolating the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid.

In some embodiments, the step of isolating comprises filtering the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid from the suspension. In some embodiments, the step of isolating comprises filtering the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid from the suspension and drying the crystalline free-plate habit of L-arginine salt at a reduced pressure.

In some embodiments, after filtering, the crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid has any one or more of the characteristics as described herein.

Another aspect of the present invention relates to pharmaceutical compositions prepared according to any of the methods as described herein.

Another aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid prepared according to any of the methods as described herein.

A composition comprising a crystalline free-plate habit of L-arginine salt of (R)-2-(7-(4-cyclopentyl-3-(trifluorom-ethyl)benzyloxy)-1,2,3,4-tetrahydrocyclo-penta[b]indol-3-yl)acetic acid prepared according to any of the methods as described herein.

A pharmaceutical composition comprising a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid prepared according to any of the methods as described herein and a pharmaceutical excipient.

In some embodiments, the pharmaceutical composition is suitable for oral, rectal, nasal, topical, buccal, sub-lingual, or vaginal, or in a form suitable for administration by inhalation, insufflation, or by a transdermal patch. In some embodiments, the pharmaceutical composition is suitable for oral administration.

Crystalline Plate Habit or Morphology

Figure 5A:
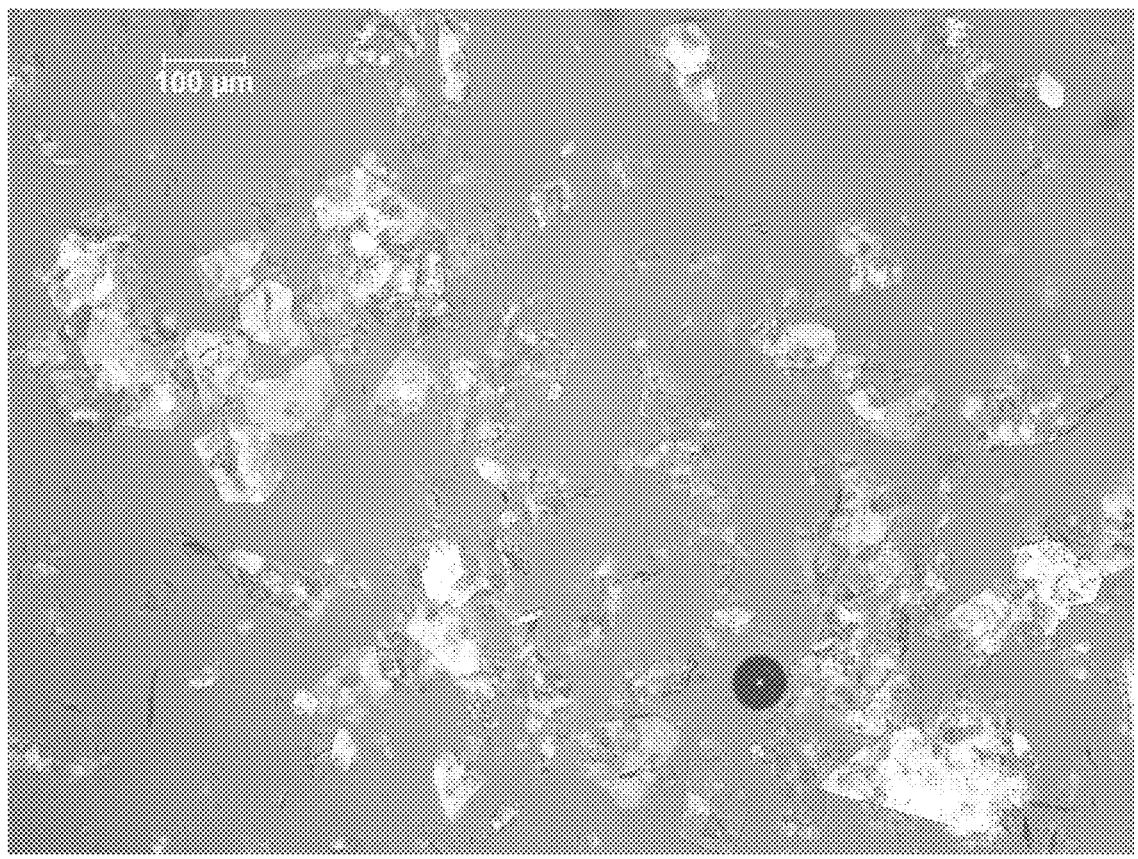
FIG. 5A shows a micrograph of the crystal plate morphology as described in Example 3 using polarized light microscopy (PLM).
Figure 5B:
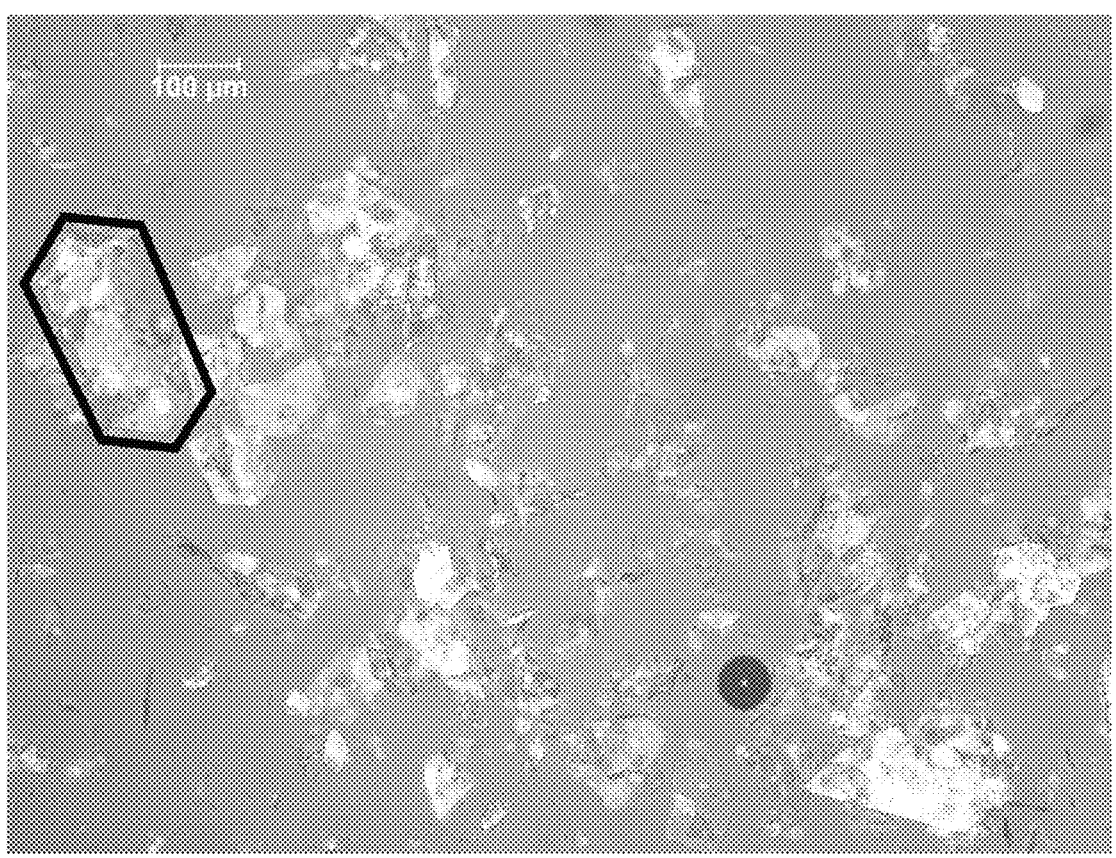
FIG. 5B shows the same micrograph as in FIG. 5A of the crystal plate morphology as described in Example 3 using polarized light microscopy (PLM) but also includes an added outline of a substantially intact/complete free-plate having an elongated hexagonal shape.
Figure 19:
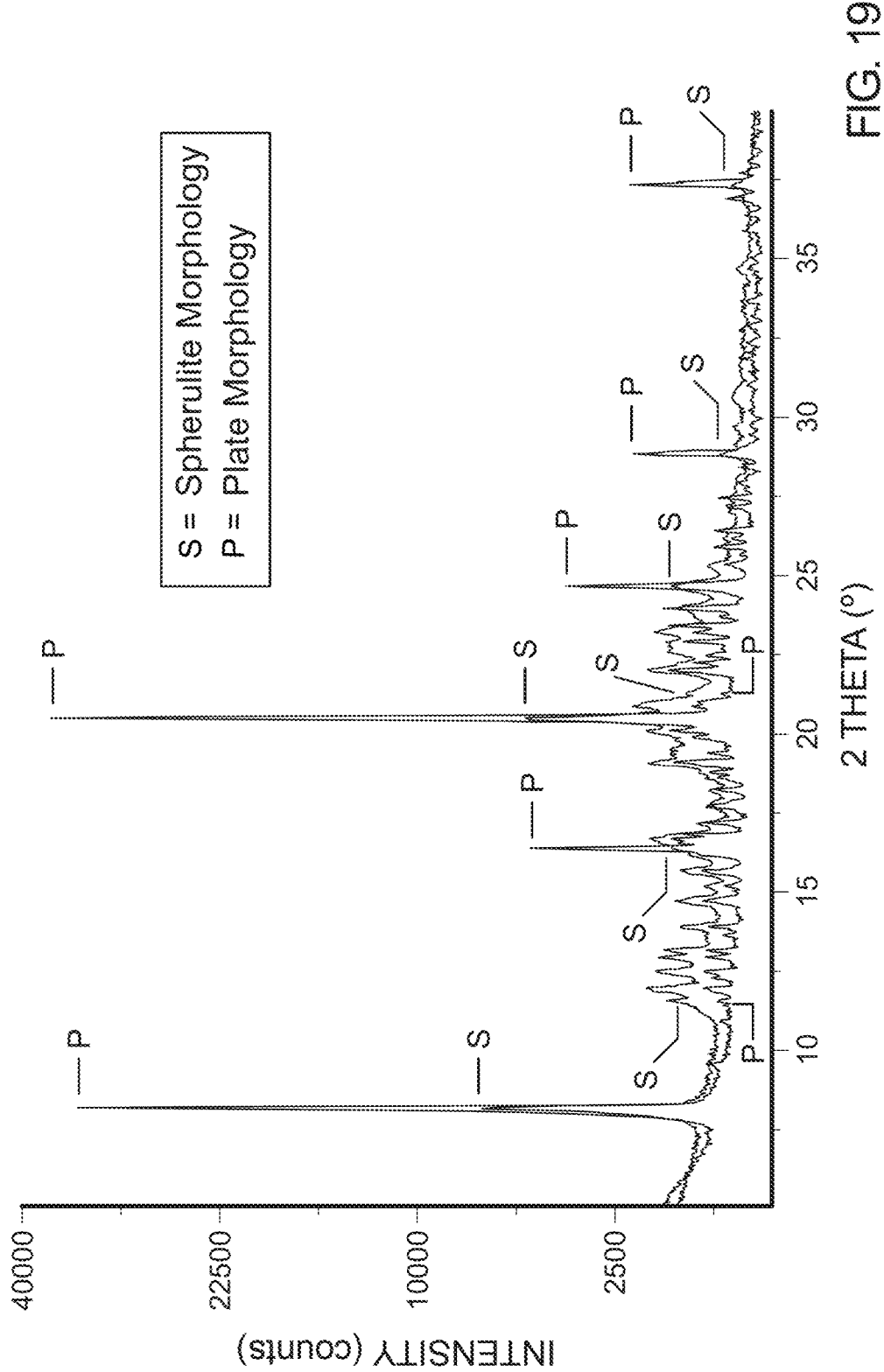
FIG. 19 shows a PXRD Pattern overlay for the L-arginine salt of Compound 1 showing the peak intensity differences between Lot A2 (plates) and Lot H2 (spherulites) indicating a higher degree of crystallinity for the plates compared to the spherulites. Also shown is the lower sample-related background scatter (i.e., a lower amorphous halo contribution) for the Lot A2 (plates).

The present invention is directed, inter alia, to a crystalline free-plate habit or morphology and processes useful in the preparation of a crystalline free-plate habit of L-arginine salt of (R)-2-(7-(4-cyclopentyl-3-(trifluoromethyl)-benzyloxy)-1,2,3,4-tetrahydrocyclopenta[b]indol-3-yl)acetic acid. The plates were discovered from the novel synthetic methods as described herein and were shown to be thin hexagonal-like plates with two opposite sides of the plate being longer that the other sides (i.e., elongated hexagonal plate). However, due to the thin characteristic of the plates, a complete unbroken plate is rarely seen. Instead, what is generally observed are large to small broken pieces of the thin hexagonal-like plates. FIG. 5B shows a copy of FIG. 5A that has been modified to add an outline to highlight the substantially intact/complete free-plate with an elongated hexagonal shape. It is understood by those skilled in the art that microscopy is one of the more useful techniques to distinguish two crystalline habits or morphologies. This is particularly useful when 2 or more morphologies are associated with the same or substantially the same crystal phase as is the case with the L-arginine salt of Compound 1. Comparing the PXRD patterns of the habit prepared previously (i.e., WO2011/094008 and Example 2 infra) and the plate habit prepared as described herein (i.e., see FIG. 19, PXRD overlay between spherulites and plates) it was observed that the two PXRD patterns were the same or substantially the same, thus the two habits represent the same crystal phase. Although the two habits revealed the same or substantially the same PXRD pattern, a higher degree of crystallinity was observed for the plate habit as indicated in FIG. 19 by substantially higher peak intensities and yet lower sample-related background scatter (i.e., a lower amorphous halo contribution). Since sample size and sample preparation can affect peak intensities and sample-related background scatter, and since the two habits share the same crystal phase, PXRD may not be considered the most appropriate test method to distinguish between two habits. However, PXRD does allow for determining whether two habits have the same crystal phase or different crystal phases. For determining different habits, microscopy is one of the more useful methods. Accordingly, the skilled person would be capable of reviewing a micrograph for a crystal habit prepared by the processes described herein and readily acknowledge that the crystal habit was a free-plate or pieces resulting from a broken free-plate and not some other habit, such as, what was prepared previously in the art. Similarly, by simple inspection of two micrographs, such as FIG. 1 (spherulites) and FIG. 5A (free-plates), one can readily confirm they are different habits.

In addition to the techniques described herein, specific surface can also be used to characterize the free-plates of the present invention. Accordingly, the specific surface area values disclosed in the present invention have been obtained by means of a specific surface area analysis technique based on the BET (Brunauer, Emmett and Teller) theory, which is a well-accepted theory known in the art for the calculation of surface areas of solids by means of measuring their physical adsorption of gas molecules (see: Brunauer, S.; Emmett, P. H.; and Teller, E.; *J. Am. Chem. Soc.*, 1938, 60, 309). In particular, the specific surface area values measured in the present invention have been calculated from the BET surface area plot obtained by measuring the quantity of nitrogen gas molecules adsorbed by a weighted amount of solid at different relative pressures ($P/P_0$) within the range 0.05-0.3 ($P/P_0$), at 77.3 K. The measurement of the adsorption of gas molecules was carried out by means of a Micromeritics™ TriStar II BET surface analyzer having the characteristics as set out below in Example 14. Namely, nitrogen gas was used for the adsorption measurement. The sample for each analysis was degassed at 25° C. for 960 minutes under vacuum (i.e., 100 mm/Hg). The determination of the adsorption of nitrogen was measured at 77.3 K at eleven relative pressures ($P/P_0$) sufficiently dispersed within the range of about 0.05 to about 0.30 (i.e. eleven absolute pressures in the range of about 36 mm Hg to about 223 mm Hg relative to the saturated pressure at the time of measurement that ranged from about 738 mmHg to about 743 mmHg).

One aspect of the present invention relates to a novel crystalline plate morphology of L-arginine salt of (R)-2-(7-(4-cyclopentyl-3-(trifluoromethyl)benzyloxy)-1,2,3,4-tetrahydrocyclo-penta[b]indol-3-yl)acetic acid as described herein.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclo-penta[b]indol-3-yl)acetic acid.

In some embodiments, the crystalline free-plate habit has a powder X-ray diffraction pattern comprising peaks, in terms of 2θ, at 8.2°±0.2°, 16.4°±0.2°, and 20.5°±0.2°. In some embodiments, the crystalline free-plate habit has a powder X-ray diffraction pattern comprising peaks, in terms of 2θ, at 8.2°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, and 28.8°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, 28.8°±0.2°, and 37.3°±0.2°.

In some embodiments, the crystalline free-plate habit has a differential scanning calorimetry trace comprising an endotherm with an extrapolated onset temperature of 205.0° C. to 208.5° C. at a scan rate of 10° C./minute. In some embodiments, the crystalline free-plate habit has a differential scanning calorimetry trace comprising an endotherm with an extrapolated onset temperature of 205.0° C. to 208.1° C. at a scan rate of 10° C./minute. In some embodiments, the crystalline free-plate habit has a differential scanning calorimetry trace comprising an endotherm with an extrapolated onset temperature of 205.5° C. to 208.5° C. at a scan rate of 10° C./minute. In some embodiments, the crystalline free-plate habit has a differential scanning calorimetry trace comprising an endotherm with an extrapolated onset temperature of 206.0° C. to 208.5° C. at a scan rate of 10° C./minute. In some embodiments, the crystalline free-plate habit has a differential scanning calorimetry trace comprising an endotherm with an extrapolated onset temperature of 206.5° C. to 208.5° C. at a scan rate of 10° C./minute. In some embodiments, the crystalline free-plate habit has a differential scanning calorimetry trace comprising an endotherm with an extrapolated onset temperature of 205.5° C. to 208.1° C. at a scan rate of 10° C./minute.

In some embodiments, the crystalline free-plate habit has a differential scanning calorimetry trace comprising an endotherm with an extrapolated onset temperature of 206.5° C. to 208.1° C. at a scan rate of 10° C./minute. In some embodiments, the crystalline free-plate habit has a differential scanning calorimetry trace comprising an endotherm with an extrapolated onset temperature of 207.0° C. to 208.1° C. at a scan rate of 10° C./minute. In some embodiments, the crystalline free-plate habit has a differential scanning calorimetry trace conducted at a scan rate of 10° C./minute comprising an endotherm substantially as depicted in any one of FIGS. 6 to 10. In some embodiments, the crystalline free-plate habit has a differential scanning calorimetry trace conducted at a scan rate of 10° C./minute comprising an endotherm substantially as depicted in any one of FIGS. 6 to 10 and FIGS. 22 to 25.

In some embodiments, the crystalline free-plate habit has a dynamic moisture sorption (DMS) profile with an adsorption phase from 30% RH to 90% RH wherein the crystalline free-plate habit gains about 0.3% weight or less at 90% RH. In some embodiments, the crystalline free-plate habit has a dynamic moisture sorption (DMS) profile with an adsorption phase from 30% RH to 90% RH wherein the crystalline free-plate habit gains about 0.2% weight or less at 90% RH.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclo-penta[b]indol-3-yl)acetic acid having a BET specific surface area of about 0.05 m$^2$/g, about 0.1 m$^2$/g, about 0.15 m$^2$/g, about 0.2 m$^2$/g, about 0.25 m$^2$/g, about 0.3 m$^2$/g, about 0.35 m$^2$/g, about 0.4 m$^2$/g, about 0.45 m$^2$/g, about 0.5 m$^2$/g, about 0.55 m$^2$/g, about 0.6 m$^2$/g, about 0.65 m$^2$/g, or about 0.7 m$^2$/g to about 2.0 m$^2$/g, about 2.5 m$^2$/g, about 3.0 m$^2$/g, about 3.5 m$^2$/g, about 4.0 m$^2$/g, about 4.5 m$^2$/g, about 5.0 m$^2$/g, about 5.5 m$^2$/g, about 6.0 m$^2$/g, about 6.5 m$^2$/g, about 7.0 m$^2$/g, about 7.5 m$^2$/g, about 8.0 m$^2$/g, about 8.5 m$^2$/g, about 9.0 m$^2$/g, or about 9.5 m$^2$/g.

In some embodiments, the crystalline free-plate habit has a BET specific surface area of about 0.1 m$^2$/g to about 5.0 m$^2$/g. In some embodiments, the crystalline free-plate habit has a BET specific surface area of about 0.1 m$^2$/g to about 4.0 m$^2$/g. In some embodiments, the crystalline free-plate habit has a BET specific surface area of about 0.3 m$^2$/g to about 4.0 m$^2$/g. In some embodiments, the crystalline free-plate habit has a BET specific surface area of about 0.5 m$^2$/g to about 4.0 m$^2$/g. In some embodiments, the crystalline free-plate habit has a BET specific surface area of about 0.6 m$^2$/g to about 4.0 m$^2$/g. In some embodiments, the crystalline free-plate habit has a BET specific surface area of about 0.3 m$^2$/g to about 3.0 m$^2$/g. In some embodiments, the crystalline free-plate habit has a BET specific surface area of about 0.4 m$^2$/g to about 2.0 m$^2$/g. In some embodiments, the crystalline free-plate habit has a BET specific surface area of about 0.5 m$^2$/g to about 1.8 m$^2$/g. In some embodiments, the crystalline free-plate habit has a BET specific surface area of about 0.6 m$^2$/g to about 1.6 m$^2$/g.

In some embodiments, the crystalline free-plate habit has:
1) a powder X-ray diffraction pattern comprising peaks, in terms of 2θ, at 8.2°±0.2°, 16.4°±0.2°, 20.5°±0.2°, 24.6°±0.2°, 28.8°±0.2°, and 37.3°±0.2°;
2) a differential scanning calorimetry trace comprising an endotherm with an extrapolated onset temperature of 205.0° C. to 208.5° C. at a scan rate of 10° C./minute; and/or
3) a dynamic moisture sorption (DMS) profile with an adsorption phase from 30% RH to 90% RH wherein the crystalline free-plate habit gains about 0.3% weight or less at 90% RH.

In some embodiments, the crystalline free-plate habit has:
1) a powder X-ray diffraction pattern comprising peaks, in terms of 2θ, at 8.2°±0.2°, 16.4°±0.2°, 20.5°±0.2°, and 24.6°±0.2°;
2) a differential scanning calorimetry trace comprising an endotherm with an extrapolated onset temperature of 206.5° C. to t 208.5° C. at a scan rate of 10° C./minute; and/or 3) a dynamic moisture sorption (DMS) profile with an adsorption phase from 30% RH to 90% RH wherein the crystalline free-plate habit gains about 0.3% weight or less at 90% RH.

In some embodiments, the crystalline free-plate habit has:
1) a powder X-ray diffraction pattern comprising peaks, in terms of 2θ, at 8.2°±0.2°, 20.5°±0.2°, and 24.6°±0.2°;
2) a differential scanning calorimetry trace comprising an endotherm with an extrapolated onset temperature of 205.5° C. to 208.5° C. at a scan rate of 10° C./minute; and/or
3) a dynamic moisture sorption (DMS) profile with an adsorption phase from 30% RH to 90% RH wherein the crystalline free-plate habit gains about 0.2% weight or less at 90% RH.

In some embodiments, the crystalline free-plate habit has:
1) a powder X-ray diffraction pattern comprising peaks, in terms of 2θ, at 8.2°±0.2°, 16.4°±0.2°, and 20.5°±0.2°;
2) a differential scanning calorimetry trace comprising an endotherm with an extrapolated onset temperature of 207.1° C. to 208.1° C. at a scan rate of 10° C./minute; and/or
3) a dynamic moisture sorption (DMS) profile with an adsorption phase from 30% RH to 90% RH wherein the crystalline free-plate habit gains about 0.2% weight or less at 90% RH.

In some embodiments, the crystalline free-plate habit has:
1) a differential scanning calorimetry trace comprising an endotherm with an extrapolated onset temperature of 205.0° C. to 208.5° C. at a scan rate of 10° C./minute; and/or
2) a dynamic moisture sorption (DMS) profile with an adsorption phase from 30% RH to 90% RH wherein the crystalline free-plate habit gains about 0.3% weight or less at 90% RH.

In some embodiments, the crystalline free-plate habit has:
1) a differential scanning calorimetry trace comprising an endotherm with an extrapolated onset temperature of 206.5° C. to t 208.5° C. at a scan rate of 10° C./minute; and/or 2) a dynamic moisture sorption (DMS) profile with an adsorption phase from 30% RH to 90% RH wherein the crystalline free-plate habit gains about 0.3% weight or less at 90% RH.

In some embodiments, the crystalline free-plate habit has:
1) a differential scanning calorimetry trace comprising an endotherm with an extrapolated onset temperature of 205.5° C. to 208.5° C. at a scan rate of 10° C./minute; and/or
2) a dynamic moisture sorption (DMS) profile with an adsorption phase from 30% RH to 90% RH wherein the crystalline free-plate habit gains about 0.2% weight or less at 90% RH.

In some embodiments, the crystalline free-plate habit has:
1) a differential scanning calorimetry trace comprising an endotherm with an extrapolated onset temperature of 207.1° C. to 208.1° C. at a scan rate of 10° C./minute; and/or
2) a dynamic moisture sorption (DMS) profile with an adsorption phase from 30% RH to 90% RH wherein the crystalline free-plate habit gains about 0.2% weight or less at 90% RH. In some embodiments, the crystalline free-plate habit has:
1) a powder X-ray diffraction pattern comprising peaks, in terms of 2θ, at 8.2°±0.2°, 16.4°±0.2°, and 20.5°±0.2°;
2) a differential scanning calorimetry trace comprising an endotherm with an extrapolated onset temperature of 205.0° C. to 208.5° C. at a scan rate of 10° C./minute;
3) a dynamic moisture sorption (DMS) profile with an adsorption phase from 30% RH to 90% RH wherein said crystalline free-plate habit gains about 0.3% weight or less at 90% RH; and/or
4) a BET specific surface area of about 0.1 m²/g to about 5.0 m²/g.

In some embodiments, the crystalline free-plate habit has:
1) a powder X-ray diffraction pattern comprising peaks, in terms of 2θ, at 8.2°±0.2°, 20.5°±0.2°, and 24.6°±0.2°;
2) a differential scanning calorimetry trace comprising an endotherm with an extrapolated onset temperature of 205.5° C. to t 208.5° C. at a scan rate of 10° C./minute;
3) a dynamic moisture sorption (DMS) profile with an adsorption phase from 30% RH to 90% RH wherein said crystalline free-plate habit gains about 0.3% weight or less at 90% RH; and/or 4) a BET specific surface area of about 0.1 m²/g to about 4.0 m²/g.

In some embodiments, the crystalline free-plate habit has:
1) a powder X-ray diffraction pattern comprising peaks, in terms of 2θ, at 8.2°±0.2°, 20.5°±0.2°, and 24.6°±0.2°;
2) a differential scanning calorimetry trace comprising an endotherm with an extrapolated onset temperature of 205.5° C. to t 208.5° C. at a scan rate of 10° C./minute;
3) a dynamic moisture sorption (DMS) profile with an adsorption phase from 30% RH to 90% RH wherein said crystalline free-plate habit gains about 0.3% weight or less at 90% RH; and/or 4) a BET specific surface area of about 0.3 m²/g to about 3.0 m²/g.

In some embodiments, the crystalline free-plate habit has:
1) a powder X-ray diffraction pattern comprising peaks, in terms of 2θ, at 8.2°±0.2°, 16.4°±0.2°, 20.5°±0.2°, and 24.6°±0.2°;
2) a differential scanning calorimetry trace comprising an endotherm with an extrapolated onset temperature of 205.5° C. to 208.5° C. at a scan rate of 10° C./minute;
3) a dynamic moisture sorption (DMS) profile with an adsorption phase from 30% RH to 90% RH wherein said crystalline free-plate habit gains about 0.3% weight or less at 90% RH; and/or
4) a BET specific surface area of about 0.6 m²/g to about 4.0 m²/g.

In some embodiments, the crystalline free-plate habit has:
1) a powder X-ray diffraction pattern comprising peaks, in terms of 2θ, at 8.2°±0.2°, 16.4°±0.2°, 20.5°±0.2°, and 24.6°±0.2°;
2) a differential scanning calorimetry trace comprising an endotherm with an extrapolated onset temperature of 206.5° C. to t 208.5° C. at a scan rate of 10° C./minute;

3) a dynamic moisture sorption (DMS) profile with an adsorption phase from 30% RH to 90% RH wherein said crystalline free-plate habit gains about 0.3% weight or less at 90% RH; and/or
4) a BET specific surface area of about 0.4 m²/g to about 2.0 m²/g.

In some embodiments, the crystalline free-plate habit has:
1) a powder X-ray diffraction pattern comprising peaks, in terms of 2θ, at 8.2°±0.2°, 16.4°±0.2°, 20.5°±0.2°, 24.6°±0.2°, and 28.8°±0.2°;
2) a differential scanning calorimetry trace comprising an endotherm with an extrapolated onset temperature of 206.5° C. to 208.1° C. at a scan rate of 10° C./minute;
3) a dynamic moisture sorption (DMS) profile with an adsorption phase from 30% RH to 90% RH wherein said crystalline free-plate habit gains about 0.2% weight or less at 90% RH; and/or
4) a BET specific surface area of about 0.5 m²/g to about 1.8 m²/g.

In some embodiments, the crystalline free-plate habit has:
1) a powder X-ray diffraction pattern comprising peaks, in terms of 2θ, at 8.2°±0.2°, 16.4°±0.2°, 20.5°±0.2°, 24.6°±0.2°, 28.8°±0.2°, and 37.3°±0.2°;
2) a differential scanning calorimetry trace comprising an endotherm with an extrapolated onset temperature of 205.5° C. to 208.1° C. at a scan rate of 10° C./minute;
3) a dynamic moisture sorption (DMS) profile with an adsorption phase from 30% RH to 90% RH wherein said crystalline free-plate habit gains about 0.2% weight or less at 90% RH; and/or
4) a BET specific surface area of about 0.6 m2/g to about 4.0 m2/g.

In some embodiments, the crystalline free-plate habit has:
1) a powder X-ray diffraction pattern comprising peaks, in terms of 2θ, at 8.2°±0.2°, 16.4°±0.2°, 20.5°±0.2°, 24.6°±0.2°, 28.8°±0.2°, and 37.3°±0.2°;
2) a differential scanning calorimetry trace comprising an endotherm with an extrapolated onset temperature of 207.1° C. to 208.1° C. at a scan rate of 10° C./minute;
3) a dynamic moisture sorption (DMS) profile with an adsorption phase from 30% RH to 90% RH wherein said crystalline free-plate habit gains about 0.2% weight or less at 90% RH; and/or
4) a BET specific surface area of about 0.6 m²/g to about 1.6 m²/g.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid having a powder X-ray diffraction pattern comprising peaks, in terms of 2θ, at 8.2°±0.2°, 16.4°±0.2°, and 20.5°±0.2°. In some embodiments, the crystalline free-plate habit has a powder X-ray diffraction pattern comprising peaks, in terms of 2θ, at 8.2°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, and 28.8°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, 28.8°±0.2°, and 37.3°±0.2°.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid having a differential scanning calorimetry trace comprising an endotherm with an extrapolated onset temperature of 205.0° C. to 208.5° C. when scanned at 10° C. per minute. In some embodiments, the crystalline free-plate habit has a differential scanning calorimetry trace comprising an endotherm with an extrapolated onset temperature of 205.0° C. to 208.1° C. at a scan rate of 10° C./minute. In some embodiments, the crystalline free-plate habit has a differential scanning calorimetry trace comprising an endotherm with an extrapolated onset temperature of 205.5° C. to 208.5° C. at a scan rate of 10° C./minute. In some embodiments, the crystalline free-plate habit has a differential scanning calorimetry trace comprising an endotherm with an extrapolated onset temperature of 205.5° C. to 208.1° C. at a scan rate of 10° C./minute. In some embodiments, the crystalline free-plate habit has a differential scanning calorimetry trace comprising an endotherm with an extrapolated onset temperature of 206.0° C. to 208.5° C. at a scan rate of 10° C./minute. In some embodiments, the crystalline free-plate habit has a differential scanning calorimetry trace comprising an endotherm with an extrapolated onset temperature of 206.5° C. to 208.5° C. at a scan rate of 10° C./minute. In some embodiments, the crystalline free-plate habit has a differential scanning calorimetry trace comprising an endotherm with an extrapolated onset temperature of 206.5° C. to 208.1° C. at a scan rate of 10° C./minute. In some embodiments, the crystalline free-plate habit has a differential scanning calorimetry trace comprising an endotherm with an extrapolated onset temperature of 207.0° C. to 208.1° C. at a scan rate of 10° C./minute. In some embodiments, the crystalline free-plate habit has a differential scanning calorimetry trace conducted at a scan rate of 10° C./minute comprising an endotherm substantially as depicted in any one of FIGS. 6 to 10. In some embodiments, the crystalline free-plate habit has a differential scanning calorimetry trace conducted at a scan rate of 10° C./minute comprising an endotherm substantially as depicted in any one of FIGS. 6 to 10 and FIGS. 22 to 25. In some embodiments, the crystalline free-plate habit has a powder X-ray diffraction pattern comprising peaks, in terms of 2θ, at 8.2°±0.2°, 16.4°±0.2°, and 20.5°±0.2°. In some embodiments, the crystalline free-plate habit has a powder X-ray diffraction pattern comprising peaks, in terms of 2θ, at 8.2°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, and 28.8°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, 28.8°±0.2°, and 37.3°±0.2°.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid having a dynamic moisture sorption (DMS) profile with an adsorption phase from 30% RH to 90% RH wherein the crystalline free-plate habit gains about 0.3% weight or less at 90% RH. In some embodiments, the crystalline free-plate habit has a dynamic moisture sorption (DMS) profile with an adsorption phase from 30% RH to 90% RH wherein the crystalline free-plate habit gains about 0.2% weight or less at 90% RH. In some embodiments, the crystalline free-plate habit has a powder X-ray diffraction pattern comprising peaks, in terms of 2θ, at 8.2°±0.2°, 16.4°±0.2°, and 20.5°±0.2°. In some embodiments, the crystalline free-plate habit has a powder X-ray diffraction pattern comprising peaks, in terms of 2θ, at 8.2°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, and 28.8°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, 28.8°±0.2°, and 37.3°±0.2°.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid having a BET specific surface area of about 0.1 m$^2$/g to about 5.0 m$^2$/g. In some embodiments, the crystalline free-plate habit has a BET specific surface area of about 0.1 m$^2$/g to about 4.0 m$^2$/g. In some embodiments, the crystalline free-plate habit has a BET specific surface area of about 0.3 m$^2$/g to about 4.0 m$^2$/g. In some embodiments, the crystalline free-plate habit has a BET specific surface area of about 0.5 m$^2$/g to about 4.0 m$^2$/g. In some embodiments, the crystalline free-plate habit has a BET specific surface area of about 0.6 m$^2$/g to about 4.0 m$^2$/g. In some embodiments, the crystalline free-plate habit has a BET specific surface area of about 0.3 m$^2$/g to about 3.0 m$^2$/g. In some embodiments, the crystalline free-plate habit has a BET specific surface area of about 0.4 m$^2$/g to about 2.0 m$^2$/g. In some embodiments, the crystalline free-plate habit has a BET specific surface area of about 0.5 m$^2$/g to about 1.8 m$^2$/g. In some embodiments, the crystalline free-plate habit has a BET specific surface area of about 0.6 m$^2$/g to about 1.6 m$^2$/g. In some embodiments, the crystalline free-plate habit has a powder X-ray diffraction pattern comprising peaks, in terms of 2θ, at 8.2°±0.2°, 16.4°±0.2°, and 20.5°±0.2°. In some embodiments, the crystalline free-plate habit has a powder X-ray diffraction pattern comprising peaks, in terms of 2θ, at 8.2°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, and 28.8°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, 28.8°±0.2°, and 37.3°±0.2°.

Indications

S1P receptor agonists having agonist activity on the S1P$_1$ receptor have been shown to rapidly and reversibly induce lymphopenia (also referred to as peripheral lymphocyte lowering (PLL); Hale et al., Bioorg. Med. Chem. Lett., 14:3351-3355, 2004). This is attended by clinically useful immunosuppression by virtue of sequestering T- and B-cells in secondary lymphoid tissue (lymph nodes and Peyer's patches) and thus apart from sites of inflammation and organ grafts (Rosen et al., Immunol. Rev., 195:160-177, 2003; Schwab et al., Nature Immunol., 8:1295-1301, 2007). This lymphocyte sequestration, for example in lymph nodes, is thought to be a consequence of concurrent agonist-driven functional antagonism of the S1P$_1$ receptor on T-cells (whereby the ability of S1P to mobilize T-cell egress from lymph nodes is reduced) and persistent agonism of the S1P$_1$ receptor on lymph node endothelium (such that barrier function opposing transmigration of lymphocytes is increased) (Matloubian et al., Nature, 427:355-360, 2004; Baumruker et al., Expert Opin. Investig. Drugs, 16:283-289, 2007). It has been reported that agonism of the S1P$_1$ receptor alone is sufficient to achieve lymphocyte sequestration (Sanna et al., J Biol Chem., 279:13839-13848, 2004) and that this occurs without impairment of immune responses to systemic infection (Brinkmann et al., Transplantation, 72:764-769, 2001; Brinkmann et al., Transplant Proc., 33:530-531, 2001).

That agonism of endothelial S1P$_1$ receptors has a broader role in promoting vascular integrity is supported by work implicating the S1P$_1$ receptor in capillary integrity in mouse skin and lung (Sanna et al., Nat Chem Biol., 2:434-441, 2006). Vascular integrity can be compromised by inflammatory processes, for example as may derive from sepsis, major trauma and surgery so as to lead to acute lung injury or respiratory distress syndrome (Johan Groeneveld, Vascul. Pharmacol., 39:247-256, 2003).

An exemplary S1P receptor agonist having agonist activity on the S1P$_1$ receptor is FTY720, an immunosuppressive agent (Martini et al., Expert Opin. Investig. Drugs, 16:505-518, 2007) that was approved by the FDA as Gilenya® (fingolimod) in September 2010 for the treatment of relapsing multiple sclerosis. FTY720 acts as a prodrug which is phosphorylated in vivo; the phosphorylated derivative is an agonist for S1P$_1$, S1P$_3$, S1P$_4$, and S1P$_5$ receptors (but not the S1P$_2$ receptor) (Chiba, Pharmacology & Therapeutics, 108: 308-319, 2005). FTY720 has been shown to rapidly and reversibly induce lymphopenia (also referred to as peripheral lymphocyte lowering (PLL); Hale et al., Bioorg. Med. Chem. Lett., 14:3351-3355, 2004). This is attended by clinically useful immunosuppression by virtue of sequestering T- and B-cells in secondary lymphoid tissue (lymph nodes and Peyer's patches) and thus apart from sites of inflammation and organ grafts (Rosen et al., Immunol. Rev., 195:160-177, 2003; Schwab et al., Nature Immunol., 8:1295-1301, 2007).

FTY720 has been reported to have therapeutic efficacy in at least: a rat model for autoimmune myocarditis and a mouse model for acute viral myocarditis (Kiyabayashi et al., J. Cardiovasc. Pharmacol., 35:410-416, 2000; Miyamoto et al., J. Am. Coll. Cardiol., 37:1713-1718, 2001); mouse models for inflammatory bowel disease including colitis (Mizushima et al., Inflamm. Bowel Dis., 10:182-192, 2004; Deguchi et al., Oncology Reports, 16:699-703, 2006; Fujii et al., Am. J. Physiol. Gastrointest. Liver Physiol., 291:G267-G274, 2006; Daniel et al., J. Immunol., 178:2458-2468, 2007); a rat model for progressive mesangioproliferative glomerulonephritis (Martini et al., Am. J. Physiol. Renal Physiol., 292:F1761-F1770, 2007); a mouse model for asthma, suggested to be primarily through the S1P$_1$ receptor on the basis of work using the S1P$_1$ receptor agonist SEW2871 (Idzko et al, J. Clin. Invest., 116:2935-2944, 2006); a mouse model for airway inflammation and induction of bronchial hyperresponsiveness (Sawicka et al., J. Immunol., 171; 6206-6214, 2003); a mouse model for atopic dermatitis (Kohno et al., Biol. Pharm. Bull., 27:1392-1396, 2004); a mouse model for ischemia-reperfusion injury (Kaudel et al., Transplant. Proc, 39:499-502, 2007); a mouse model for systemic lupus erythematosus (SLE) (Okazaki et al., J. Rheumatol., 29:707-716, 2002; Herzinger et al, Am. J. Clin. Dermatol., 8:329-336, 2007); rat models for rheumatoid arthritis (Matsuura et al., Int. J. Immunopharmacol., 22:323-331, 2000; Matsuura et al., *Inflamm. Res.*, 49:404-410, 2000); a rat model for autoimmune uveitis (Kurose et al., *Exp. Eye Res.*, 70:7-15, 2000); mouse models for type I diabetes (Fu et al, *Transplantation*, 73:1425-1430, 2002; Maki et al., *Transplantation*, 74:1684-1686, 2002; Yang et al., *Clinical Immunology*, 107:30-35, 2003; Maki et al., *Transplantation*, 79:1051-1055, 2005); mouse models for atherosclerosis (Nofer et al., *Circulation*, 115:501-508, 2007; Keul et al., *Arterioscler. Thromb. Vasc. Biol.*, 27:607-613, 2007); a rat model for brain inflammatory reaction following traumatic brain injury (TBI) (Zhang et al., *J. Cell. Mol. Med*, 11:307-314, 2007); and mouse models for graft coronary artery disease and graft-versus-host disease (GVHD) (Hwang et al., *Circulation*, 100:1322-1329, 1999; Taylor et al., *Blood*, 110:3480-3488, 2007). In vitro results suggest that FTY720 may have therapeutic efficacy for β-amyloid-related inflammatory diseases including Alzheimer's disease (Kaneider et al., *FASEB J.*, 18:309-311, 2004). KRP-203, an S1P receptor agonist having agonist activity on the $S1P_1$ receptor, has been reported to have therapeutic efficacy in a rat model for autoimmune myocarditis (Ogawa et al., *BBRC*, 361:621-628, 2007). Using the $S1P_1$ receptor agonist SEW2871, it has been shown that agonism of endothelial $S1P_1$ receptors prevents proinflammatory monocyte/endothelial interactions in type I diabetic vascular endothelium (Whetzel et al., *Circ. Res.*, 99:731-739, 2006) and protects the vasculature against TNFα-mediated monocyte/endothelial interactions (Bolick et al., *Arterioscler. Thromb. Vasc. Biol.*, 25:976-981, 2005).

Additionally, FTY720 has been reported to have therapeutic efficacy in experimental autoimmune encephalomyelitis (EAE) in rats and mice, a model for human multiple sclerosis (Brinkmann et al., *J. Biol. Chem.*, 277:21453-21457, 2002; Fujino et al., *J. Pharmacol. Exp. Ther.*, 305: 70-77, 2003; Webb et al., *J. Neuroimmunol.*, 153:108-121, 2004; Rausch et al., *J. Magn. Reson. Imaging*, 20:16-24, 2004; Kataoka et al., *Cellular & Molecular Immunology*, 2:439-448, 2005; Brinkmann et al., *Pharmacology & Therapeutics*, 115:84-105, 2007; Baumruker et al., *Expert Opin. Investig. Drugs*, 16:283-289, 2007; Balatoni et al., *Brain Research Bulletin*, 74:307-316, 2007). Furthermore, FTY720 has been found to have therapeutic efficacy for multiple sclerosis in clinical trials. In Phase II clinical trials for relapsing-remitting multiple sclerosis, FTY720 was found to reduce the number of lesions detected by magnetic resonance imaging (MRI) and clinical disease activity in patients with multiple sclerosis (Kappos et al., *N. Engl. J. Med*, 355:1124-1140, 2006; Martini et al., *Expert Opin. Investig. Drugs*, 16:505-518, 2007; Zhang et al., *Mini-Reviews in Medicinal Chemistry*, 7:845-850, 2007; Brinkmann, *Pharmacology & Therapeutics*, 115:84-105, 2007). FTY720 is currently in Phase III studies of remitting-relapsing multiple sclerosis (Brinkmann, *Pharmacology & Therapeutics*, 115:84-105, 2007; Baumruker et al., *Expert. Opin. Investig. Drugs*, 16:283-289, 2007; Dev et al., *Pharmacology and Therapeutics*, 117:77-93, 2008).

FTY720 has also been reported to have anti-viral activity. Specific data has been presented in the lymphocytic choriomeningitis virus (LCMV) mouse model, wherein the mice were infected with either the Armstrong or the clone 13 strain of LCMV (Premenko-Lanier et al., *Nature*, 454, 894, 2008).

FTY720 has also been reported to impair migration of dendritic cells infected with *Francisella tularensis* to the mediastinal lymph node, thereby reducing the bacterial colonization of it. *Francisella tularensis* is associated with tularemia, ulceroglandular infection, respiratory infection and a typhoidal disease (E. Bar-Haim et al., PLoS Pathog 4(11): e1000211. doi:10.1371/journal.ppat.1000211, 2008).

It has also been reported that a short-term high dose of FTY720 rapidly reduced ocular infiltrates in experimental autoimmune uveoretinitis. When given in the early stages of ocular inflammation, FTY720 rapidly prevented retinal damage. It was reported to not only prevent infiltration of target organs, but also reduce existing infiltration (Raveney et al., *Arch. Ophthalmol.* 126(10), 1390, 2008).

It has been reported that treatment with FTY720 relieved ovariectomy-induced osteoporosis in mice by reducing the number of mature osteoclasts attached to the bone surface. The data provided evidence that S1P controlled the migratory behavior of osteoclast precursors, dynamically regulating bone mineral homeostasis (Ishii et al., *Nature*, 458 (7237), 524-528, 2009).

Agonism of the $S1P_1$ receptor has been implicated in enhancement of survival of oligodendrocyte progenitor cells. Survival of oligodendrocyte progenitor cells is a required component of the remyelination process. Remyelination of multiple sclerosis lesions is considered to promote recovery from clinical relapses. (Miron et al., *Ann. Neurol.*, 63:61-71, 2008; Coelho et al., *J. Pharmacol. Exp. Ther.*, 323:626-635, 2007; Dev et al., *Pharmacology and Therapeutics*, 117:77-93, 2008). It also has been shown that the $S1P_1$ receptor plays a role in platelet-derived growth factor (PDGF)-induced oligodendrocyte progenitor cell mitogenesis (Jung et al., Glia, 55:1656-1667, 2007).

Agonism of the $S1P_1$ receptor has also been reported to mediate migration of neural stem cells toward injured areas of the central nervous system (CNS), including in a rat model of spinal cord injury (Kimura et al., *Stem Cells*, 25:115-124, 2007).

Agonism of the $S1P_1$ receptor has been implicated in the inhibition of keratinocyte proliferation (Sauer et al., *J. Biol. Chem.*, 279:38471-38479, 2004), consistent with reports that S1P inhibits keratinocyte proliferation (Kim et al., *Cell Signal*, 16:89-95, 2004). The hyperproliferation of keratinocytes at the entrance to the hair follicle, which can then become blocked, and an associated inflammation are significant pathogenetic factors of acne (Koreck et al., *Dermatology*, 206:96-105, 2003; Webster, *Cutis*, 76:4-7, 2005).

FTY720 has been reported to have therapeutic efficacy in inhibiting pathologic angiogenesis, such as that as may occur in tumor development. Inhibition of angiogenesis by FTY720 is thought to involve agonism of the $S1P_1$ receptor (Oo et al., *J. Biol. Chem.*, 282; 9082-9089, 2007; Schmid et al., *J. Cell Biochem.*, 101:259-270, 2007). FTY720 has been reported to have therapeutic efficacy for inhibiting primary and metastatic tumor growth in a mouse model of melanoma (LaMontagne et al., *Cancer Res.*, 66:221-231, 2006). FTY720 has been reported to have therapeutic efficacy in a mouse model for metastatic hepatocellular carcinoma (Lee et al., *Clin. Cancer Res.*, 11:84588466, 2005).

It has been reported that oral administration of FTY720 to mice potently blocked VEGF-induced vascular permeability, an important process associated with angiogenesis, inflammation, and pathological conditions such as sepsis, hypoxia, and solid tumor growth (T Sanchez et al., *J. Biol. Chem.*, 278(47), 47281-47290, 2003).

FTY720 has been shown to have therapeutic efficacy in transplant rejection both as a monotherapy and in synergistic combination with a classical immunosuppressant, including cyclosporin A, FK506 and RAD (an mTOR inhibitor). It has been shown that, unlike the classical immunosuppressants cyclosporin A, FK506 and RAD, FTY720 has efficacy for prolonging graft survival without inducing general immunosuppression, and this difference in drug action is believed to be relevant to the synergism observed for the combination (Brinkmann et al., *Transplant Proc.*, 33:530-531, 2001; Brinkmann et al., *Transplantation*, 72:764-769, 2001).

Agonism of the $S1P_1$ receptor has been reported to have therapeutic efficacy for prolonging allograft survival in mouse and rat skin allograft models (Lima et al., *Transplant Proc.*, 36:1015-1017, 2004; Yan et al., *Bioorg. & Med. Chem. Lett.*, 16:3679-3683, 2006). FTY720 has been reported to have therapeutic efficacy for prolonging allograft survival in a rat cardiac allograft model (Suzuki et al., *Transpl. Immunol.*, 4:252-255, 1996). FTY720 has been reported to act synergistically with cyclosporin A to prolong rat skin allograft survival (Yanagawa et al., *J. Immunol.*, 160:5493-5499, 1998), to act synergistically with cyclosporin A and with FK506 to prolong rat cardiac allograft survival, and to act synergistically with cyclosporin A to prolong canine renal allograft survival and monkey renal allograft survival (Chiba et al., *Cell Mol. Biol.*, 3:11-19, 2006). KRP-203, an S1P receptor agonist has been reported to have therapeutic efficacy for prolonging allograft survival in a rat skin allograft model and both as monotherapy and in synergistic combination with cyclosporin A in a rat cardiac allograft model (Shimizu et al., *Circulation*, 111:222-229, 2005). KRP-203 also has been reported to have therapeutic efficacy in combination with mycophenolate mofetil (MMF; a prodrug for which the active metabolite is mycophenolic acid, an inhibitor of purine biosynthesis) for prolonging allograft survival both in a rat renal allograft model and in a rat cardiac allograft model (Suzuki et al., *J. Heart Lung Transplant*, 25:302-209, 2006; Fujishiro et al., *J. Heart Lung Transplant*, 25:825-833, 2006). It has been reported that an agonist of the $S1P_1$ receptor, AUY954, in combination with a subtherapeutic dose of RAD001 (Certican/Everolimus, an mTOR inhibitor) can prolong rat cardiac allograft survival (Pan et al., *Chemistry & Biology*, 13:1227-1234, 2006). In a rat small bowel allograft model, FTY720 has been reported to act synergistically with cyclosporin A to prolong small bowel allograft survival (Sakagawa et al., *Transpl. Immunol.*, 13:161-168, 2004). FTY720 has been reported to have therapeutic efficacy in a mouse islet graft model (Fu et al., *Transplantation*, 73:1425-1430, 2002; Liu et al., *Microsurgery*, 27:300-304; 2007) and in a study using human islet cells to evidence no detrimental effects on human islet function (Truong et al., *American Journal of Transplantation*, 7:2031-2038, 2007).

FTY720 has been reported to reduce the nociceptive behavior in the spared nerve injury model for neuropathic pain which does not depend on prostaglandin synthesis (O. Costu et al., *Journal of Cellular and Molecular Medicine* 12(3), 995-1004, 2008).

FTY720 has been reported to impair initiation of murine contact hypersensitivity (CHS). Adoptive transfer of immunized lymph node cells from mice treated with FTY720 during the sensitization phase was virtually incapable of inducing CHS response in recipients (D. Nakashima et al., *J. Investigative Dermatology* (128(12), 2833-2841, 2008).

It has been reported that prophylactic oral administration of FTY720 (1 mg/kg, three times a week), completely prevented the development of experimental autoimmune myasthenia gravis (EAMG) in C57BL/6 mice (T. Kohono et al., *Biological & Pharmaceutical Bulletin*, 28(4), 736-739, 2005).

$S1P_1$ receptor agonists are useful for treating or preventing conditions where suppression of the immune system or agonism of the $S1P_1$ receptor is in order, such as diseases and disorders mediated by lymphocytes, transplant rejection, autoimmune diseases and disorders, inflammatory diseases and disorders, and conditions that have an underlying defect in vascular integrity or that relate to angiogenesis such as may be pathologic.

In some embodiments, an $S1P_1$ receptor-associated disorder is selected from, for example, diseases and disorders mediated by lymphocytes, transplant rejection, autoimmune diseases and disorders, inflammatory diseases and disorders (e.g., acute and chronic inflammatory conditions), cancer, and conditions that have an underlying defect in vascular integrity or that are associated with angiogenesis such as may be pathologic (e.g., as may occur in inflammation, tumor development and atherosclerosis). Such conditions where suppression of the immune system or agonism of the $S1P_1$ receptor is in order include diseases and disorders mediated by lymphocytes, conditions that have an underlying defect in vascular integrity, autoimmune diseases and disorders, inflammatory diseases and disorders (e.g., acute and chronic inflammatory conditions), acute or chronic rejection of cells, an autoimmune disease of the liver including biliary cirrhosis, primary biliary cirrhosis, autoimmune hepatitis, primary sclerosing cholangitis, and primary biliary cholangitis, tissue or solid organ grafts, arthritis including psoriatic arthritis and rheumatoid arthritis, diabetes including type I diabetes and the disorders associated therewith, myasthenia gravis, demyelinating disease including multiple sclerosis, ischemia-reperfusion injury including renal and cardiac ischemia-reperfusion injury, inflammatory skin disease including psoriasis, atopic dermatitis and acne, hyperproliferative skin disease including acne, inflammatory bowel disease including Crohn's disease and ulcerative colitis, systemic lupus erythematosus, asthma, uveitis, myocarditis, allergy, atherosclerosis, brain inflammation including Alzheimer's disease and brain inflammatory reaction following traumatic brain injury, central nervous system disease including spinal cord injury or cerebral infarction, pathologic angiogenesis including as may occur in primary and metastatic tumor growth, rheumatoid arthritis, diabetic retinopathy and atherosclerosis, cancer, chronic pulmonary disease, acute lung injury, acute respiratory disease syndrome, sepsis, and the like. In addition, $S1P_1$ receptor agonists are useful for treating microbial infections, and viral infections or diseases.

One aspect of the present invention relates to methods for treating an $S1P_1$ receptor-associated disorder in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein.

One aspect of the present invention relates to methods for treating an $S1P_1$ receptor-associated disorder in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein, wherein the disorder is selected from the group consisting of a disease or disorder mediated by lymphocytes, an autoimmune disease or disorder, an inflammatory disease or disorder, primary biliary cirrhosis, cancer, psoriasis, psoriatic arthritis, rheumatoid arthritis, Crohn's disease, transplant rejection, multiple sclerosis, systemic lupus erythematosus, inflammatory bowel disease, ulcerative colitis, type I diabetes, and acne.

One aspect of the present invention relates to methods for treating a disorder in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein, wherein the disorder is selected from the group consisting of primary biliary cirrhosis, psoriasis, psoriatic arthritis, rheumatoid arthritis, Crohn's disease, multiple sclerosis, inflammatory bowel disease, systemic lupus erythematosus, and ulcerative colitis.

One aspect of the present invention relates to methods for treating a disease or disorder mediated by lymphocytes in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein.

One aspect of the present invention relates to methods for treating primary biliary cirrhosis in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein.

One aspect of the present invention relates to methods for treating psoriasis in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein.

One aspect of the present invention relates to methods for treating psoriatic arthritis in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein.

One aspect of the present invention relates to methods for treating rheumatoid arthritis in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein.

One aspect of the present invention relates to methods for treating Crohn's disease in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein.

One aspect of the present invention relates to methods for treating multiple sclerosis in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein.

One aspect of the present invention relates to methods for treating inflammatory bowel disease in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein.

One aspect of the present invention relates to methods for treating systemic lupus erythematosus in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein.

One aspect of the present invention relates to methods for treating ulcerative colitis in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein.

One aspect of the present invention relates to methods for treating an autoimmune disease or disorder in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein.

One aspect of the present invention relates to methods for treating an inflammatory disease or disorder in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein.

One aspect of the present invention relates to methods for treating a microbial or viral infection or disease in an individual comprising administering to the individual in need thereof a therapeutically effective amount of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein, a composition as described herein, or a pharmaceutical composition as described herein.

One aspect of the present invention relates to uses of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of an S1P₁ receptor-associated disorder.

One aspect of the present invention relates to uses of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of an S1P₁ receptor-associated disorder selected from the group consisting of a disease or disorder mediated by lymphocytes, an autoimmune disease or disorder, an inflammatory disease or disorder, primary biliary cirrhosis, cancer, psoriasis, psoriatic arthritis, rheumatoid arthritis, Crohn's disease, transplant rejection, multiple sclerosis, systemic lupus erythematosus, inflammatory bowel disease, ulcerative colitis, type I diabetes, and acne.

One aspect of the present invention relates to uses of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of an S1P₁ receptor-associated disorder selected from the group consisting of primary biliary cirrhosis, psoriasis, psoriatic arthritis, rheumatoid arthritis, Crohn's disease, multiple sclerosis, inflammatory bowel disease, systemic lupus erythematosus, and ulcerative colitis.

One aspect of the present invention relates to uses of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of a disease or disorder mediated by lymphocytes.

One aspect of the present invention relates to uses of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of primary biliary cirrhosis.

One aspect of the present invention relates to uses of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of psoriasis.

One aspect of the present invention relates to uses a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of psoriatic arthritis.

One aspect of the present invention relates to uses of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of rheumatoid arthritis.

One aspect of the present invention relates to uses of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of Crohn's disease.

One aspect of the present invention relates to uses of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of multiple sclerosis.

One aspect of the present invention relates to uses of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of inflammatory bowel disease.

One aspect of the present invention relates to uses of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of systemic lupus erythematosus.

One aspect of the present invention relates to uses of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of ulcerative colitis.

One aspect of the present invention relates to uses of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of an autoimmune disease or disorder.

One aspect of the present invention relates to uses of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of an inflammatory disease or disorder.

One aspect of the present invention relates to uses of a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein in the manufacture of a medicament for the treatment of a microbial or viral infection or disease.

One aspect of the present invention relates to uses of a composition comprising a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein and an excipient in the manufacture of a medicament for administration in the treatment of an S1P₁ receptor-associated disorder.

One aspect of the present invention relates to uses of a composition comprising a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein and an excipient for preparation a medicament for administration in the treatment of an S1P₁ receptor-associated disorder.

One aspect of the present invention relates to uses of a composition comprising a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein and an excipient for compounding a medicament for administration in the treatment of an S1P₁ receptor-associated disorder.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of the human or animal body by therapy.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of an S1P$_1$ receptor-associated disorder.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of an S1P$_1$ receptor-associated disorder selected from the group consisting of a disease or disorder mediated by lymphocytes, an autoimmune disease or disorder, an inflammatory disease or disorder, primary biliary cirrhosis, cancer, psoriasis, psoriatic arthritis, rheumatoid arthritis, Crohn's disease, transplant rejection, multiple sclerosis, systemic lupus erythematosus, inflammatory bowel disease, ulcerative colitis, type I diabetes, and acne.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of an S1P$_1$ receptor-associated disorder selected from the group consisting of primary biliary cirrhosis, psoriasis, psoriatic arthritis, rheumatoid arthritis, Crohn's disease, multiple sclerosis, inflammatory bowel disease, systemic lupus erythematosus, and ulcerative colitis.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of a disease or disorder mediated by lymphocytes.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of primary biliary cirrhosis.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of psoriasis.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of psoriatic arthritis.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of rheumatoid arthritis.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of Crohn's disease.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of multiple sclerosis.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of inflammatory bowel disease.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of systemic lupus erythematosus.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of ulcerative colitis.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of an autoimmune disease or disorder.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of an inflammatory disease or disorder.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid as described herein for use in a method for the treatment of a microbial or viral infection or disease.

In some embodiments, the S1P$_1$ receptor-associated disorder is mediated by lymphocytes. In some embodiments, the S1P$_1$ receptor-associated disorder is primary biliary cirrhosis. In some embodiments, the S1P$_1$ receptor-associated disorder is psoriasis. In some embodiments, the S1P$_1$ receptor-associated disorder is psoriatic arthritis. In some embodiments, the S1P$_1$ receptor-associated disorder is rheumatoid arthritis. In some embodiments, the S1P$_1$ receptor-associated disorder is Crohn's disease. In some embodiments, the S1P$_1$ receptor-associated disorder is multiple sclerosis. In some embodiments, the S1P$_1$ receptor-associated disorder is inflammatory bowel disease. In some embodiments, the S1P$_1$ receptor-associated disorder is systemic lupus erythematosus. In some embodiments, the S1P$_1$ receptor-associated disorder is ulcerative colitis.

Pharmaceutical Compositions and Compositions

One aspect of the present invention relates to pharmaceutical compositions comprising a crystalline free-plate habit of L-arginine salt of (R)-2-(7-(4-cyclopentyl-3-(trifluoromethyl)benzyloxy)-1,2,3,4-tetrahydrocyclo-penta[b]indol-3-yl)acetic acid as described herein and a pharmaceutical excipient.

One aspect of the present invention relates to pharmaceutical compositions comprising a crystalline free-plate habit of L-arginine salt of (R)-2-(7-(4-cyclopentyl-3-(trifluoromethyl)benzyloxy)-1,2,3,4-tetrahydrocyclo-penta[b]indol-3-yl)acetic acid prepared according to any of the methods described herein and a pharmaceutical excipient.

One aspect of the present invention relates to pharmaceutical compositions comprising a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid (Compound 1) in an amount equivalent to a therapeutically effective amount of Compound 1 of the crystalline free-plate habit, wherein the pharmaceutical composition further comprises a diluent, a disintegrant, and a lubricant.

In some embodiments, the diluent comprises a first diluent and a second diluent.

In some embodiments, the first diluent comprises mannitol. In some embodiments, the first diluent comprises mannitol 200 SD, USP.

In some embodiments, the second diluent comprises microcrystalline cellulose. In some embodiments, the second diluent comprises Avicel®. In some embodiments, the second diluent comprises Avicel® PH102, NF.

In some embodiments, the disintegrant is sodium starch glycolate. In some embodiments, the disintegrant is Explotab®, NF.

In some embodiments, the lubricant is magnesium stearate, NF.

In some embodiments, the pharmaceutical composition has a diluent content of about 91% to about 95%.

In some embodiments, the pharmaceutical composition has a first diluent content of about 51% to about 55%.

In some embodiments, the pharmaceutical composition has a second diluent content of about 37% to about 43%.

In some embodiments, the pharmaceutical composition has a disintegrant content of about 3% to about 5%.

In some embodiments, the pharmaceutical composition has a lubricant content of about 0.2% to about 0.8%.

In some embodiments, the pharmaceutical composition has:
- a crystalline free-plate habit of L-arginine salt of (R)-2-(7-(4-cyclopentyl-3-(trifluoromethyl)-benzyloxy)-1,2,3,4-tetrahydrocyclopenta[b]indol-3-yl)acetic acid content of 0.69%;
- a mannitol content of 54.81%;
- a microcrystalline cellulose content of 40%;
- a sodium starch glycolate content of 4%; and
- a magnesium stearate content of 0.5%.

In some embodiments, the pharmaceutical composition has:
- a crystalline free-plate habit of L-arginine salt of (R)-2-(7-(4-cyclopentyl-3-(trifluoromethyl)-benzyloxy)-1,2,3,4-tetrahydrocyclopenta[b]indol-3-yl)acetic acid content of 1.381%;
- a mannitol content of 54.119%;
- a microcrystalline cellulose content of 40%;
- a sodium starch glycolate content of 4%; and
- a magnesium stearate content of 0.5%.

In some embodiments, the pharmaceutical composition has:
- a crystalline free-plate habit of L-arginine salt of (R)-2-(7-(4-cyclopentyl-3-(trifluoromethyl)-benzyloxy)-1,2,3,4-tetrahydrocyclopenta[b]indol-3-yl)acetic acid content of 2.762%;
- a mannitol content of 52.738%;
- a microcrystalline cellulose content of 40%;
- a sodium starch glycolate content of 4%; and
- a magnesium stearate content of 0.5%.

In some embodiments, the pharmaceutical composition has:
- a crystalline free-plate habit of L-arginine salt of (R)-2-(7-(4-cyclopentyl-3-(trifluoromethyl)-benzyloxy)-1,2,3,4-tetrahydrocyclopenta[b]indol-3-yl)acetic acid content of 4.143%;
- a mannitol content of 51.357%;
- a microcrystalline cellulose content of 40%;
- a sodium starch glycolate content of 4%; and
- a magnesium stearate content of 0.5%.

One aspect of the present invention relates to compositions comprising a crystalline free-plate habit of L-arginine salt of (R)-2-(7-(4-cyclopentyl-3-(trifluoromethyl)benzyloxy)-1,2,3,4-tetrahydrocyclo-penta[b]indol-3-yl)acetic acid as described herein or prepared according to any of the methods described herein.

One aspect of the present invention relates to pharmaceutical compositions comprising a crystalline free-plate habit of L-arginine salt of (R)-2-(7-(4-cyclopentyl-3-(trifluoromethyl)benzyloxy)-1,2,3,4-tetrahydrocyclo-penta[b]indol-3-yl)acetic acid as described herein or prepared according to any of the methods described herein, and a pharmaceutical excipient.

In some embodiments, the composition and/or pharmaceutical composition is suitable for oral, rectal, nasal, topical, buccal, sub-lingual, or vaginal, or in a form suitable for administration by inhalation, insufflation, or by a transdermal patch. In some embodiments, the composition and/or pharmaceutical composition is suitable for oral administration.

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants can be used in tablets and capsules for oral administration. Liquid preparations for oral administration can be in the form of solutions, emulsions, aqueous or oily suspensions and syrups. Alternatively, the oral preparations can be in the form of dry powder that can be reconstituted with water or another suitable liquid vehicle before use. Additional additives such as suspending or emulsifying agents, non-aqueous vehicles (including edible oils), preservatives and flavorings and colorants can be added to the liquid preparations. Parenteral dosage forms can be prepared by dissolving the compound provided herein in a suitable liquid vehicle and filter sterilizing the solution before filling and sealing an appropriate vial or ampule. These are just a few examples of the many appropriate methods well known in the art for preparing dosage forms.

The compounds provided herein, such as, the L-arginine salt of Compound 1, can be formulated into pharmaceutical compositions using techniques well known to those in the art. Suitable pharmaceutically-acceptable carriers, outside those mentioned herein, are known in the art; for example, see Remington, The Science and Practice of Pharmacy, 20$^{th}$ Edition, 2000, Lippincott Williams & Wilkins, (Editors: Gennaro et al.).

The term "composition" refers to at least one compound of the invention in combination with at least one other component. Examples of compositions include, but are not limited to, a reference standard comprising a compound of the present invention (e.g., for use in method development, in-process testing, and the like); bulk API (i.e., Active Pharmaceutical Ingredient) of a compound of the present invention (e.g., for use in formulating a pharmaceutical composition, compounding to form a medicament for use in administrating to a patient, and the like); a combined preparation (i.e., a compound of the present invention in combination with a pharmaceutical/therapeutic agent or agents); a biological sample comprising a compound of the present invention (e.g., for use in or obtained from a patient, an animal, a pharmacokinetic study, ADME study, LADME study, and the like); a reaction mixture comprising a compound of the present invention, such as, a reaction mixture as described in any of the Examples herein; a manufacturing reaction mixture comprising a compound of the present invention in combination with one or more components such as solvents, reactants, side-products, etc.; and the like. It is understood that pharmaceutical compositions are a specific subset of compositions. In one embodiment, a composition can be used in the treatment of a disease or order as described herein.

The compounds provided herein, such as, the L-arginine salt of Compound 1, can be "compounded" or be involved in a process of "compounding" to prepare a personalized medication for a patient or a group of patients for the treatment of a disease or disorder as described herein. Techniques used in "compounding" are well known to those in the art, such as, the Compounding Pharmacist. In general, "compounding" refers to the practice of preparing a prescription medication for a specific patient. Compounding can involve the preparation, mixing, assembling, packaging, and/or labeling of a drug (1) as the result of a practitioner's Prescription Drug Order or initiative based on the pharmacist/patient/prescriber relationship in the course of professional practice, or (2) for the purpose of research, teaching, or chemical analysis and not for sale or dispensing. Compounding also includes the preparation of drugs in anticipation of Prescription Drug Orders based on routine, regularly observed patterns. Compounding services provide a vital role in health care as commercially manufactured drugs may not be suited for every person. Due to patient differences, such as, body size, varying drug tolerances, allergies, and/or special requirements (e.g., dosages that are sugar-free, gluten-free, casein-free, soy-free, and/or dye-free), a patient may require a medication that is not commercially available with the exact strength needed or may require a medication that lacks a certain component found in the commercial drug. Through compounding, the pharmacist can adjust the medication to the exact dosage and excipient (s) needed by the patient, for example, a medication or medicament suitable for oral, rectal, nasal, topical, buccal, sub-lingual, vaginal, parenteral, intramuscular, sub-cutaneous, or intravenous administration, or in a form suitable for administration by inhalation, insufflation, or by a transdermal patch.

While it is possible that, for use in the prophylaxis or treatment, a compound provided herein can, in an alternative use, be administered as a raw or pure chemical, it is preferable however to present the compound or active ingredient as a pharmaceutical formulation or composition further comprising a pharmaceutically acceptable carrier.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with minimal degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds provided herein, such as, the L-arginine salt of Compound 1, together with a conventional adjuvant, carrier, or diluent, can thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof can comprise conventional ingredients in conventional proportions, with or without additional active compounds or principles and such unit dosage forms may contain any suitably effective amount of the active ingredient commensurate with the intended daily dosage range to be employed.

For oral administration, the pharmaceutical composition may be in the form of, for example, a tablet, capsule, suspension, or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

In some embodiments, the pharmaceutical composition is a solid formulation, such as, a tablet, capsule, suspension for oral administration, and the like.

The dose when using the compounds provided herein, such as, the L-arginine salt of Compound 1, can vary within wide limits and as is customary and is known to the physician, it is to be tailored to the individual conditions in each individual case. It depends, for example, on the nature and severity of the illness to be treated, on the condition of the individual, such as a patient, on the compound employed, on whether an acute or chronic disease state is treated, or prophylaxis conducted, or on whether further active compounds are administered in addition to the compounds provided herein, such as, the L-arginine salt of Compound 1. Representative doses include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the healthcare provider it may be necessary to deviate upward or downward from the doses described herein.

In some embodiments, the dose is 0.5 mg. In some embodiments, the dose is 1.0 mg. In some embodiments, the dose is 2.0 mg. In some embodiments, the dose is 3.0 mg. In some embodiments, the dose is 5.0 mg.

All dosage amounts disclosed herein are calculated with respect to the active moiety, i.e., the molecule or ion that gives the intended pharmacologic or physiologic action.

The amount of active ingredient, or an active salt or derivative thereof, required for use in treatment will vary not only with the particular salt selected but also with the route of administration, the nature of the condition being treated and the age and condition of the individual and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the individual, the severity of the disease, the route of administration, pharmacological considerations such as the activity, efficacy, pharmacokinetic and toxicology profiles of the particular compound employed, whether a drug delivery system is utilized, whether an acute or chronic disease state is being treated or prophylaxis conducted or whether further active compounds are administered in addition to the compounds provided herein (e.g. L-arginine salt of Compound 1) such as part of a drug combination. The dosage regimen for treating a disease condition with the compounds and/or compositions provided herein is selected in accordance with a variety of factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods disclosed herein.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations. The daily dose can be divided, especially when relatively large amounts are administered as deemed appropriate, into several, for example 2, 3, or 4 part administrations. If appropriate, depending on individual behavior, it may be necessary to deviate upward or downward from the daily dose indicated.

The compounds provided herein, such as, the L-arginine salt of Compound 1, can be administered in a wide variety of oral and parenteral dosage forms. It will be obvious to those skilled in the art that the dosage forms may comprise, as the active component, either a compound provided herein or a pharmaceutically acceptable salt, hydrate, or solvate of a compound provided herein.

For preparing pharmaceutical compositions from the compounds provided herein, such as, the L-arginine salt of Compound 1, the selection of a suitable pharmaceutically acceptable carrier can be a solid, liquid, or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desired shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" refers to the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds provided herein, such as, the L-arginine salt of Compound 1, may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds provided herein, such as, the L-arginine salt of Compound 1, may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds provided herein, such as, the L-arginine salt of Compound 1, or pharmaceutical compositions comprising them, are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds provided herein as an aerosol can be prepared by processes well known to the person skilled in the art. For their preparation, for example, solutions or dispersions of the compounds provided herein in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

As will be recognized, the steps of the methods provided herein need not be performed any particular number of times or in any particular sequence. Additional objects, advantages and novel features of the invention(s) will become apparent to those skilled in the art upon examination of the following examples thereof, which are intended to be illustrative and not intended to be limiting.

EXAMPLES

The compounds disclosed herein and their syntheses are further illustrated by the following examples. The following examples are provided to further define the invention without, however, limiting the invention to the particulars of these examples. The compounds described herein, supra and infra, are named according to the AutoNom version 2.2, CS ChemDraw Ultra Version 9.0.7, or ChemBioDraw Ultra 12.0.2.1076. In certain instances common names are used and it is understood that these common names would be recognized by those skilled in the art.

Chemistry: Proton nuclear magnetic resonance ($^1$H NMR) spectra were recorded on a Bruker Avance III-400 equipped with a 5 mm BBFO probe. Chemical shifts are given in parts per million (ppm) with the residual solvent signal used as reference. NMR abbreviations are used as follows: s=singlet, d=doublet, dd=doublet of doublets, t=triplet, q=quartet, m=multiplet, bs=broad singlet, sxt=sextet. Microwave irradiations were carried out using a Smith Synthesizer™ or an Emrys Optimizer™ (Biotage). Thin-layer chromatography (TLC) was performed on silica gel 60 $F_{254}$ (Merck), preparatory thin-layer chromatography (prep TLC) was performed on PK6F silica gel 60 Å 1 mm plates (Whatman) and column chromatography was carried out on a silica gel column using Kieselgel 60, 0.063-0.200 mm (Merck). Evaporation was done under reduced pressure on a Büchi rotary evaporator. Celite® 545 was used for filtration of palladium.

LCMS spec: HPLC-Agilent 1200; pumps: G1312A; DAD: G1315B; Autosampler: G1367B; Mass spectrometer-Agilent G1956A; ionization source: ESI; Drying Gas Flow: 10 L/min; Nebulizer Pressure: 40 psig; Drying Gas Temperature: 350° C.; Capillary Voltage: 2500 V) Software: Agilent Chemstation Rev.B.04.03.

Example 1: Preparation and Crystallization of L-Arginine Salt of (R)-2-(7-(4-Cyclopentyl-3-(trifluoromethyl)benzyloxy)-1,2,3,4-tetrahydrocyclopenta[b]indol-3-yl)acetic Acid as Crystalline Spherulite Morphology A mixture of ethyl 2-(7-(4-cyclopentyl-3-(trifluoromethyl)benzyloxy)-1,2,3,4-tetrahydrocylopenta[b]indol-3-yl) acetate (29.0 g, 59.7 mmol, 1.00 equiv.), lipase B (*Candida antarctica*, immobilized, 1.45 g), and aqueous potassium phosphate buffer (pH 7.8±0.2, 1.0 M, 21.75 mL) in acetonitrile (268.5 mL) was stirred under nitrogen at 40° C. for at least 8 hours and until the concentration of product (i.e., (R)-2-(7-(4-cyclopentyl-3-(trifluoromethyl)benzyloxy)-1,2, 3,4-tetrahydrocyclopenta[b]indol-3-yl)acetic acid) was ≥40% area by HPLC. Then, while the reaction mixture was stirred at 20° C., its pH was adjusted to 4 to 6 by addition of 1.0 M aqueous citric acid (26.1 mL). After removal of solids by filtration, washing the reactor then the filter-cake with acetonitrile (3×10 mL), and removal of acetonitrile by vacuum distillation, the product mixture was partitioned between ethyl acetate (58 mL) and water (58 mL). The ethyl acetate phase was washed with water (2×58 mL) and then with brine (3×58 mL) at least twice and until the pH of the brine wash was 4 to 7 and the level of citric acid in the ethyl acetate phase was verified to be <0.1% by $^1$H NMR spectroscopy. Ethyl acetate was replaced with 2-propanol (3×87 mL) by vacuum distillation. After complete removal of ethyl acetate was verified by $^1$H NMR spectroscopy, the 2-propanol (10 mL/g of (R)-2-(7-(4-cyclopentyl-3-(trifluoromethyl)benzyloxy)-1,2,3,4-tetrahydrocyclopenta[b]indol-3-yl)acetic acid) solution of product was filtered and analyzed by both achiral and chiral HPLC to determine the (R)-2-(7-(4-cyclopentyl-3-(trifluoromethyl)benzyloxy)-1,2,3,4-tetrahydrocyclopenta[b]indol-3-yl)acetic acid concentration and to determine the content of the corresponding enantiomer acid (i.e., (S)-2-(7-(4-cyclopentyl-3-(trifluoromethyl)benzyloxy)-1,2,3,4-tetrahydrocyclopenta[b]indol-3-yl)acetic acid). The solution was concentrated to an oil and a portion of which was used in the preparation of the L-arginine salt of (R)-2-(7-(4-cyclopentyl-3-(trifluoromethyl)benzyloxy)-1,2,3,4-tetrahydrocyclopenta[b]indol-3-yl)acetic acid as described below.

A 2-propanol product mixture containing approximately equal amounts of (R)-2-(7-(4-cyclopentyl-3-(trifluoromethyl)benzyloxy)-1,2,3,4-tetrahydrocyclopenta[b]indol-3-yl)acetic acid (3.0 g, 6.56 mmol, 1.000 equiv.) and corresponding (S)-ethyl ester was stirred with 2-propanol (50 mL) at 60° C. After 5 minutes, seed material of L-arginine salt (0.06 g) was added and stirred for 10 minutes. Then a preheated 2.27 M aqueous solution of L-arginine (2.89 mL, 6.56 mmol, 1.00 equiv.) was added drop-wise over 15 minutes to the mixture at 60° C. to form the crystalline L-arginine salt of (R)-2-(7-(4-cyclopentyl-3-(trifluoromethyl)benzyloxy)-1,2,3,4-tetrahydrocyclopenta[b]indol-3-yl)acetic acid. The yellowish suspension was stirred (at ca. 100 rpm) for 60 minutes. The mixture was cooled to 25° C. f 5° C. at a rate of 0.5° C. per minute. The L-arginine salt was isolated by filtration and washed with 2-propanol (3×3 mL) and then ethyl acetate (3×3 mL) until no wet cake impurity exceeds 1% area by HPLC. The product was then vacuum dried at 40° C.±5° C. for 5 hours, to provide 3.356 g (40.5% yield) crystalline L-arginine salt as spherulites (FIG. 1 shows the spherulites using scanning electron microscopy (SEM) and FIG. 2 shows the spherulites using polarized light microscopy (PLM), with the spherulites exhibiting characteristic crosses when visualized under cross polars); HPLC: 99.2% area (achiral), 98.8% w/w (achiral), and 99.5% area (chiral); DSC 201.97° C.; particle size: mean 23.58 μm, 11.46 std. dev., 6.7 μm minimum, 47.38 μm maximum length by PLM.

Example 2: Preparation and Crystallization of L-Arginine Salt of (R)-2-(7-(4-Cyclopentyl-3-(trifluoromethyl)benzyloxy)-1,2,3,4-tetrahydrocyclopenta[b]indol-3-yl)acetic Acid A mixture of ethyl 2-(7-(4-cyclopentyl-3-(trifluoromethyl)benzyloxy)-1,2,3,4-tetrahydrocylopenta[b]indol-3-yl) acetate (21.86 kg, 45.0 mol, 1.000 equiv.), lipase B (*Candida antarctica*, immobilized, 0.64 kg), and 18.4 kg of aqueous potassium phosphate buffer (pH 7.8±0.2, 1.0 M) in 161.0 kg of acetonitrile was stirred under nitrogen at 40° C.±5° C. for at least 8 hours and until the concentration of the product (i.e., (R)-2-(7-(4-cyclopentyl-3-(trifluoromethyl)benzyloxy)-1,2,3,4-tetrahydrocyclopenta[b]indol-3-yl)acetic acid) was ≥40% area by HPLC. Then, while the reaction mixture was stirred at 25° C.±5° C., the pH was adjusted to 4 to 5 by addition of 1.0 M aqueous citric acid. After removal of solids by filtration and removal of acetonitrile by vacuum distillation, the product mixture was partitioned between ethyl acetate (40.8 kg), water (44.6 kg) and brine (6.7 kg). The ethyl acetate phase was washed with brine (2×54 kg) at least twice and until the pH of the brine wash was 4 to 6 and the level of citric acid in the ethyl acetate phase was verified to be <0.1% by $^1$H NMR spectroscopy. Ethyl acetate was replaced with 2-propanol (106 kg) by vacuum distillation. After complete removal of ethyl acetate was verified by $^1$H NMR spectroscopy, the 2-propanol solution of product was diluted with 53.2 kg of 2-propanol, filtered, and analyzed by both achiral and chiral HPLC to determine the concentration of (R)-2-(7-(4-cyclopentyl-3-(trifluoromethyl)benzyloxy)-1,2,3,4-tetrahydrocyclopenta[b]indol-3-yl)acetic acid and to determine the corresponding enantiomer acid (i.e., (S)-2-(7-(4-cyclopentyl-3-(trifluoromethyl)benzyloxy)-1,2,3,4-tetrahydrocyclopenta[b]indol-3-yl)acetic acid) content.

Figure 3A:
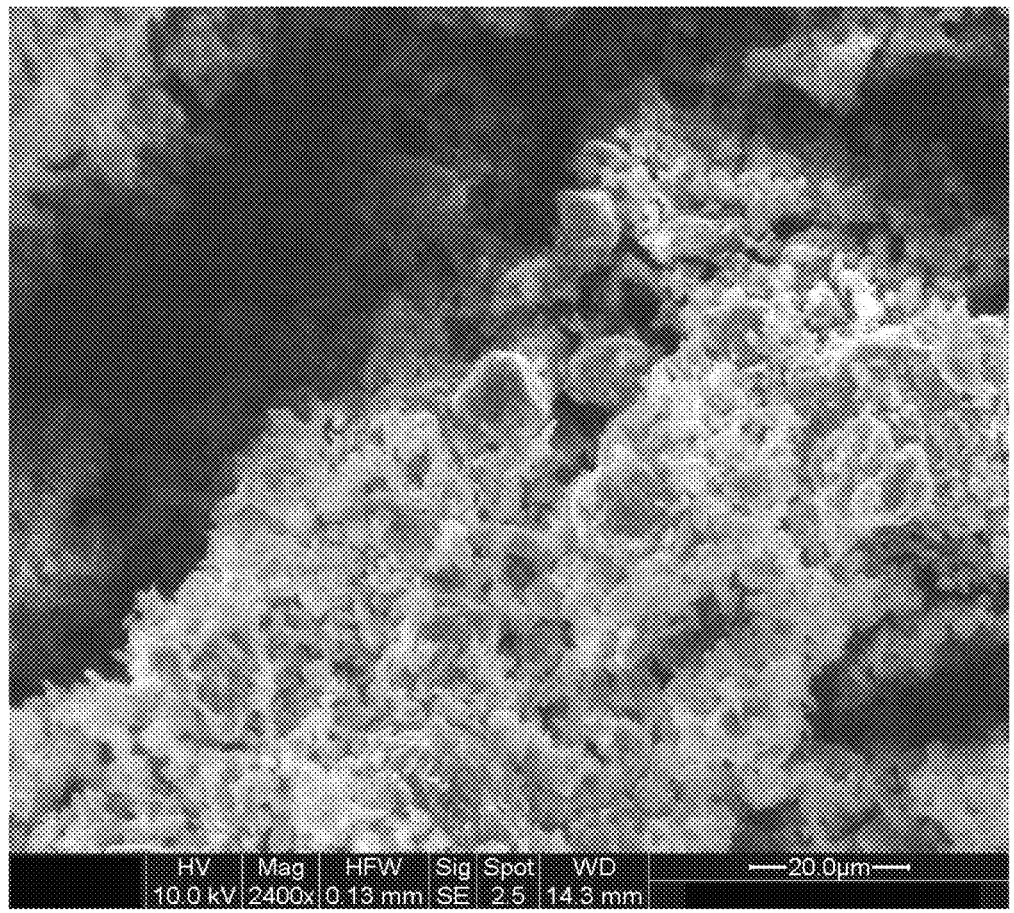
FIG. 3A shows a micrograph of the crystal morphology as described in Example 2 (Lot J2) using scanning electron microscopy (SEM).
Figure 3B:
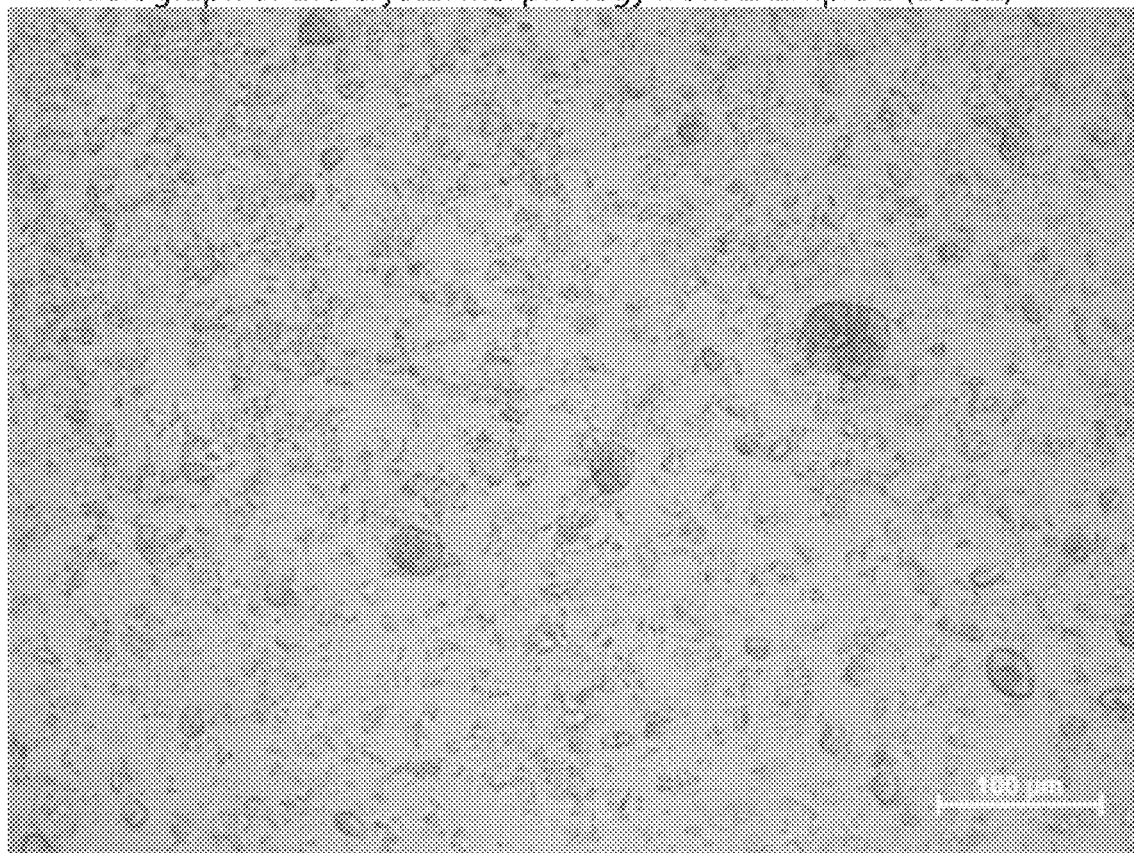
FIG. 3B shows a micrograph of the crystal morphology as described in Example 2 (Lot J2).

A 2-propanol product mixture containing approximately equal amounts of (R)-2-(7-(4-cyclopentyl-3-(trifluoromethyl)benzyloxy)-1,2,3,4-tetrahydrocyclopenta[b]indol-3-yl)acetic acid and the corresponding (S)-ethyl ester was adjusted to 16.7 L/kg of the (R)-acid by adding 2-propanol and stirred at 60° C.±5° C. L-arginine salt of Compound 1 seed material (0.18 kg) was added. To the mixture was added an aqueous solution of L-arginine (2.27 M, 3.63 kg, 20.8 mol, 0.463 equiv. in 9.12 kg of water, preheated to 60° C.±5° C.) to crystallize the L-arginine salt of Compound 1. The mixture was slowly cooled to 25° C.±5° C. and after crystallization was complete, the L-arginine salt of Compound 1 was isolated by filtration and washed with 2-propanol (45 kg) and then ethyl acetate (97.4 kg) until no wet cake impurity exceeds 1% area by HPLC. The product was then vacuum dried at 40° C.±5° C., sieved, and packaged under nitrogen to provide 12.15 kg (42.7% yield) unmilled L-arginine salt of (R)-2-(7-(4-cyclopentyl-3-(trifluoromethyl)benzyloxy)-1,2,3,4-tetrahydrocyclopenta[b]indol-3-yl)acetic acid. The morphology was found to be different from that described in Example 1. The morphology was characterized as a very fine powder, consisting of small, tightly-layered agglomerates, thin flakes, and very fine, irregularly-shaped fragments (see FIG. 3A and FIG. 3B). HPLC: 99.5% area (achiral); DSC: 204.11° C. (melting onset); Particle size: 14 μm (mean length), 1.94 μm minimum and 54.79 μm maximum based on PLM.

Four lots (i.e., Lots J1, J2, J3, and J4) of the L-arginine salt of Compound 1 totaling 45.82 kg were manufactured from 88.4 kg of ethyl 2-(7-(4-cyclopentyl-3-(trifluoromethyl)benzyloxy)-1,2,3,4-tetrahydrocylopenta[b]indol-3-yl) acetate with Lot J2 being described directly above and Lots J1, J3, and J4 being prepared by substantially the same procedure as described for Lot J2. Yields for the dry unmilled L-arginine salt based on ethyl ester ranged from 39.4 mol % to 43.6 mol % and averaged 42.2 mol %. Total product impurities based on achiral HPLC ranged from 0.5% area to 1.2% area and averaged 0.8% area. Levels of the corresponding (S)-acid were less than the quantitation limit (0.7% area).

Figure 4A:
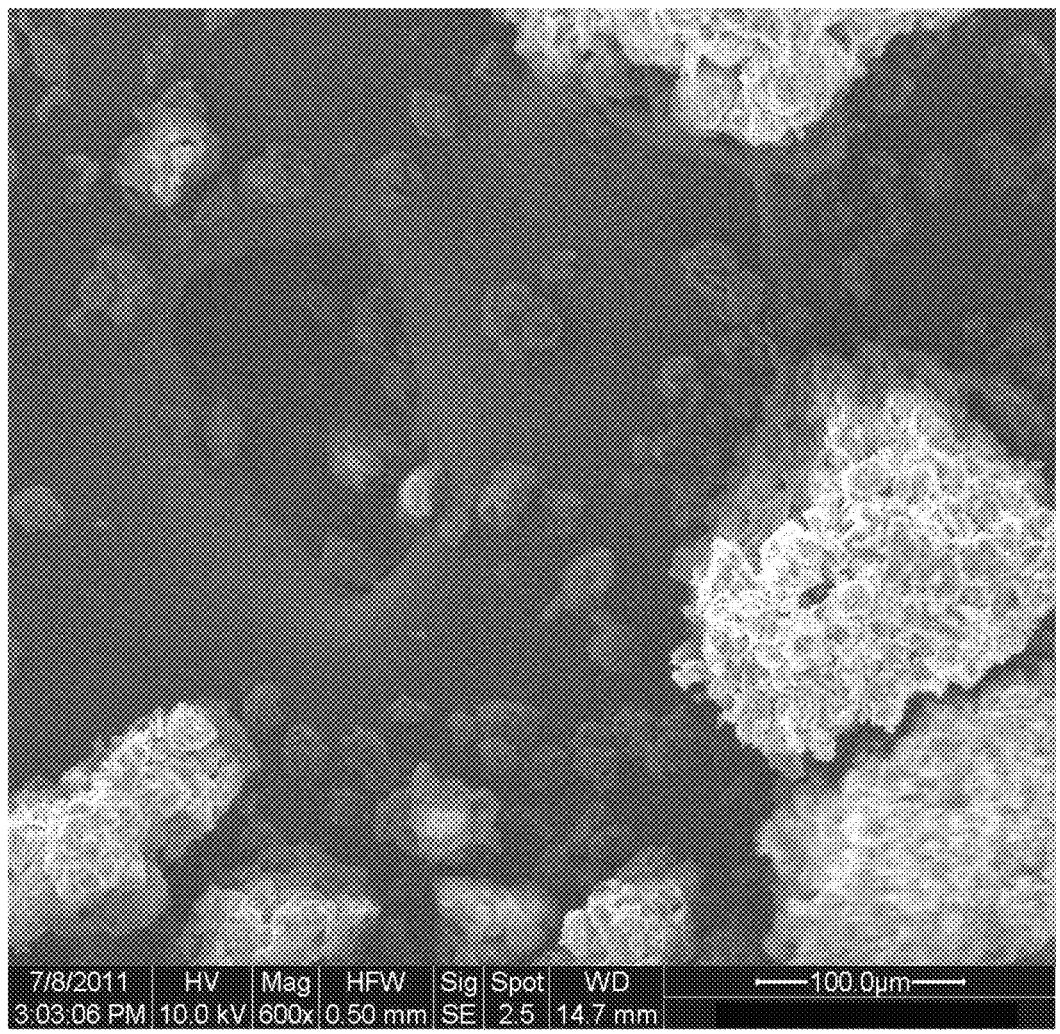
FIG. 4A shows a micrograph of the crystal morphology as described in Example 2 (Lot J1) using scanning electron microscopy (SEM).
Figure 4B:
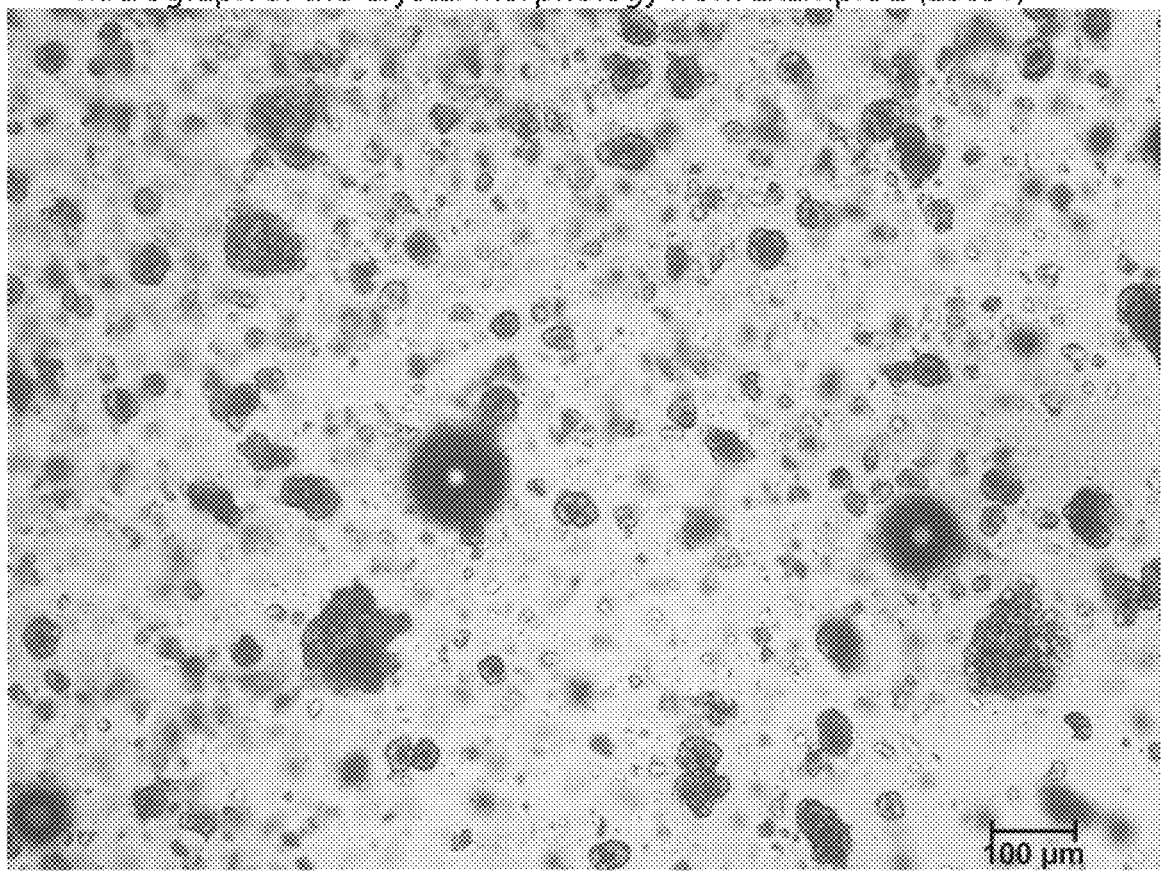
FIG. 4B shows a micrograph of the crystal morphology as described in Example 2 (Lot J1).

In addition to Lot J2, the morphology of Lot J1 was also analyzed by microscopy. The morphology for Lot J1 was characterized as thin lamellar (stacked) flakes, layered into agglomerates that were tightly-layered and the agglomerates not very porous (see FIG. 4A and FIG. 4B). Differences were observed for the morphologies for Lots J1 and J2.

All four lots were reworked by recrystallization from aqueous 2-propanol as described below in Example 3.

Example 3: Preparation of a Crystalline Plate Habit or Morphology by Recrystallization of L-Arginine Salt of (R)-2-(7-(4-Cyclopentyl-3-(trifluoromethyl) benzyloxy)-1,2,3,4-tetrahydrocyclopenta[b]indol-3-yl)acetic Acid A slurry of the L-arginine salt of (R)-2-(7-(4-cyclopentyl-3-(trifluoromethyl)benzyloxy)-1,2,3,4-tetrahydrocyclopenta[b]indol-3-yl)acetic acid (8.20 kg, 12.981 mol) in a mixture of 2-propanol (34.35 kg) and USP water (7.71 kg) was heated to 75° C. with stirring at 100 rpm under nitrogen atmosphere to furnish a solution which was further heated at 78° C. for 0.5 hour. Then, the solution was cooled to 66° C. over 1.5 hour and stirred at 61° C. to 66° C. for about 0.75 hour. 2-Propanol (10.05 kg) was added over 1 hour 15 minutes and stirred at 67° C. for 1 hour. The slurry was heated to 72° C. to 74° C. to give a solution with a few undissolved particulates and stirred at 81 rpm for 39 minutes at that temperature. The slurry was cooled to 67° C. over 61 minutes and stirred at 67° C. for 34 minutes and 2-propanol (10.06 kg) was added over 1 hour 11 minutes to maintain temperature at 65° C. The slurry was stirred at 66° C. for 1 hour. The slurry was then heated to 70° C. to 74° C. for 55 minutes to ensure to keep some undissolved crystals. The slurry was then cooled to 65° C. over 1 hour and 51 minutes and stirred at 60° C. to 65° C. for an additional 55 minutes and 2-Propanol (10.71 kg) was added at 65° C. over 1 hour and 15 minutes. The slurry was stirred at 66° C. for 1 hour 57 minutes. Then, the slurry was heated again to 75° C. over 1 hour, stirred at 75° C. to 78° C. for 40 minutes, and gradually cooled to 67° C. over approximately 1 hour. The slurry was stirred at about 66° C. to 67° C. for 34 minutes and the slurry was further cooled to 20° C. over 10 hour 48 minutes and continued to stir for additional 6 hour 10 minutes prior to filtration. The resultant slurry was filtered. The filter cake was rinsed with 19.31 kg of 2-propanol. No filtration problems were observed. The wet cake was dried under vacuum at about 40° C. to provide 7.44 kg (91% yield) of the L-arginine salt of Compound 1 as an off-white solid. The solids were delumped using a Fitz mill at 1000 rpm using hammer forward position. The milled L-arginine salt (7.36 kg, 89.8% yield) was packaged for storage. FIG. 5A shows the plates using polarized light microscopy (PLM). DSC: 207.19° C.; PLM: Mean Length: 80 μm, (65 μm std dev), 12 μm minimum and 266 μm maximum. FIG. 5B shows a copy of FIG. 5A that has been modified to add an outline of a substantially intact/complete free-plate with an elongated hexagonal shape.

Four lots of the L-arginine salt (44.95 kg, described in Example 2) were recrystallized to five L-arginine salt lots totaling 33.19 kg. Lot A3 was prepared as described directly above. Lots A1, A2, A4, and A5 were prepared by substantially the same procedure as described for Lot A3. For these lots, total impurities by achiral HPLC were about 0.1% area, and achiral assays were 100.0% w/w-101.2% w/w and averaged 100.3% w/w. Levels of the corresponding (S)-acid were below the quantitation limit at 0.14% area. The DSC onset temperatures for the five batches are shown below in TABLE A1.

TABLE A1

Figure 6:
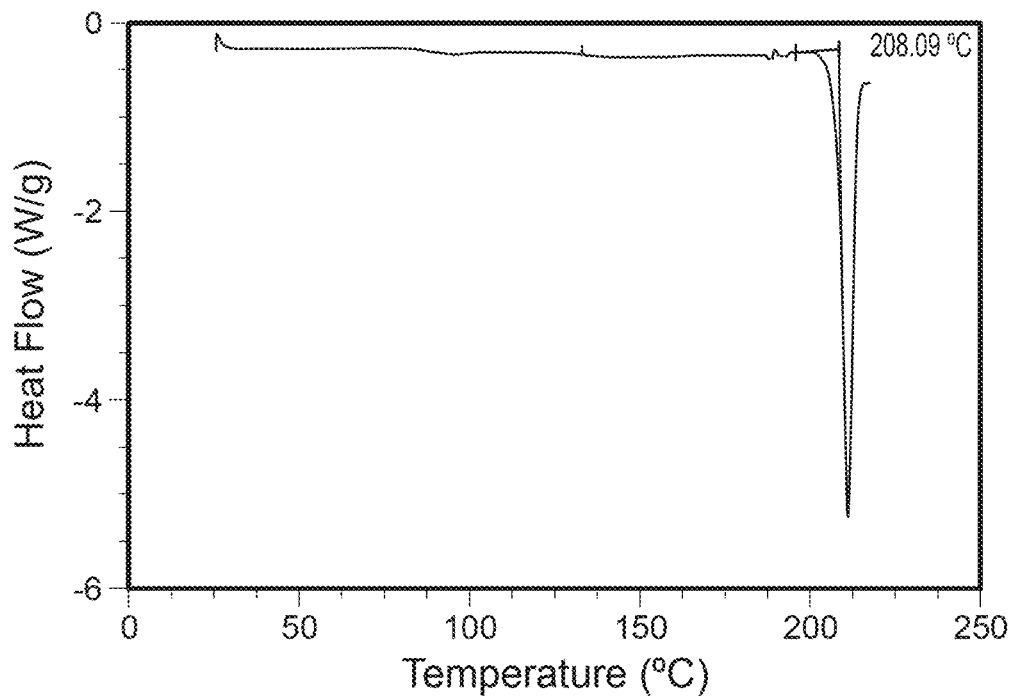
FIG. 6 shows a differential scanning calorimetry (DSC) thermogram for Lot A1 (plates) as described in Example 3.
Figure 7:
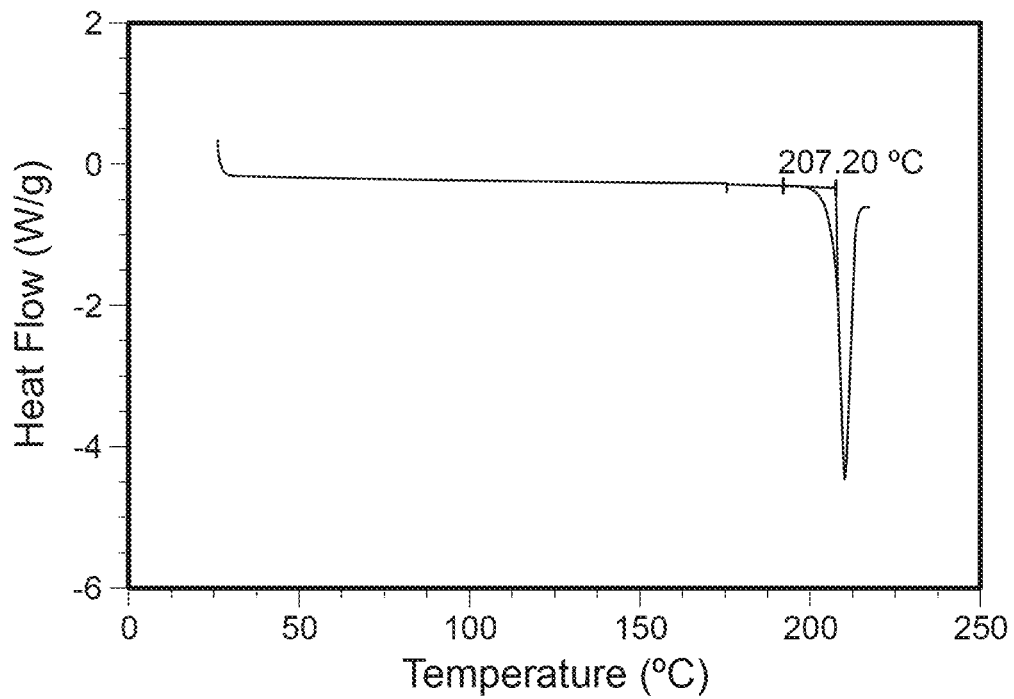
FIG. 7 shows a differential scanning calorimetry (DSC) thermogram for Lot A2 (plates) as described in Example 3.
Figure 8:
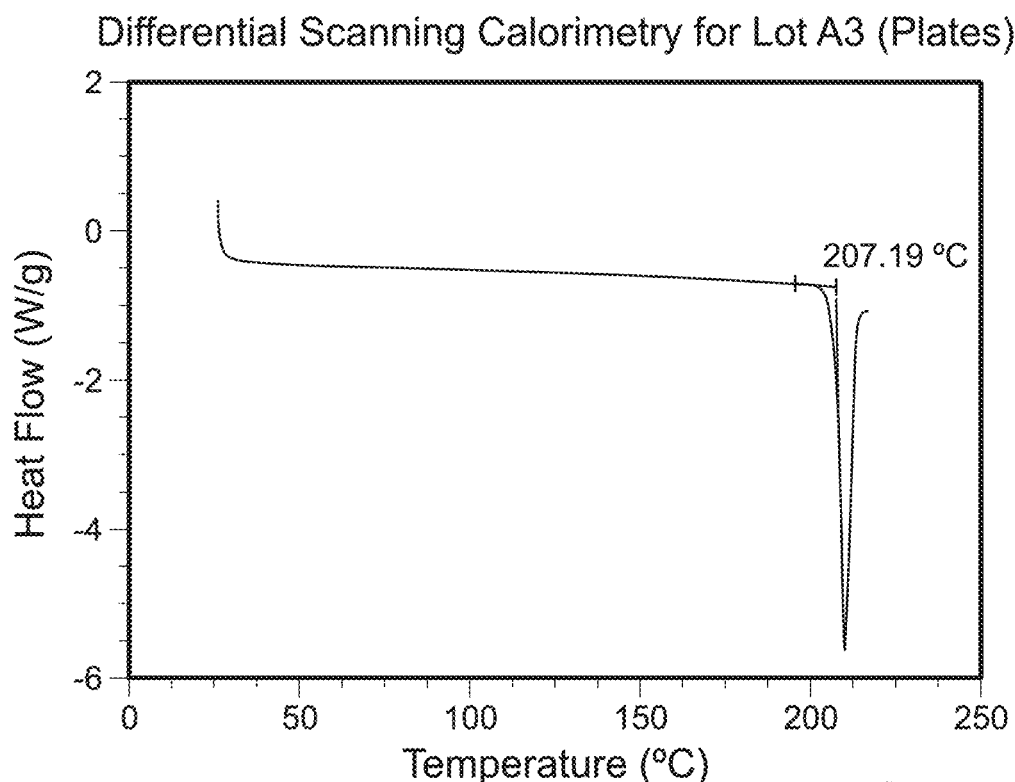
FIG. 8 shows a differential scanning calorimetry (DSC) thermogram for Lot A3 (plates) as described in Example 3.
Figure 9:
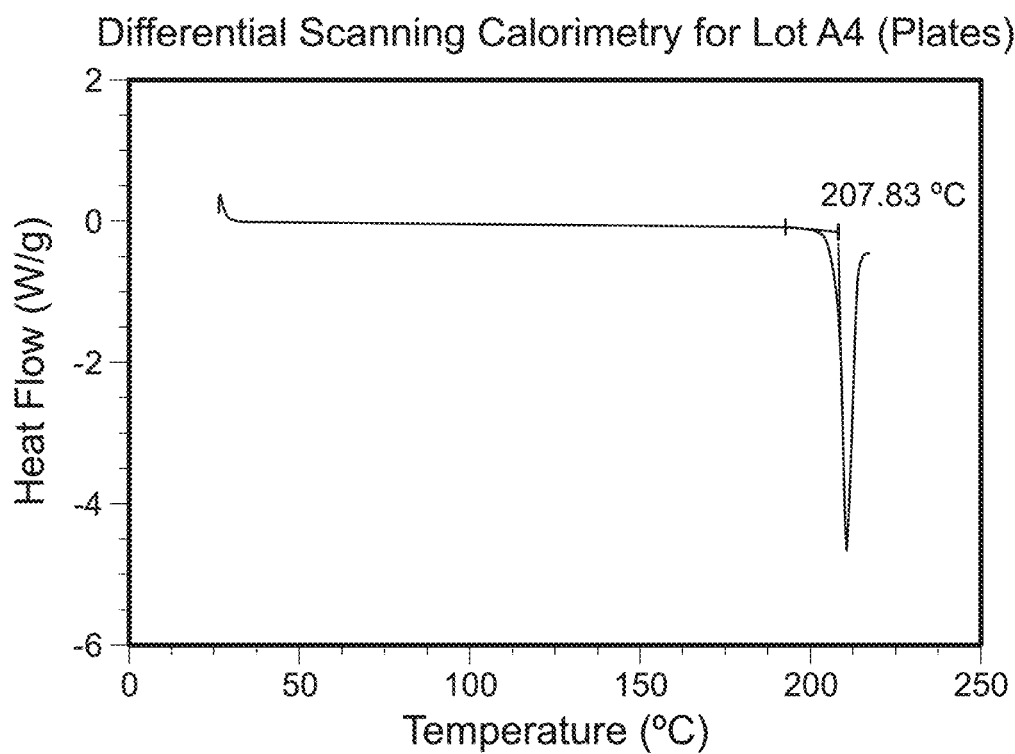
FIG. 9 shows a differential scanning calorimetry (DSC) thermogram for Lot A4 (plates) as described in Example 3.
Figure 10:
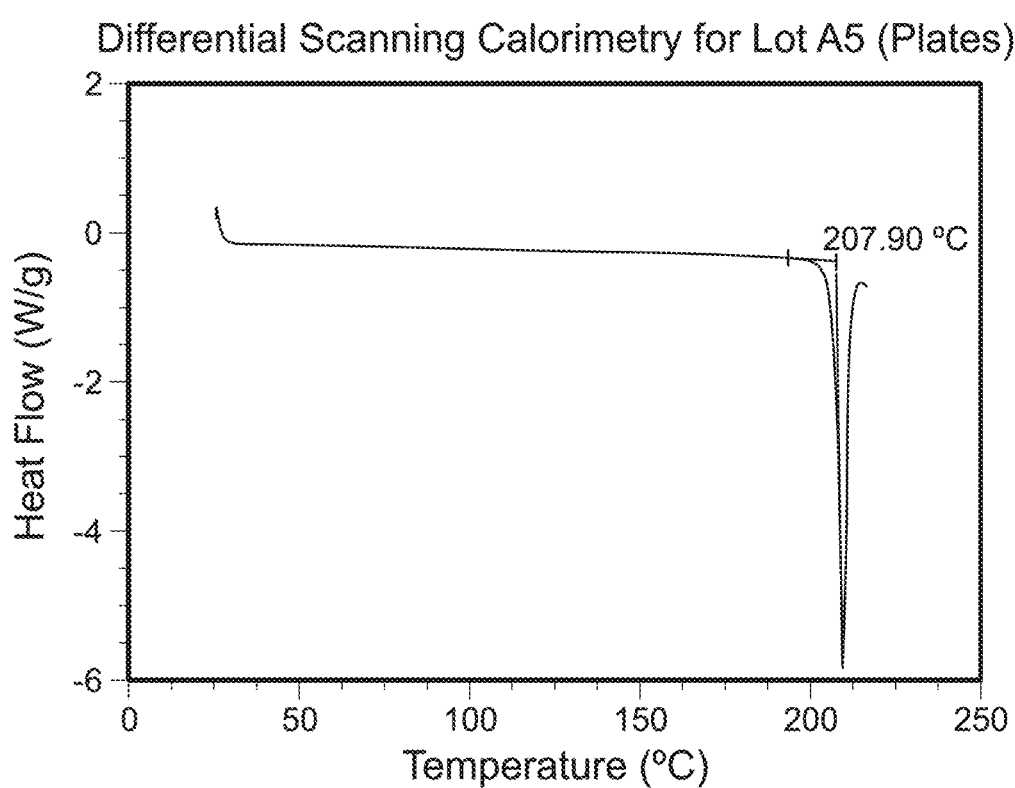
FIG. 10 shows a differential scanning calorimetry (DSC) thermogram for Lot A5 (plates) as described in Example 3.

| L-Arginine Salt Lot Number | DSC Onset Temperature | Differential Scanning Calorimetry | Isolated Morphology |
|---|---|---|---|
| A1 [a] | 208.09° C. | FIG. 6 | Plates |
| A2 [a] | 207.20° C. | FIG. 7 | Plates |
| A3 [b] | 207.19° C. | FIG. 8 | Plates |
| A4 [a] | 207.83° C. | FIG. 9 | Plates |
| A5 [a] | 207.90° C. | FIG. 10 | Plates |

[a] Prepared using a similar process as described in Example 3
[b] Prepared as specifically described in Example 3

Example 4: Preparation of a Crystalline Plate Habit or Morphology of L-Arginine Salt of (R)-2-(7-(4-Cyclopentyl-3-(trifluoromethyl)benzyloxy)-1,2,3,4-tetrahydrocyclopenta[b]indol-3-yl)acetic Acid from (R/S)-Ethyl 2-(7-(4-Cyclopentyl-3-(trifluoromethyl) benzyloxy)-1,2,3,4-tetrahydrocyclo-penta[b]indol-3-yl)acetate Three methods, referred to as Method 1, Method 2, and Method 3, are described in this example. In each method, the crystalline free-plate habit of the L-arginine salt of (R)-2-(7-(4-cyclopentyl-3-(trifluoromethyl)benzyloxy)-1,2,3,4-tetrahydrocyclopenta[b]indol-3-yl)acetic acid was prepared by enzymatic hydrolysis of the corresponding (R/S)-ethyl ester to the (R)-acid followed by a modified L-arginine salt-forming procedure compared to what was previously disclosed in WO2011/094008. Thereafter, these methods describe isolating the L-arginine salt directly as the crystalline free-plate habit without a recrystallization step.

These methods allow for the direct isolation of the crystalline free-plate habit of the L-arginine salt of (R)-2-(7-(4-cyclopentyl-3-(trifluoromethyl)benzyloxy)-1,2,3,4-tetrahydrocyclopenta[b]indol-3-yl)acetic acid starting from the corresponding (R/S)-ethyl ester without any direct isolation of any intermediate.

Example 4.1: Method 1, Preparation of a Crystalline Plate Morphology of L-Arginine Salt of (R)-2-(7-(4-Cyclopentyl-3-(trifluoromethyl)benzyloxy)-1,2,3,4-tetrahydrocyclopenta[b]-indol-3-yl)acetic Acid A solution containing 942 mg (6.92 mmol) of potassium phosphate monobasic dissolved in 7.0 g of water was added to a solution of potassium phosphate dibasic containing 12.0 g (68.90 mmol) dissolved 69.2 g of water. A check of the buffer solution gave a typical pH of 7-8.

To a magnetically stirred two liter two neck round bottom flask was added (R/S)-ethyl 2-(7-(4-cyclopentyl-3-(trifluoromethyl)benzyloxy)-1,2,3,4-tetrahydrocyclo-penta[b]indol-3-yl)acetate (100.0 g, 206.0 mmol) and acetonitrile (700.0 g, 886 mL) to form a slurry. The flask was fitted with a reflux condenser and a nitrogen pad. To the slurry was added the potassium phosphate buffer solution followed by 4.0 g of Lipase B, *Candida antarctica*, immobilized. A check of the pH gave a typical reading of 7-8. The reaction mixture was heated to a 40° C. to 45° C. internal temperature until (R)-2-(7-(4-cyclopentyl-3-(trifluoromethyl)benzyloxy)-1,2,3,4-tetrahydrocyclo-penta[b]indol-3-yl)acetic acid was present in an amount >45% area (but less than 50% area) by HPLC. The reaction mixture was adjusted to a pH 4 to 5 by slow addition of a solution containing 9.0 g (46.84 mmol) of citric acid dissolved in 47.0 g of water. The solids were filtered off and washed with 150 g (190 mL) of acetonitrile. The filtrates were combined and concentrated to 101 g using a rotary evaporator under vacuum (bath at 55° C., pressure dropping to 25 mmHg). The residue was dissolved in 200 g (222 mL) of ethyl acetate. With good stirring, 200 g of water were added followed by 39.5 g of saturated sodium chloride brine. After stirring for 5 minutes the phases were allowed to separate and the organics were washed with a sodium chloride solution (3×150 mL, each solution prepared using 100 mL of saturated sodium chloride and 50 mL water). The organics were concentrated to 107 g using a rotary evaporator under vacuum (bath at 55° C., pressure dropping to 20 mmHg). The residue was dissolved in 80 g (101 mL) of 2-propanol and concentrated to 140 g using a rotary evaporator under vacuum (bath at 55° C., pressure dropping to 20 mmHg). The residue was diluted with 2-propanol to a weight of 300 g (160 g of 2-propanol, 202 mL, was added). The solution was passed through a medium porosity filter and then transferred to a one liter jacketed reaction vessel. The reaction vessel was equipped with an overhead stirrer, curved stir paddles, reflux condenser, internal temperature probe, and Mini Huber recirculating heating/cooling control. An additional 100 g of 2-propanol were used in transfer. The product solution, which contained a total of 300 g (379.7 mL) 2-propanol was clear, containing no detectable solids or cloudiness. To the stirred solution was added 23.4 g of water followed by solid L-arginine 17.94 g, (103.0 mmol, 0.5 eq. based on (R/S)-ethyl ester). The reaction mixture was heated to an internal temperature of 40° C. The reaction mixture changed consistence after 5 minutes and then the mixture was heated to an internal temperature of 76° C. To the slurry was added water drop-wise until nearly all the solids were in solution (31.5 g). The internal temperature was adjusted to 80° C. to form a solution. With the internal temperature at 83° C., 3.3 g of the L-arginine salt were added for seeding. The L-arginine salt dissolved into the solution. The resulting stirred solution was cooled to an internal temperature of 70° C. and 2-propanol was added drop-wise until the solution became cloudy (40.3 g added over 20 minutes). The mixture was heated to an internal temperature of 75° C.-80° C. and a clear solution formed. To the solution, an additional amount of 1.2 g of the L-arginine salt was added for seeding. To the seeded mixture, 2-propanol was added drop-wise (45 g over 90 minutes). The resulting slurry was held at 80° C. for 10 minutes before restarting the drop-wise addition of 2-propanol. Three additions (79.0 g, 78.5 g, and 79.1 g) were done each taking approximately 75 minutes with 10 minute holds between. After the last addition, the temperature controller was programed to cool the jacket from 85° C. to 20° C. over 6 hours and hold.

Figure 11:
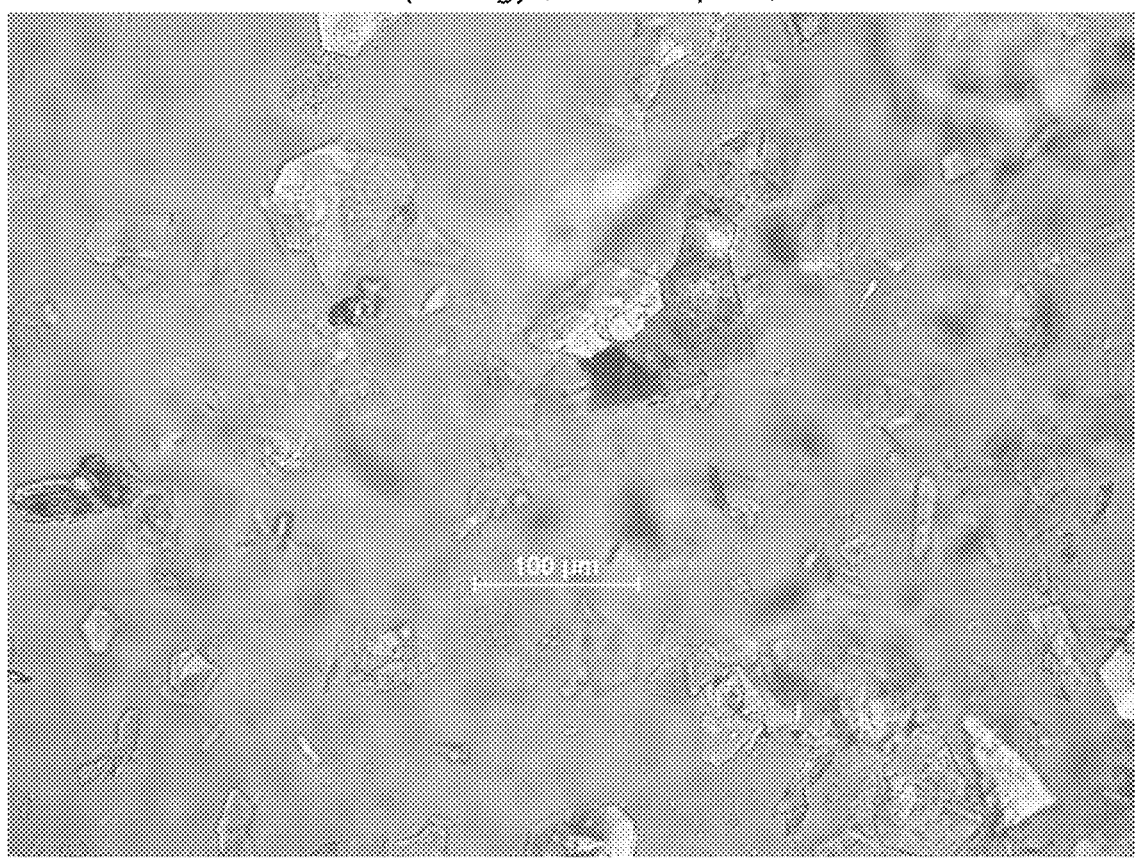
FIG. 11 shows a micrograph of the crystal plate morphology as described in Example 4.1, Method 1 using polarized light microscopy (PLM).

The stirred mixture was subjected to two cycles of heating to an internal temperature of 70° C. to 72° C. and cooling to 20 over 4 hours. After the second cycle the mixture was held at 20° C. and a sample was checked by PLM. The PLM showed only plates (see FIG. 11). The mixture was heated to an internal temperature of 55° C. to 60° C., held for 1 hour and then cool slowly (3 hours) to 30° C. After a 30 minute hold, the mixture was heated to 50° C. to 55° C., held for 1 hour and then cooled slowly (3 hours) to 20° C. and held.

Figure 12A:
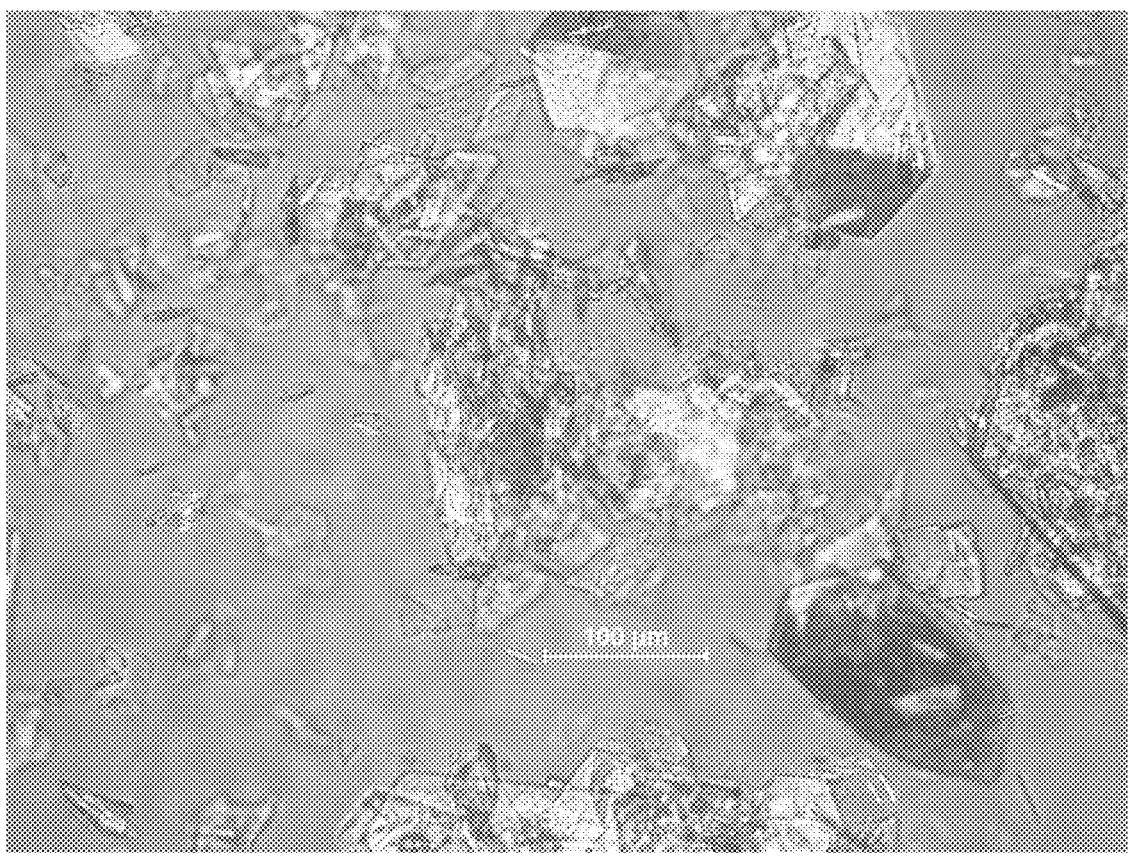
FIG. 12A shows a micrograph of the crystal plate morphology as described in Example 4.1, Method 1 using polarized light microscopy (PLM).
Figure 12B:
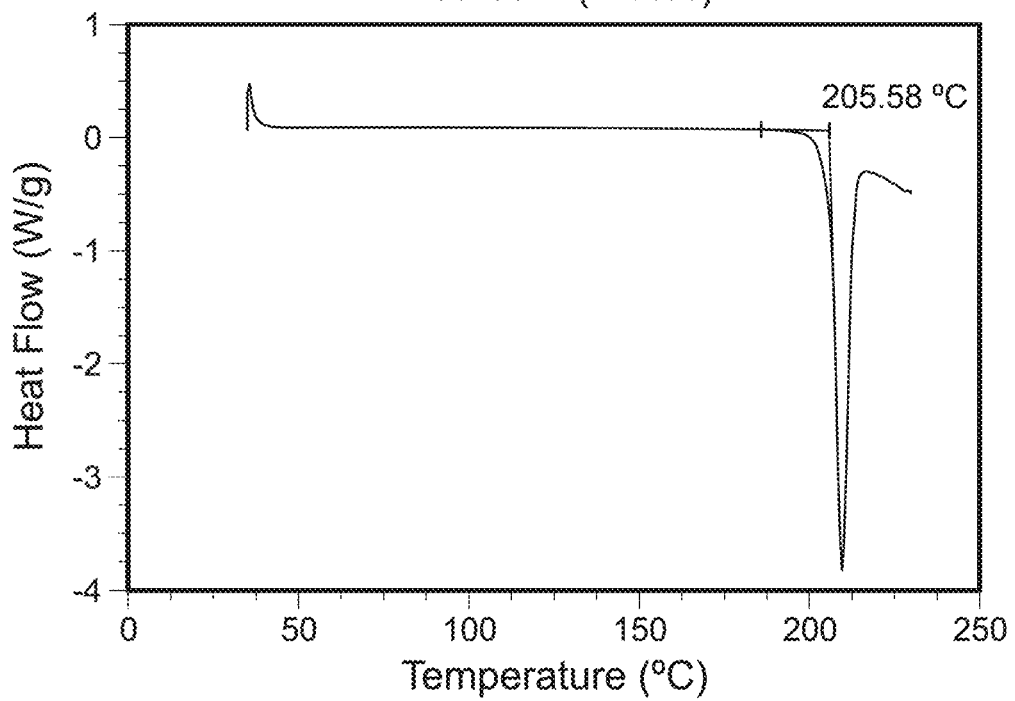
FIG. 12B shows a differential scanning calorimetry (DSC) thermogram for a sample from Example 4.1, Method 1 (plates).

The solids were isolated by filtration using a medium porosity filter paper and a slight pressure reduction (60 mmHg reduction from atmospheric). The filter cake was washed (reslurry) with 125 g of 2-propanol and followed with a displacement wash with 75 g of 2-propanol. The semi-dry cake was washed (reslurry) with 100 g of ethyl acetate followed by displacement wash with 100 g of ethyl acetate. The cake was dried in a vacuum oven (40° C., high house vacuum) to give 65.2 g of the L-arginine salt as an off-white solid (plates, see FIG. 12A) with an onset temperature of 205.6° C. by DSC (FIG. 12B). Yield=100×((65.2 g−4.5 g seeds)/65.05 g=93.3% based on (R)-ethyl 2-(7-(4-cyclopentyl-3-(trifluoromethyl)benzyloxy)-1,2,3,4-tetrahydrocyclo-penta[b]indol-3-yl)acetate (i.e., half of the racemic mixture of the starting material ethyl 2-(7-(4-cyclopentyl-3-(trifluoromethyl)-benzyloxy)-1,2,3,4-tetrahydrocyclopenta[b]indol-3-yl)acetate). Chiral HPLC analysis showed 99.61% area of Compound 1.

Example 4.2: Method 2, Preparation of a Crystalline Plate Morphology of L-Arginine Salt of (R)-2-(7-(4-Cyclopentyl-3-(trifluoromethyl)benzyloxy)-1, 2,3,4-tetrahydrocyclopenta[b]-indol-3-yl)acetic Acid A 1.0M buffer solution (pH of 7-8) was prepared by mixing a solution of potassium phosphate monobasic (942 mg, 6.92 mmol) in 7.0 g of water with a solution containing potassium phosphate dibasic (12.0 g, 68.90 mmol) in 69.2 g of water.

In a magnetically stirred 2-L three necked round bottom flask fitted with a reflux condenser and kept under nitrogen, ethyl 2-(7-(4-cyclopentyl-3-(trifluoromethyl)benzyloxy)-1, 2,3,4-tetrahydrocyclopenta[b]indol-3-yl)acetate (100.0 g, 206.0 mmol, 1.000 equiv.) was suspended in acetonitrile (700.0 g). To the suspension, the 1.0M potassium phosphate buffer solution was added followed by 3.1 g of Lipase B, *Candida antarctica*. A check of pH gave a typical reading of 7-8. The reaction mixture was then heated in an oil bath at 45° C. until (R)-2-(7-(4-cyclopentyl-3-(trifluoromethyl)benzyloxy)-1,2,3,4-tetrahydrocyclo-penta[b]indol-3-yl)acetic acid was greater than 44% area by achiral HPLC.

The reaction mixture was cooled to room temperature and the pH of the reaction mixture was adjusted to 4-5 with a slow addition of a solution containing citric acid (9.0 g, 46.84 mmol) dissolved in 47.9 g of water. The solids were filtered off and washed with acetonitrile (150 g). The filtrates were combined and concentrated to 121.4 g using a rotary evaporator under vacuum (bath at 55° C., pressure dropping to 141 mmHg). The residue was dissolved in 200 g of ethyl acetate. With good stirring, 200 g of water were added followed by 39.5 g of saturated sodium chloride brine. After stirring for 5 minutes, the phases were separated and the organic layer was washed three times sequentially with solutions each containing 100 mL of saturated sodium chloride brine and 50 mL of water. The organics were concentrated to 116.9 g using a rotary evaporator under vacuum (bath at 55° C., pressure dropping to 139 mmHg). The residue was dissolved in 180 g of 2-propanol. The batch was concentrated. The residue was treated again with 180 g of 2-propanol and concentrated to 121.1 g using a rotary evaporator under vacuum (same conditions, performed as an ethyl acetate chase). The residue was diluted with 2-propanol (113 g) to a weight of 234 g. The solution was passed through a medium porosity filter and then transferred to a 1-L jacketed reaction vessel. The reaction vessel was equipped with an overhead stirrer, curved stir paddles, reflux condenser, internal temperature probe, and Mini Huber recirculating heating/cooling control. An additional 2-propanol (187.3 g) was used for rinses and transfer. Total amount of 2-propanol was 300.1 g. Material was a solution.

To the stirred solution, L-arginine (17.94 g, 103.0 mmol, 0.500 equiv. based on (R/S)-ethyl ester) was added followed by 53.8 g of water. The reaction mixture was heated to an internal temperature of 81° C. over 1 h 15 min to provide a clear solution. At this stage, the water content of aqueous 2-propanol mixture was 15.2% w/w. With the internal temperature at 81° C., 2.01 g of seeds (L-arginine salt of Compound 1) were added. The seed crystals did not completely dissolve. The mixture was stirred for 15 minutes at 80° C.-81° C. To the seeded mixture stirred at 150 rpm, 2-propanol was added by a metering pump (329.3 g over 7 h 30 minutes). At this stage, the water content of aqueous 2-propanol mixture is 7.9% w/w. The stir rate was increased to 180 rpm. After the 2-propanol addition, the temperature controller was programed to cool the jacket from 80° C. to 23° C. over 5 hours and hold at 23° C.

Figure 13:
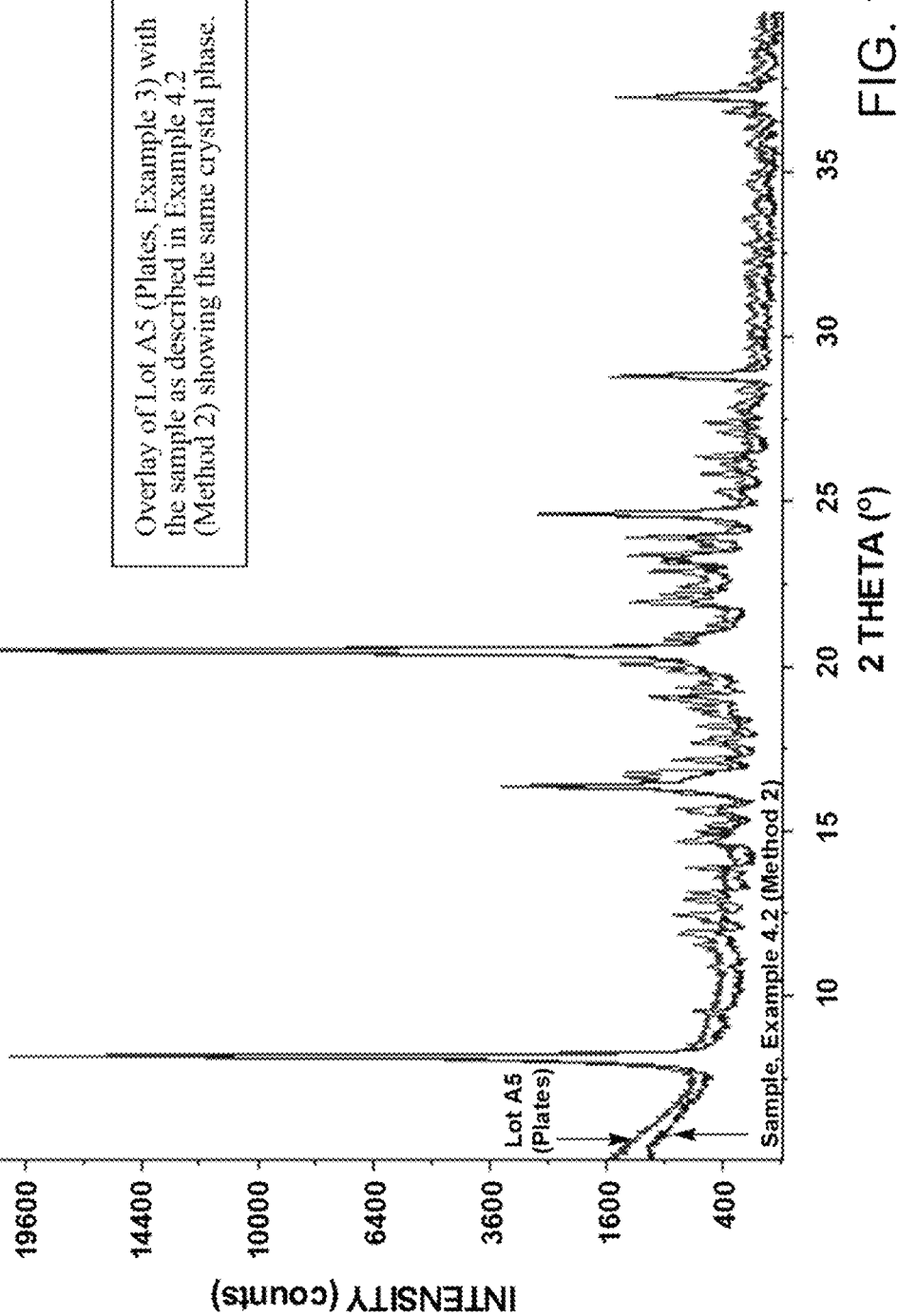
FIG. 13 shows a PXRD pattern overlay for Lot A5 and the sample from Example 4.2, Method 2 showing that the sample has the same crystal phase as the Lot A5 (plates).
Figure 14:
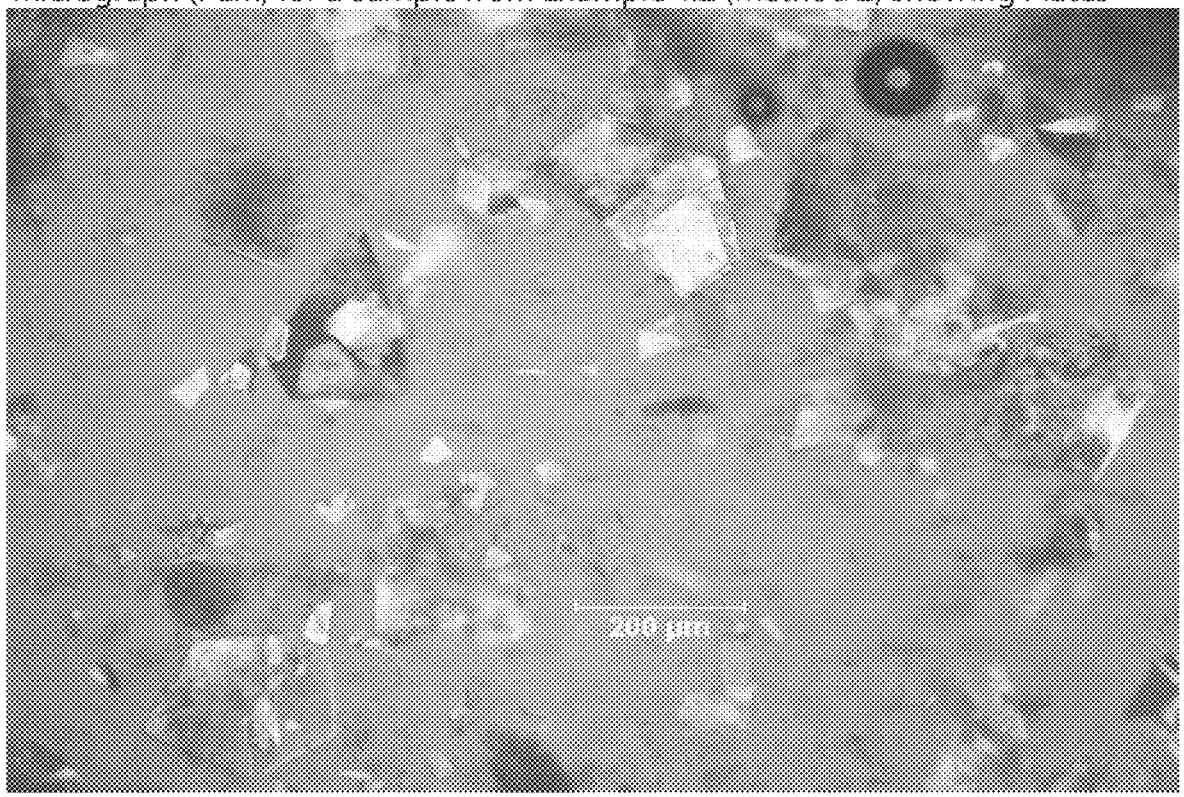
FIG. 14 shows a micrograph for a sample from Example 4.2, Method 2 using polarized light microscopy (PLM). It was observed that the sample consisted predominately as plates.

After overnight stirring, a 500 mg sample of the reaction suspension was centrifuged. The solids were slurried with 0.5 mL of ethyl acetate, centrifuged, and the resultant solids were dried at 40° C. in a vacuum oven at 100 mm Hg. The PXRD overlay of the sample with Lot A5 (plates, see Table A) showed that the sample was the same crystal phase as Lot A5 (FIG. 13). The PLM showed predominantly plate morphology with plates up to ~200 microns by visual observation along with a few aggregates of plates and plate fragments (FIG. 14).

The reaction suspension was subjected to two cycles of heating to an internal temperature of 75° C.-78° C., hold for 45 min, and cooling to 24° C. over 5 hours. After the first cycle a 500 mg sample of the mixture held at 24° C. was centrifuged, and the resultant solids were slurried in 0.5 mL of 2-propanol. The resultant solids obtained by centrifuging off 2-propanol was again slurried in 0.5 mL of ethyl acetate, centrifuged, dried at 40° C. in a vacuum oven at 100 mm Hg, and checked for morphology. PLM showed predominantly plate morphology with a few aggregates. DSC showed a bimodal melt. The mixture in the jacketed reactor was held at 24° C. and at a stir rate of 180 rpm.

The solids were isolated by filtration using a medium porosity filter paper and a slight pressure reduction. The initial deliquoring time was 90 minutes. The filter cake was washed with 79 g of 2-propanol (by a reslurry method) and with 79 g of 2-propanol (by a displacement method). Total deliquoring time for 2-propanol washes was 45 min. The semi-dry cake was washed with 90.2 g of ethyl acetate (by a reslurry method) and with 90.2 g of ethyl acetate (by a displacement wash). Total deliquoring time for ethyl acetate washes was 40 min. The cake was dried in a vacuum oven (at 40° C. and 120 mm Hg) to give 60.4 g (46.45% yield based on (R/S)-ethyl ester used for enzymatic resolution and corrected for added seed amount of L-arginine salt of Compound 1) of the L-arginine salt of Compound 1 as an off-white solid. Chiral HPLC analysis showed 99.78% area of Compound 1.

Example 4.3: Method 3, Preparation of a Crystalline Plate Morphology of L-Arginine Salt of (R)-2-(7-(4-Cyclopentyl-3-(trifluoromethyl)benzyloxy)-1,2,3,4-tetrahydrocyclopenta[b]-indol-3-yl)acetic Acid (Lot 06GSp)

A mixture of (R/S)-ethyl 2-(7-(4-cyclopentyl-3-(trifluoromethyl)benzyloxy)-1,2,3,4-tetrahydrocylopenta[b]indol-3-yl)acetate (100.0 g, 206.0 mmol, 1.000 equiv.), lipase B (4.0 g, Candida antarctica, immobilized), and aqueous potassium phosphate buffer (pH 7.8±0.2, pH=8.0 for this batch) in acetonitrile (886 mL) was stirred under nitrogen at 40° C.±5° C. for at least 6 h (24 h for this batch) and until the concentration of (R)-2-(7-(4-cyclopentyl-3-(trifluoromethyl)benzyloxy)-1,2,3,4-tetrahydrocyclo-penta[b]indol-3-yl)acetic acid was >40 area % by HPLC (48.4 area % for this batch). Subsequently, while the reaction mixture was stirred at 25° C.±5° C., the pH was adjusted to 4 to 5 by addition of aqueous citric acid (9.0 g). After removal of solids by filtration and removal of acetonitrile by vacuum distillation, the product mixture was partitioned between ethyl acetate (222 mL) and water (200 mL). The ethyl acetate phase was washed with brine at least twice and until the pH was greater than or equal to 4. Ethyl acetate was replaced with isopropanol (twice, 101 mL and 202 mL) by vacuum distillation. After complete removal of ethyl acetate (verified by GC≤0.5 area %, 0.41% for this batch), the isopropanol solution of product was heated to 60° C.±5° C., then cooled to ≤40° C., filtered and analyzed by HPLC to determine the concentration of (R)-2-(7-(4-cyclopentyl-3-(trifluoromethyl)benzyloxy)-1,2,3,4-tetrahydrocyclo-penta[b]indol-3-yl)acetic acid (free carboxylic acid). Isopropanol was added or removed (vacuum distilled) to provide a solution of the (R)-free carboxylic acid in isopropanol with a concentration in the range of 11-14 wt %, for this batch the concentration was 12.4%.

The isopropanol product solution was treated with the calculated amount of water (23 g) and L-arginine (15.9 g) and heated to 83° C.±2° C. At this temperature, water (28.1 g) was added until the solids dissolved. Subsequently, the solution was cooled to 73° C.±2° C. and was treated with isopropanol (26.1 g) to obtain a hazy solution. The solution was heated to 75° C.±2° C. and seed crystals of the L-arginine salt of (R)-2-(7-(4-Cyclopentyl-3-(trifluoromethyl)benzyloxy)-1,2,3,4-tetrahydrocyclopenta[b]-indol-3-yl)acetic acid (1.2 g) were added. To the seeded mixture was added isopropanol (280 g) over at least 1 h. Then, the reaction mixture was cooled to 20° C.±2° C. within 6 h.

The heating/cooling cycles were conducted in the following manner. The stirred product mixture was heated to 71° C.±2° C. and then cooled over 4 h to 21° C.±2° C. The mixture was then heated to 60° C.±2° C., stirred at that temperature for 60±10 min before being cooled over 3 h to 31° C. f 2° C. After stirring at 31° C.±2° C. for 25±5 min, the stirred mixture was heated to 50° C.±2° C., stirred at that temperature for 45±5 mini, and then cooled over 3 h to 20° C.±2° C. The heating/cooling cycles can be represented as 71° C. to 21° C. to 60° C. to 31° C. to 50° C.; temps 2° C. for comparison with the cycles described for other lots shown in TABLE 2A. Stirring at 20° C.±2° C. was continued for at least 2 h before suspension was filtered.

The solids were isolated by filtration (filtration was observed to be good), the filtercake was washed first by reslurrying with isopropanol (100 g), then by displacement with isopropanol (100 g), next by reslurrying with ethyl acetate (100 g), and finally by displacement with ethyl acetate (100 g). No single impurity was detected by HPLC analysis >1.0 area/o. The product was vacuum dried at 40° C.±5° C. until loss on drying (LOD) was passed (≤2%, for a 12 h period), providing 54.9 g of the L-arginine salt of (R)-2-(7-(4-Cyclopentyl-3-(trifluoromethyl)benzyloxy)-1,2,3,4-tetrahydrocyclopenta[b]-indol-3-yl)acetic acid as off-white crystalline plates with 100.0 area % by HPLC, L-arginine content of 27.5%, and chiral purity of 99.67%.

Three additional batches were prepared in a manner similar to the above procedure with the following exceptions to the following details shown in TABLE A2.

TABLE A2

|  | Lot 04GSp | Lot 05GSp | Lot 07GSp |
|---|---|---|---|
| Lipase hydrolysis conditions | 20 h, 40° C. ± 5° C. pH = 8.0 (R)-Acid = 47.1 area % | 22 h, 40° C. ± 5° C. pH = 8.0 (R)-Acid = 48.4 area % | 21 h, 40° C. ± 5° C. pH = 8.0 (R)-Acid = 47.9 area % |
| Concentration: (R)-Acid in IPA | 12.4 w/w % | 12.4 w/w % | 11.7 w/w % |
| Heating/Cooling Cycles | A | A | B |
| Product Filtration | Good | Good | Good |
| Final L-Arg Salt of (R)-Acid | 99.8 area % (purity) Yield: 54.9 g Off-white crystalline plates L-Arg content: 30.1% Chiral Purity: 99.63% | 99.8 area % (purity) Yield: 56.9 g Off-white crystalline plates L-Arg content: 27.8% Chiral Purity: 99.52% | 100.0 area % (purity) Yield: 54.7 g Off-white crystalline plates L-Arg content: 27.4% Chiral Purity: 99.62% |

A = 70° C. to 20° C. to 70° C. to 20° C. to 60° C. to 31° C. to 50° C.; temps are ±2° C.
B = 70° C. to 20° C. to 70° C. to 20° C. to 70° C. to 20° C. to 60° C. to 31° C. to 50° C.; temps are ±2° C.

The DSC onset temperatures for all four batches are shown below in TABLE A3.

TABLE A3

Figure 22:
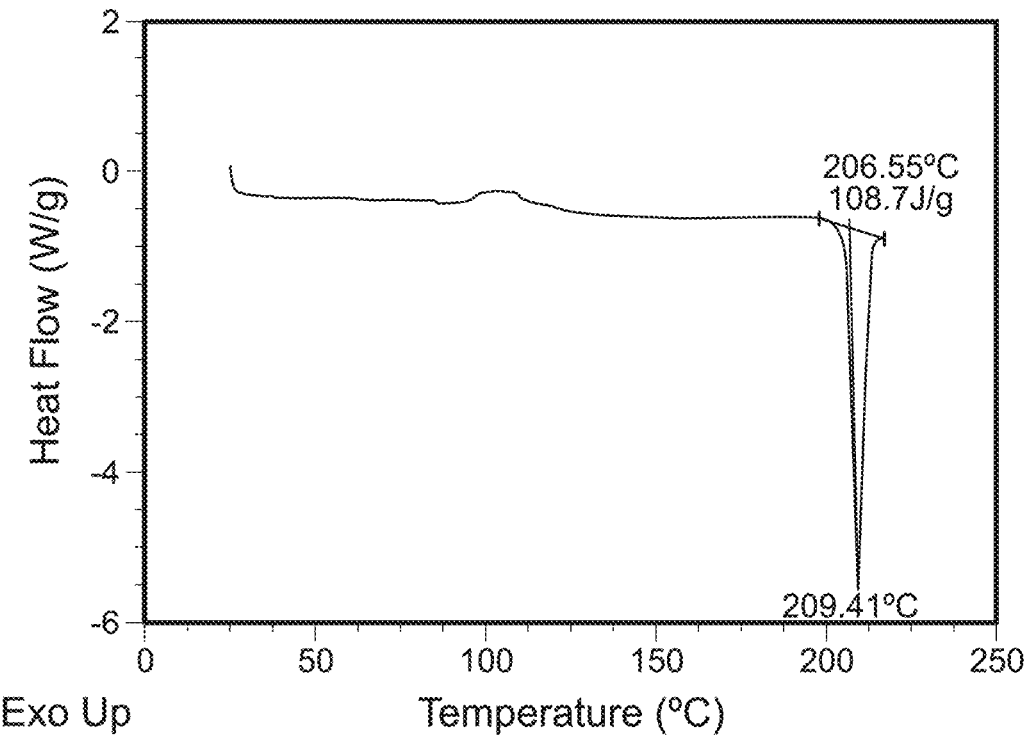
FIG. 22 shows a differential scanning calorimetry (DSC) thermogram for Lot A6 (plates) as described in Example 3.
Figure 23:
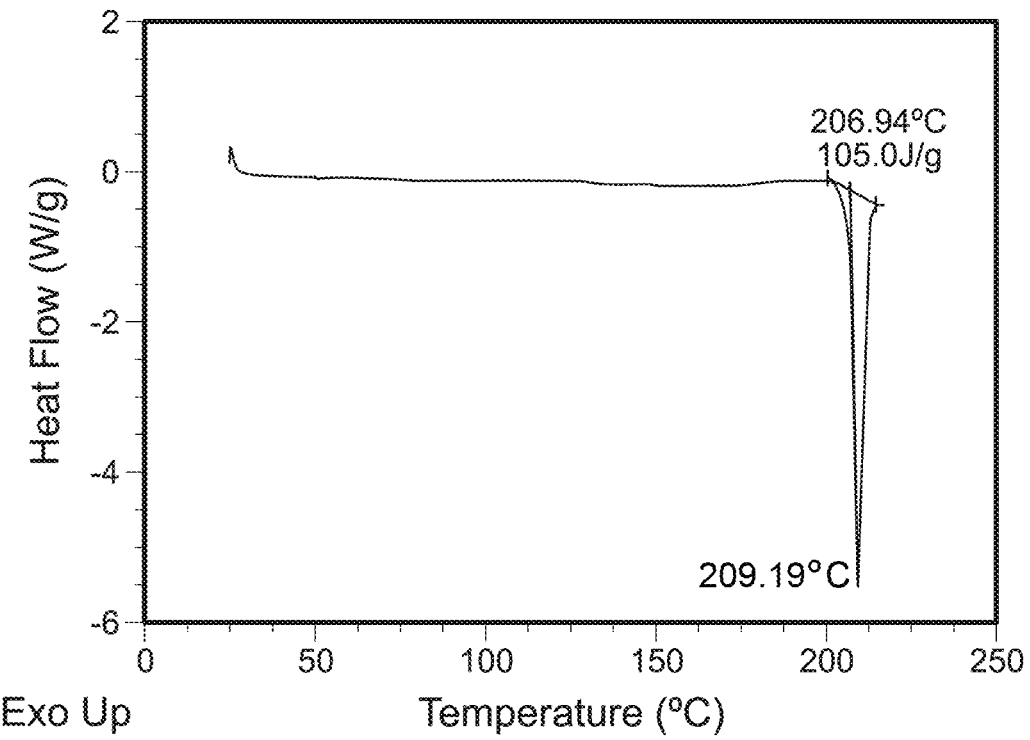
FIG. 23 shows a differential scanning calorimetry (DSC) thermogram for Lot A7 (plates) as described in Example 3.
Figure 24:
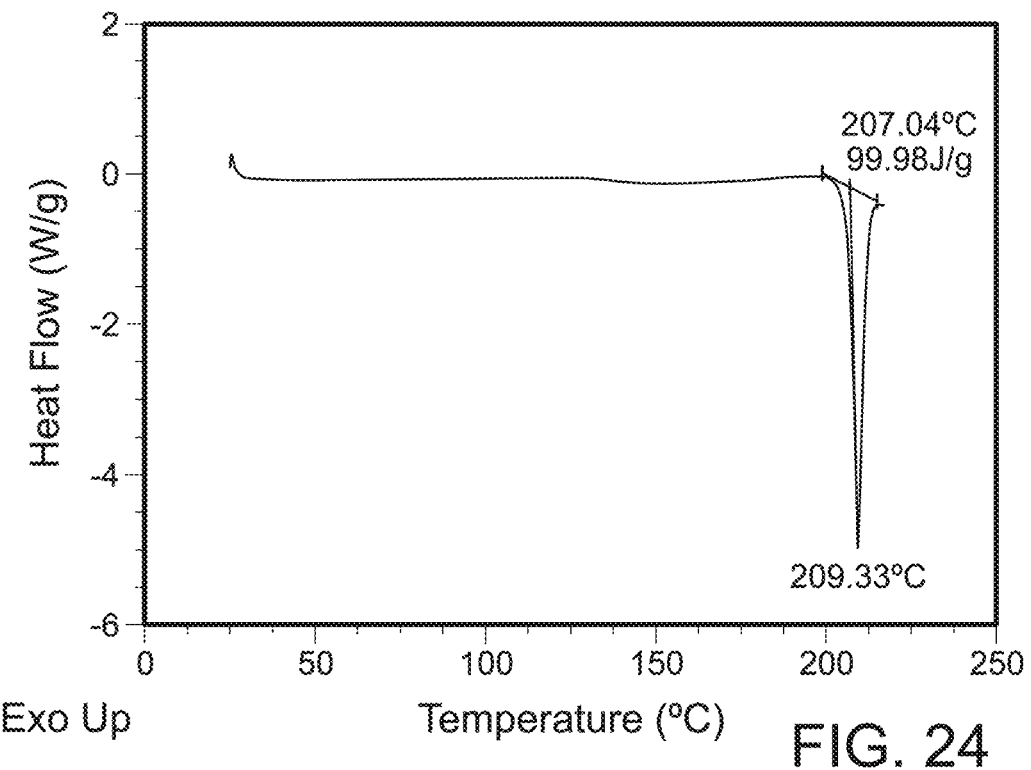
FIG. 24 shows a differential scanning calorimetry (DSC) thermogram for Lot A8 (plates) as described in Example 3.
Figure 25:
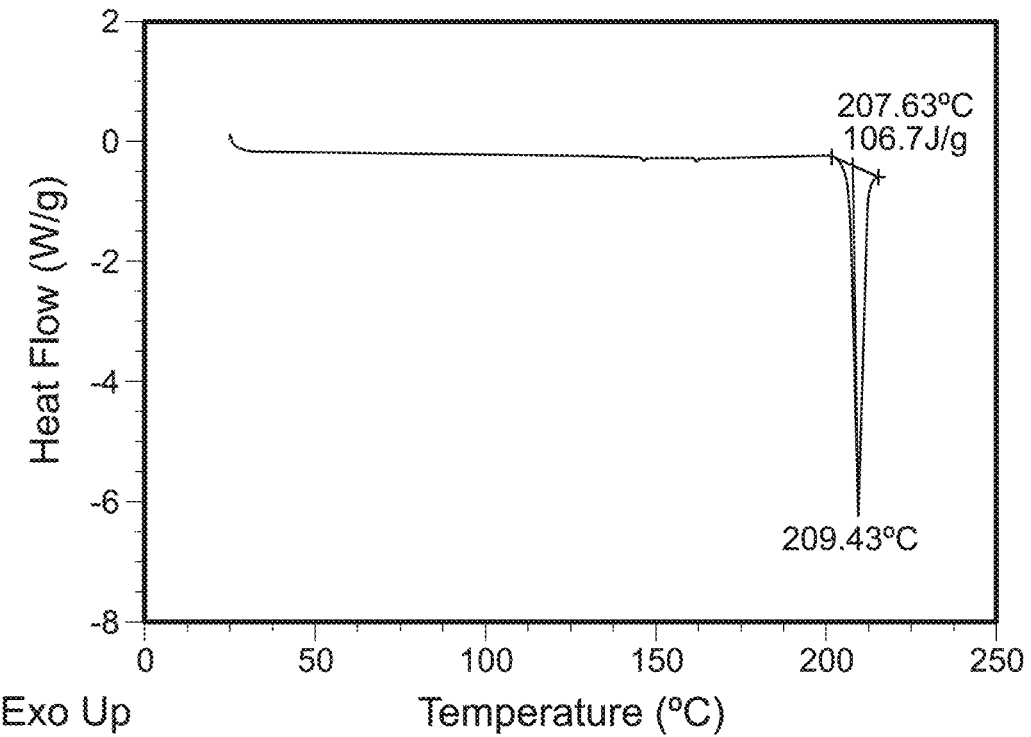
FIG. 25 shows a differential scanning calorimetry (DSC) thermogram for Lot A9 (plates) as described in Example 3.

| Lot No. | L-Arginine Salt Lot Number | DSC Onset Temperature | Differential Scanning Calorimetry | Isolated Morphology |
|---|---|---|---|---|
| 04GSp [b] | A6 | 206.55° C. | FIG. 22 | Plates |
| 05GSp [b] | A7 | 206.94° C. | FIG. 23 | Plates |
| 06GSp [a] | A8 | 207.04° C. | FIG. 24 | Plates |
| 07GSp [b] | A9 | 207.63° C. | FIG. 25 | Plates |

[a] Prepared as described in Example 4.3
[b] Prepared substantially as described for Lot 06GSp and Table A2

Example 5A: Formulations—Evaluation of Spherulites and Plates on Formulation Stability To evaluate the effect the two morphologies, spherulites and plates, had on tablet formulation stability of the L-arginine salt of (R)-2-(7-(4-cyclopentyl-3-(trifluoromethyl)benzyloxy)-1,2,3,4-tetrahydrocyclopenta[b]indol-3-yl)acetic acid, two batches of core tablets were manufactured using the same formulation as described in TABLE B and using the same direct compression process described in FIG. 15.

TABLE B [a]

| Component | Function | % w/w | mg/tab | Batch Weight (g) |
|---|---|---|---|---|
| L-Arg Salt of Compound 1 | API | 1.40 | 1.40 | 7.00 |
| Mannitol 200 SD, USP | Diluent | 54.10 | 54.10 | 270.50 |
| Avicel PH102, NF | Diluent | 40.00 | 40.00 | 200.00 |
| Explotab, NF | Disintegrant | 4.00 | 4.00 | 20.00 |
| Magnesium Stearate, NF | Lubricant | 0.50 | 0.50 | 2.50 |
| Total Core | | 100.00 | 100.00 | 500.00 |

[a] Batch Size (g) = 500; Tablet Weight (mg) = 100

TABLE C and TABLE D summarize the stability results under the accelerated storage conditions. After 6 months at the accelerated conditions, the total impurities (i.e., the sum of the percentages of two impurities, referred to a Cmpd A and Cmpd B) were 0.93% for the spherulite formulation and 0.51% for the plate formulation. The L-arginine salt chemical stability observed in the formulation for the tablets that were manufactured utilizing the plate morphology was improved compared to the L-arginine salt chemical stability observed for the tablets that were manufactured utilizing the spherulite morphology.

Stability data for the spherulite morphology of the L-arginine salt of (R)-2-(7-(4-cyclopentyl-3-(trifluoromethyl)benzyloxy)-1,2,3,4-tetrahydrocyclopenta[b]indol-3-yl)acetic acid after 6 months storage at 40° C./75% RH is shown in TABLE C.

TABLE C

| | | | 40° C./75% RH | | |
|---|---|---|---|---|---|
| | Attribute | Initial | 1 Month | 3 Months | 6 Months |
| Stability Data Spherulite Morphology | % Label | 96.9 | 97.9 | 96.8 | 94.5 |
| | Cmpd A (%) | 0.06 | 0.17 | 0.68 | 0.61 |
| | Cmpd B (%) | 0.04 | 0.06 | 0.19 | 0.32 |
| | Total Impurities | 0.10 | 0.23 | 0.87 | 0.93 |

Stability data for the plate morphology of the L-arginine salt of (R)-2-(7-(4-cyclopentyl-3-(trifluoromethyl)benzyloxy)-1,2,3,4-tetrahydrocyclopenta[b]indol-3-yl)acetic acid after 6 months storage at 40° C./75% RH is shown in TABLE D.

TABLE D

| Stability Data Plate Morphology | | | | |
|---|---|---|---|---|
| | | 40° C./75% RH | | |
| Attribute | Initial | 1 Month | 3 Months | 6 Months |
| % Label | 99.0 | 98.8 | 101.5 | 97.3 |
| Cmpd A (%) | 0.06 | 0.10 | 0.60 | 0.31 |
| Cmpd B (%) | 0.05 | 0.06 | 0.17 | 0.20 |
| Total Impurities | 0.11 | 0.16 | 0.77 | 0.51 |

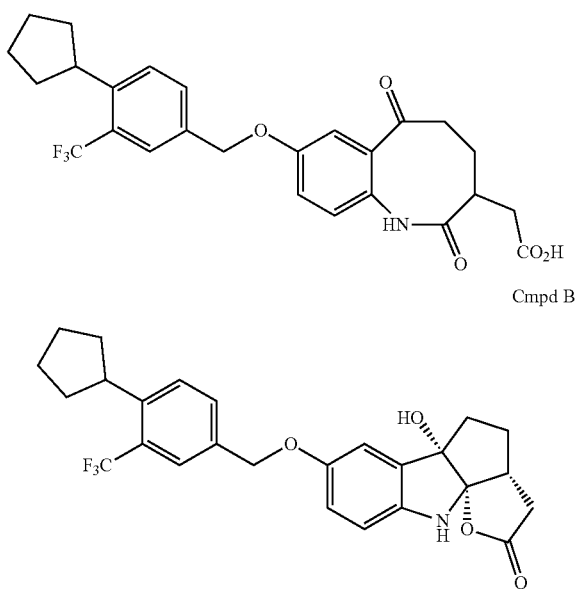

Figure 15:
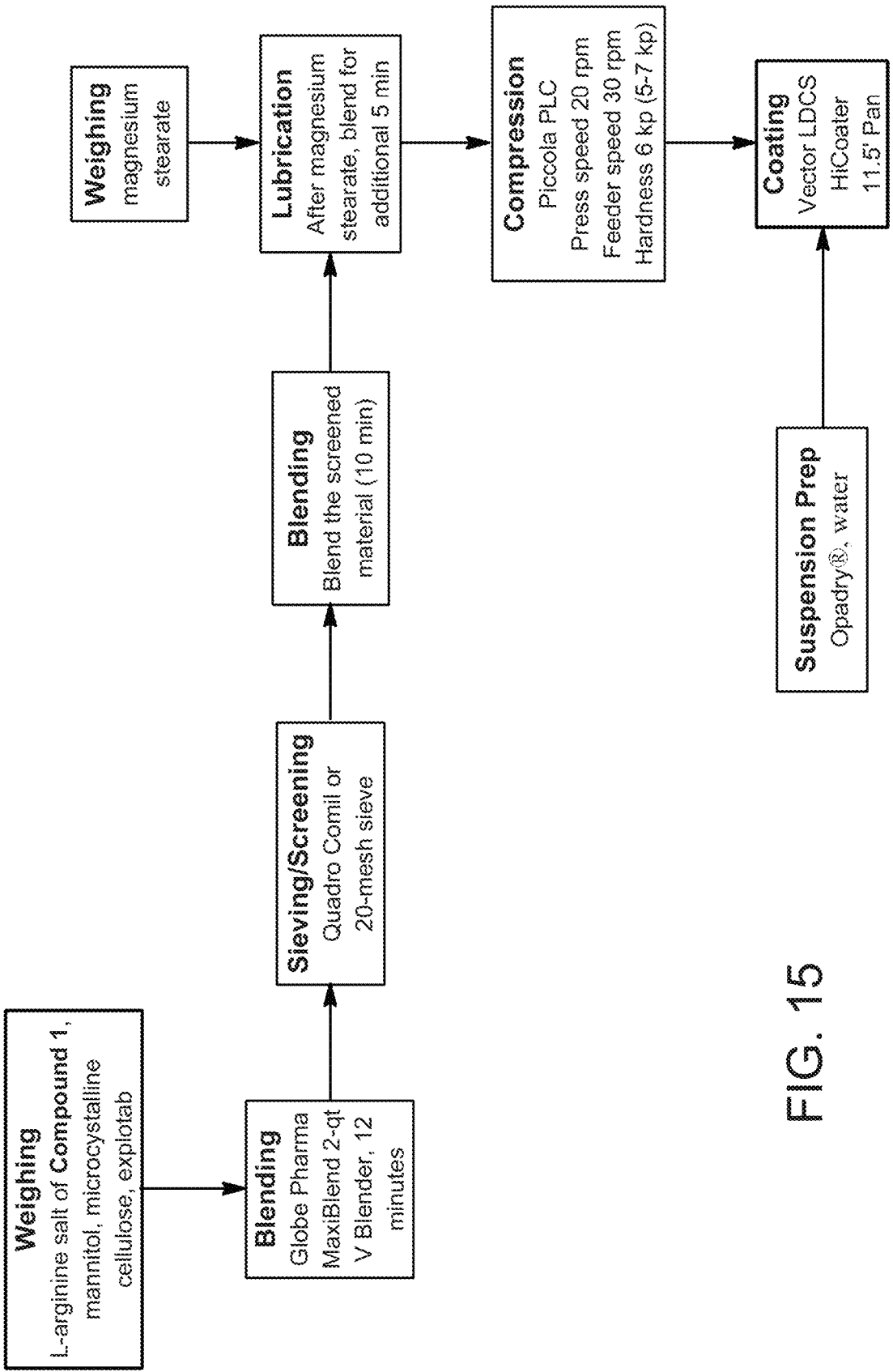
FIG. 15 shows a flowchart for the preparation of core tablets of the L-arginine salt of (R)-2-(7-(4-cyclopentyl-3-(trifluoromethyl)benzyloxy)-1,2,3,4-tetrahydrocyclopenta[b]indol-3-yl)acetic acid (Compound 1).

Two batches of core tablets (1 mg and 5 mg, utilizing the L-arginine salt with the plate morphology) were manufactured using the same formulation as described in Table B (above) and using the same direct compression process described in FIG. 15. Both formulations were packaged in 40 cc HDPE bottles with desiccant. TABLE E and TABLE F show the results of a completed 24 month long-term stability study at 25° C. and 60%

TABLE E

Stability Data (Plate Morphology) for Tablets (1 mg API) after 24 Months

| | | 25° C./60% RH | | | | |
|---|---|---|---|---|---|---|
| Attribute | Initial | 6 Month | 9 Months | 12 Months | 18 Months | 24 Months |
| % Label | 97.5 | 96.8 | 97.2 | 94.5 | 96.5 | 97.2 |
| Cmpd A (%) | 0.11 | 0.18 | 0.20 | 0.21 | 0.22 | 0.25 |
| Cmpd B (%) | <QL | 0.05 | 0.05 | <QL | 0.06 | <QL |
| Total Impurities $^a$ | 0.11 | 0.23 | 0.25 | 0.21 | 0.28 | 0.25 |

$^a$ Sum of percentages of Cmpd A and Cmpd B.
QL = Quantitation Limit (0.05%)

TABLE F

Stability Data (Plate Morphology) for Tablets (5 mg API) after 24 Months

| | | 25° C./60% RH | | | | |
|---|---|---|---|---|---|---|
| Attribute | Initial | 6 Month | 9 Months | 12 Months | 18 Months | 24 Months |
| % Label | 99.8 | 98.8 | 100.2 | 96.8 | 97.5 | 99.3 |
| Cmpd A (%) | 0.06 | 0.12 | 0.13 | 0.16 | 0.17 | 0.19 |
| Cmpd B (%) | <QL | ND | ND | <QL | <QL | <QL |
| Total Impurities $^a$ | 0.06 | 0.12 | 0.13 | 0.16 | 0.17 | 0.19 |

$^a$ Sum of percentages of Cmpd A and Cmpd B.
QL = Quantitation Limit (0.05%);
ND = Not Detected Example 5B: Formulations for L-Arginine Salt of (R)-2-(7-(4-Cyclopentyl-3-(trifluoromethyl)-benzyloxy)-1,2,3,4-tetrahydrocyclopenta[b]indol-3-yl) acetic Acid Core tablets were manufactured using the formulation as described in TABLE G and using substantially the same process described in FIG. 15. The amounts of the L-arginine salt of (R)-2-(7-(4-cyclopentyl-3-(trifluoromethyl)benzyloxy)-1,2,3,4-tetrahydrocyclopenta[b]indol-3-yl)acetic acid were calculated according to the percent of parent being 72.42%

TABLE G

| Tablet Strength | 0.5 mg | 1 mg | 2 mg | 3 mg |
|---|---|---|---|---|
| L-Arg Salt of Compound 1 | 0.69 | 1.381 | 2.762 | 4.143 |
| Mannitol Pearlitol ® 100SD | 54.81 | 54.119 | 52.738 | 51.357 |
| Microcrystalline cellulose-Avicel ® | 40 | 40 | 40 | 40 |
| Sodium Starch Glycolate-Explotab ® | 4 | 4 | 4 | 4 |
| Magnesium Stearate | 0.5 | 0.5 | 0.5 | 0.5 |
| Opadry ® II Blue | 4 | 4 | 4 | 4 |
| Total tablet target weight | 104 | 104 | 104 | 104 |

Figure 16:
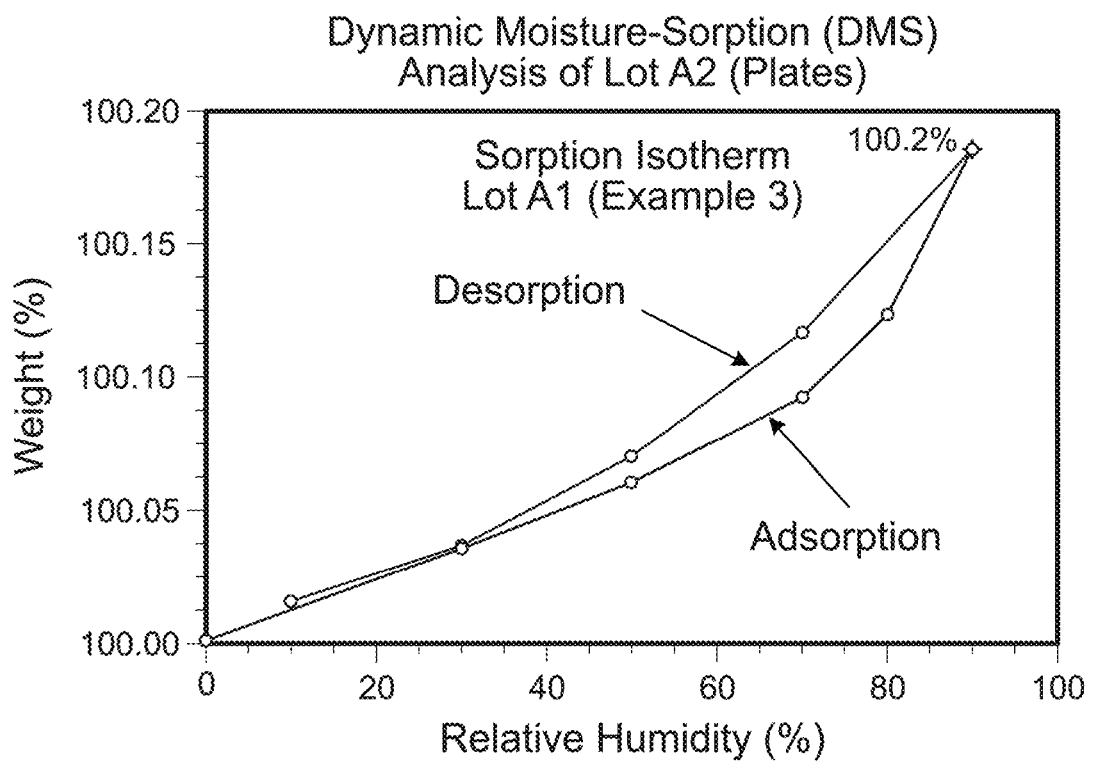
FIG. 16 shows an adsorption phase and a desorption phase from a dynamic moisture-sorption (DMS) analysis for a representative lot having plate morphology (i.e., Lot A2).
Figure 17:
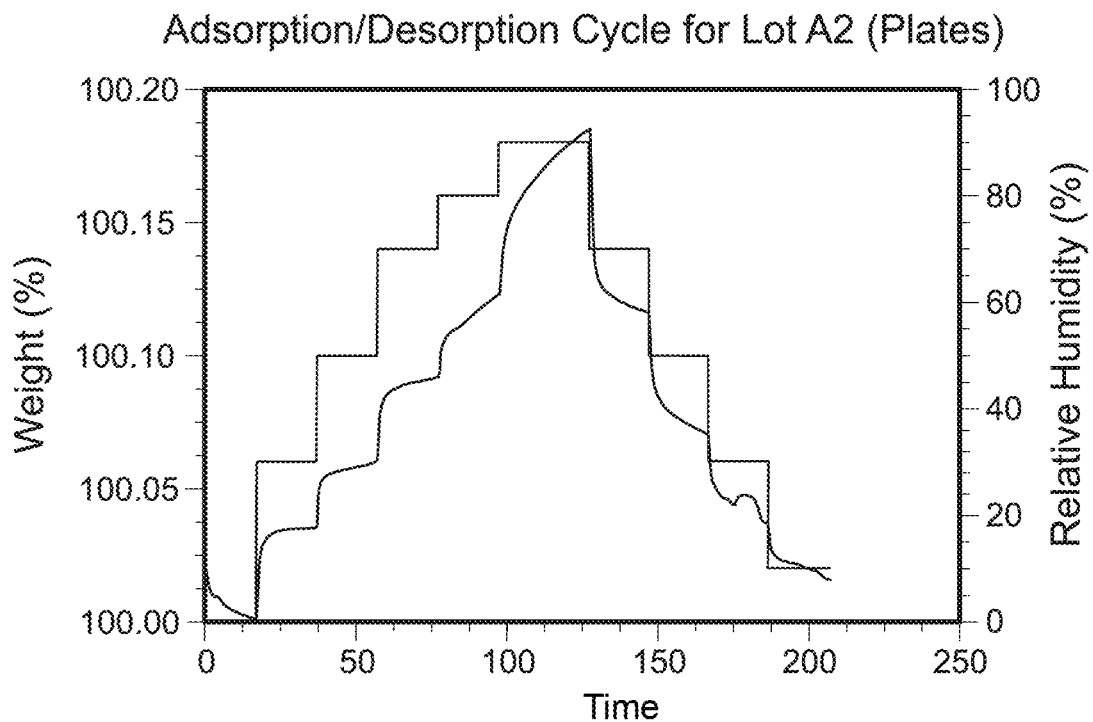
FIG. 17 shows an adsorption/desorption cycle for a representative lot having plate morphology (i.e., Lot A2).

Example 6: Hygroscopicity Comparison Between Plates and Spherulites by Dynamic Moisture-Sorption (DMS) Analysis A dynamic moisture-sorption (DMS) analysis was performed on representative Lot A2 (see, Example 3, TABLE A) of the L-arginine salt of Compound 1 having the plate morphology and representative Lot H2 (prepared in a similar manner as described in Example 8, Method 2 Steps G and H in WO2011/094008; and described in TABLE K, Example 8 herein) of the L-arginine salt of Compound 1 having the spherulite morphology. The DMS analysis was performed at 25° C. and the L-arginine salt of Compound 1 (plate morphology) was shown to be non-hygroscopic, gaining just 0.2% weight at 90% RH (FIG. 16 and FIG. 17). By comparison the L-arginine salt of Compound 1 (spherulite morphology) gained between 0.5% weight (adsorption cycle) and 0.7% weight (desorption cycle) at 90% RH and 25° C. The plate morphology was observed to have improved hygroscopicity compared to the spherulite morphology.

Example 7: Powder X-Ray Diffraction Comparison Between Plates and Spherulites

Figure 18:
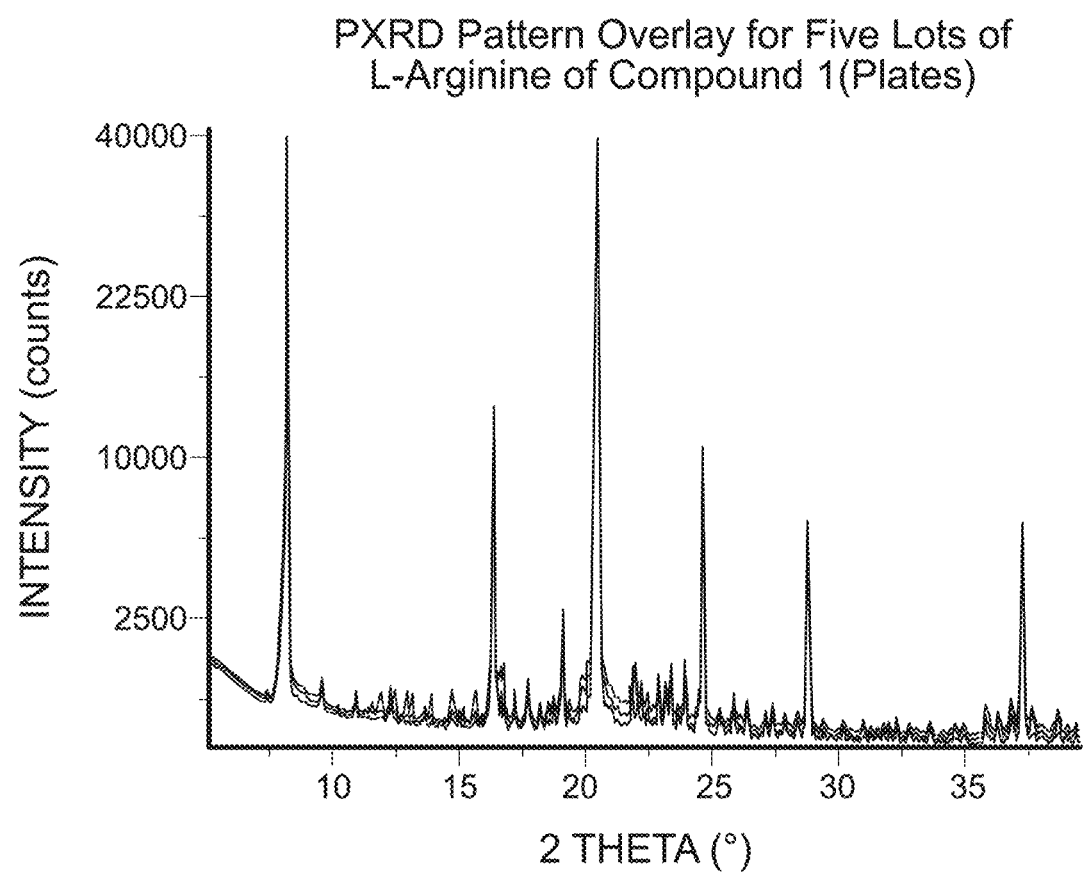
FIG. 18 shows a PXRD pattern overlay for five lots (i.e., A1 to A5, plates) of the L-arginine salt of (R)-2-(7-(4-cyclopentyl-3-(trifluoromethyl)benzyloxy)-1,2,3,4-tetrahydrocyclo-penta[b]indol-3-yl)acetic acid (Compound 1). See Example 3 for additional details.

Powder X-ray diffraction (PXRD) showed that Lots A1 to A5 from Example 3 (see Table A) were crystalline with matching patterns, indicating the same crystal phase (see FIG. 18). A PXRD analysis was performed on representative Lot A2 (see, Example 3, TABLE A) of the L-arginine salt of Compound 1 having the plate morphology and representative Lot H2 (prepared in a similar manner as described in Example 8, Method 2 Steps G and H in WO2011/094008; and described in TABLE K, Example 8 herein) of the L-arginine salt of Compound 1 having the spherulite morphology. Comparing Lot A2 (plate morphology) to Lot H2 (spherulite morphology), it can be seen that both lots share the same crystal phase, however, Lot A2 showed better diffraction and lower background noise (i.e., a lower amorphous halo contribution) indicating a higher degree of crystallinity for the plates compared to the spherulites (FIG. 19).

Certain powder X-ray diffraction peaks for representative Lot A2 of the L-arginine salt of Compound 1 (plates) are shown in TABLE H below.

TABLE H

| Pos. [°2Th.] | Height [cts] | d-spacing [Å] | Rel. Int. [%] |
|---|---|---|---|
| 8.2 | 33633.8 | 10.8159 | 93.6 |
| 14.7 | 402.2 | 6.0252 | 1.1 |
| 15.6 | 364.5 | 5.6724 | 1.0 |
| 16.4 | 4734.0 | 5.4187 | 13.2 |
| 16.6 | 931.2 | 5.3288 | 2.6 |
| 17.2 | 390.6 | 5.1667 | 1.1 |
| 19.1 | 927.9 | 4.6471 | 2.6 |
| 20.1 | 994.1 | 4.4250 | 2.8 |
| 20.5 | 35918.7 | 4.4373 | 100.0 |
| 22.0 | 1056.0 | 4.0463 | 2.9 |
| 22.2 | 645.6 | 4.0046 | 1.8 |
| 22.9 | 811.2 | 3.8855 | 2.3 |
| 23.2 | 671.6 | 3.8404 | 1.9 |
| 23.4 | 1033.2 | 3.8038 | 2.9 |
| 23.9 | 1130.9 | 3.7195 | 3.2 |
| 24.6 | 3586.1 | 3.6159 | 10.0 |
| 25.9 | 356.9 | 3.4455 | 1.0 |
| 26.4 | 363.3 | 3.3785 | 1.0 |
| 28.8 | 1899.7 | 3.1004 | 5.3 |
| 37.3 | 1922.3 | 2.4124 | 5.4 |

Certain powder X-ray diffraction peaks for representative Lot H2 of the L-arginine salt of Compound 1 (spherulites) are shown in TABLE I below.

TABLE I

| Pos. [°2Th.] | Height [cts] | d-spacing [Å] | Rel. Int. [%] |
|---|---|---|---|
| 8.2 | 4469.9 | 10.8266 | 94.9 |
| 11.9 | 1777.7 | 7.4137 | 37.7 |
| 12.5 | 1409.5 | 7.0965 | 29.9 |
| 12.9 | 1340.9 | 6.8507 | 28.5 |
| 13.1 | 1152.3 | 6.7346 | 24.5 |
| 13.9 | 868.3 | 6.3787 | 18.4 |
| 14.7 | 844.0 | 6.0348 | 17.9 |
| 15.6 | 750.7 | 5.6626 | 15.9 |
| 16.6 | 1356.8 | 5.3260 | 28.8 |
| 17.1 | 349.1 | 5.1758 | 7.4 |
| 19.0 | 1954.6 | 4.6610 | 41.5 |
| 20.0 | 1752.3 | 4.4293 | 37.2 |
| 20.5 | 4712.7 | 4.3383 | 100.0 |
| 20.9 | 2525.3 | 4.2584 | 53.6 |
| 22.0 | 1799.9 | 4.0432 | 38.2 |
| 22.6 | 1326.4 | 3.9363 | 28.2 |
| 23.2 | 1686.9 | 3.8367 | 35.8 |
| 24.0 | 912.9 | 3.7137 | 19.4 |
| 24.6 | 953.2 | 3.6193 | 20.2 |
| 25.2 | 386.8 | 3.5281 | 8.2 |
| 28.9 | 90.5 | 3.0857 | 1.9 |
| 30.6 | 167.1 | 2.9198 | 3.6 |

Example 8: Evaluation of Preparations of L-Arginine Salt of (R)-2-(7-(4-Cyclopentyl-3-(trifluoromethyl)benzyloxy)-1,2,3,4-tetrahydrocyclopenta[b]indol-3-yl)acetic Acid Certain processes for the preparation of the L-arginine salt of (R)-2-(7-(4-cyclopentyl-3-(trifluoromethyl)benzyloxy)-1,2,3,4-tetrahydrocyclopenta[b]indol-3-yl)acetic acid have been previously described, see WO2010/011316 (see Example 1.33) and WO2011/094008 (see Example 7, Method 1 Step B; and Example 8, Method 1 and Method 2 Step H).

The L-arginine salt of Compound 1 that was prepared in a similar manner as described in Example 1.33 (WO2010/011316) was observed to have a morphology by PLM as containing aggregates and spherulites along with crystalline fine particles too small to identify the morphology. Overall the sample was poorly crystalline and no plates were observed. The same procedure was also described in WO2011/094008 (see Example 8, Method 1). In this procedure, the L-arginine salt was prepared starting from the substantially pure (R)-2-(7-(4-cyclopentyl-3-(trifluoromethyl)benzyloxy)-1,2,3,4-tetrahydrocyclopenta[b]indol-3-yl)acetic acid.

Figure 20:
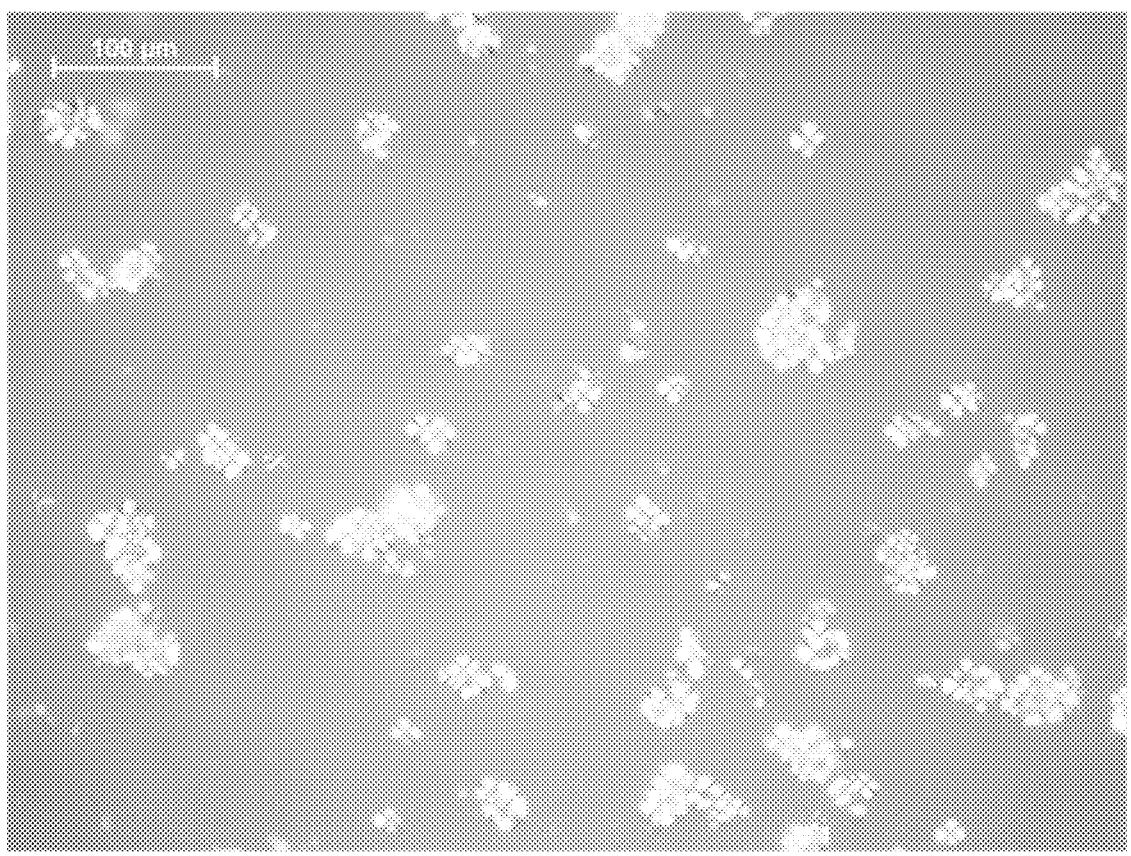
FIG. 20 shows a micrograph for a crystalline sample from Example 7, Method 1 Step B (WO2011/094008) using polarized light microscopy (PLM). The sample was observed to have uniform radial cluster (spherulite) shaped particles with a few fine particles.

The L-arginine salt of Compound 1 prepared from Example 7, Method 1 Step B from WO2011/094008 was observed to have a morphology by PLM as containing spherulites with a few fine particles, see FIG. 20. Based on PLM analysis, the particle size for the sample is described in TABLE J. In this example, the L-arginine salt of Compound 1 was prepared in the presence of the (S)-ethyl ester that remained after the enzymatic hydrolysis step.

TABLE J

| Sample | Mean | St. Dev | Minimum | Maximum |
|---|---|---|---|---|
| Example 7, Method 1 Step B [1] | 18.05 | 12.18 | 5.43 | 58.37 |

[1] WO2011/094008

In a similar manner as described in Example 7 Method 1 Step B, the L-arginine salt of Compound 1 was prepared by starting from (R/S)-ethyl 2-(7-(4-cyclopentyl-3-(trifluoromethyl)-benzyloxy)-1,2,3,4-tetrahydrocyclo-penta[b]indol-3-yl)acetate as described in WO2011/094008, Example 8, Method 2 Steps G and H. Six lots of the L-arginine salt of Compound 1 were prepared with one lot being specifically described in Example 8, Method 2 Steps G and H (i.e., Lot H1) and five additional lots (i.e., Lots H2 to H6) of the L-arginine salt of Compound 1 being prepared using substantially the same procedure. Each lot was observed to have the same crystal phase and spherulite habit with a melting onset temperature ranging from 203.00° C. to 203.97° C. as determined by differential scanning calorimetry (DSC), see TABLE K.

TABLE K

| Lot Number | Morphology | Preparation Method | Onset Melting Temp. (DSC) | Isolated Morphology |
|---|---|---|---|---|
| H1 | Spherulite | WO2011/094008 [1] | 203.46° C. | Spherulite |
| H2 | Spherulite | WO2011/094008 [2] | 203.96° C. | Spherulite |
| H3 | Spherulite | WO2011/094008 [2] | 203.00° C. | Spherulite |
| H4 | Spherulite | WO2011/094008 [2] | 203.11° C. | Spherulite |
| H5 | Spherulite | WO2011/094008 [2] | 203.79° C. | Spherulite |
| H6 | Spherulite | WO2011/094008 [2] | 203.97° C. | Spherulite |

[1] See Example 8, Method 2 Steps G and H
[2] Prepared by a similar process as described for Lot H1

Based on the six lots described in WO2011/094008, four (4) new additional lots (i.e., J1 to J4) were prepared using substantially the same procedure (see Example 2). Each of these new lots started with at least 21.9 Kg of (R/S)-ethyl 2-(7-(4-cyclopentyl-3-(trifluoromethyl)benzyloxy)-1,2,3,4-tetrahydrocyclo-penta[b]indol-3-yl)acetate. Each lot was prepared using the selective enzymatic hydrolysis of (R/S)- ethyl 2-(7-(4-cyclopentyl-3-(trifluoromethyl)benzyloxy)-1,2,3,4-tetrahydrocyclo-penta[b]indol-3-yl)acetate to provide the corresponding (R)-2-(7-(4-cyclopentyl-3-(trifluoromethyl)benzyloxy)-1,2,3,4-tetrahydrocyclopenta[b]indol-3-yl)acetic acid (i.e., Compound 1). In the next step and without direct isolation of Compound 1, to the solution (i.e., comprising Compound 1, (S)-ethyl ester, isopropanol, and water) was added the preheated aqueous solution of L-arginine to form the L-arginine salt of Compound 1. After formation, the crude mixture comprising the L-arginine salt of Compound 1 underwent a series of washes and filtration steps as described in FIG. 21. Two of the four lots (i.e., Lots J1 and J2) were analyzed by microscopy. These two lots were observed to have a different morphology (see Example 2) with respect to each other and each was also observed to be different from the spherulite morphology or habit observed for the six lots described in WO2011/094008.

In addition to the formation of different morphologies, it was also found that each process used to prepare the four lots of the L-arginine salt of Compound 1 from (R/S)-ethyl 2-(7-(4-cyclopentyl-3-(trifluoromethyl)benzyloxy)-1,2,3,4-tetrahydrocyclo-penta[b]indol-3-yl)acetate resulted in a number of undesired process deviations from that seen for the six lots described in WO2011/094008. After formation of the L-arginine salt of Compound 1, the resulting product slurry was transferred to the filter dryer to initiate the series of washes and filtration steps as described in FIG. 21. Unexpectedly, the filtration steps were observed to be excessively long, inefficient, and ultimately blinded off the filter. The filtering inefficiencies led to transferring excessively wet material from the filter dryer to the drying trays thus resulting in further processing delays due to lengthy drying times to achieve specification (i.e., loss on drying ≤2% by weight). Approximate filtration times are shown in TABLE L.

TABLE L

Figure 21:
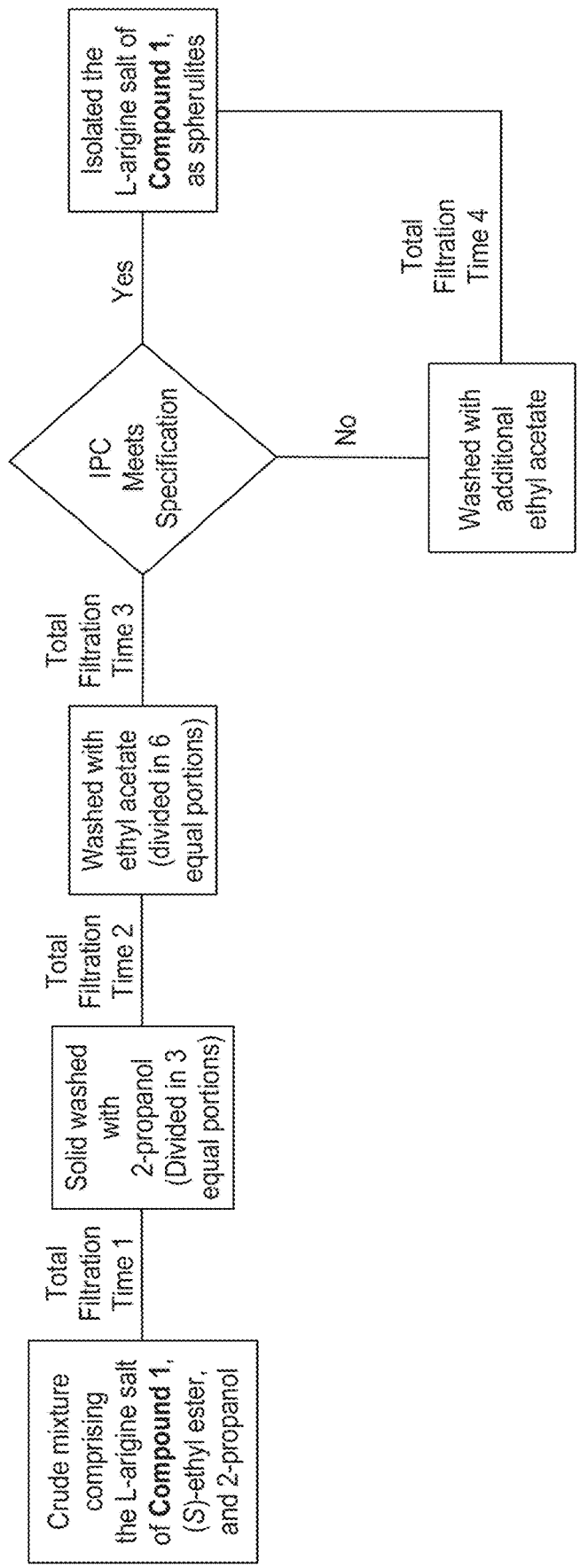
FIG. 21 shows a purification flow chart, see Example 8 for additional details.

See FIG. 21

| Lot No. | Batch Size (Kg) | Total Filtration Time 1 (min) | Total Filtration Time 2 (min) | Total Filtration Time 3 (min) | Total Filtration Time 4 (min) | Total Filtration Time (mm) [1] |
|---|---|---|---|---|---|---|
| J1 | 22.16 | 31 | 82 | 935 | 378 | 1426 |
| J2 [2] | 21.86 | 80 | 228 | 1371 | NR [3] | 1679 |
| J3 | 21.80 | 43 | 703 | 6125 | 564 | 7435 |
| J4 | 22.58 | 43 | 570 | 4643 | 625 | 5881 |

[1] Summation of Total Filtration Times 1 to 4
[2] Prepared as disclosed in Example 2; Lots J1, J3, and J4 were prepared in a similar manner
[3] Not Required Surprisingly, it was found that the novel processes, as described herein, provided the L-arginine salt of Compound 1 as a free-plate habit instead of the morphology observed for the previous lots (i.e., the six (6) lots described in WO2011/094008, see TABLE K; and the two lots analyzed as described above (Lots J1 and J2), see TABLE L). The plate morphology resulted in a number of advantages, such as, improved filtrations, higher degree of crystallinity, improved hygroscopicity, and improved formulation stability.

Example 9: Powder X-Ray Diffraction

Powder X-ray Diffraction (PXRD) data were collected on an X'Pert PRO MPD powder diffractometer (PANalytical, Inc.) with a Cu source set at 45 kV and 40 mA, Cu(Kα) radiation and an X'Celerator detector. Samples were added to the sample holder and smoothed flat with a spatula and weigh paper. With the samples spinning, X-ray diffractograms were obtained by a 12-min scan over the 2-theta range 5-40°2θ. Diffraction data were viewed and analyzed with the X'Pert Data Viewer Software, version 1.0a and X'Pert HighScore Software, version 1.0b.

Example 10: Differential Scanning Calorimetry

Differential scanning calorimetry (DSC) study was conducted using a TA Instruments, Q2000 at a heating rate 10° C./min. The instrument was calibrated for temperature and energy using the melting point and enthalpy of fusion of an indium standard. Thermal events (desolvation, melting, etc.) were evaluated using Universal Analysis 2000 software, version 4.1D, Build 4.1.0.16. Samples were weighed into A1 pans and scans ran from ~25° C. to ~270° C. at a rate of 10° C./min.

Example 11: Thermal Gravimetric Analysis

Thermogravimetric analysis (TGA) was conducted using a TA Instruments TGA Q500 or Q5000 at a heating rate 10° C./min. The instrument was calibrated using a standard weight for the balance, and Alumel and Nickel standards for the furnace (Curie point measurements). Thermal events such as weight-loss are calculated using the Universal Analysis 2000 software, version 4.1D, Build 4.1.0.16.

Example 12: Dynamic Moisture-Sorption Analysis

DMS analysis was performed using a TA Instruments Q5000 SA (EQ2418). Instrument performance was verified in-house. Samples were added to a tared sample holder on the Q5000 SA balance. The sample was dried at 40° C. and then analyzed at 25° C. with an adsorption phase from 30% RH to 90% RH and a desorption phase from 90% RH to 10% RH.

Example 13: Microscopy

Microscopy was performed using a Nikon Eclipse E600 POL (EQ0124), with a Nikon DS Fil digital camera (EQ0123). Nikon (NIS-Elements BR 3.0) software program was used to collect photomicrographs. Instrument performance was verified in-house. Samples were prepared by placing a small amount of solid on a glass slide, adding a drop of mineral oil to a glass cover slip, placing the oil and cover slip on the sample, and gently pressing down with a gloved finger.

Example 14: BET (Brunauer, Emmett, and Teller) Specific Surface Area Method

In general, the specific surface areas for Lots A1-A9 (plates) and H1-H6 (spherulites) were determined by physical adsorption of nitrogen gas on the surface of the sample from each lot using the well-established technique based on the Brunauer, Emmett, and Teller theory.

The BET surface areas for the samples were measured by Micromeritics Pharmaceutical Services using a Micromeritics™ TriStar II BET surface area analyzer (MicroActive for TriStar II Plus 2.02 Software™). The samples were degassed at 25° C. for 960 minutes under vacuum (i.e., 100 mm/Hg). The determination of the adsorption of $N_2$ at 77.3 K was measured using a BET surface area eleven point method with relative pressures in the range of about 0.05 to about 0.3 (P/P$_0$) for a weighed amount of each sample, see TABLE M1, TABLE M2, and TABLE N below. The analysis was performed per ISO9277.

TABLE M1

| | | Plate Morphology | | |
|---|---|---|---|---|
| Arena Lot | Lot Number | Sample (g) | Correlation Coefficient | BET Surface Area (m$^2$/g) |
| 5015-12-12 | A1 | 0.6163 | 0.99916 | 0.7 |
| 5015-12-13 | A2 | 1.5270 | 0.99945 | 0.7 |
| 5015-12-14 | A3 | 0.4465 | 0.99922 | 1.5 |
| 5015-12-15 | A4 | 0.5709 | 0.99939 | 1.0 |
| 5015-12-16 | A5 | 0.9582 | 0.99940 | 0.8 |

TABLE M2

| | | Plate Morphology | | |
|---|---|---|---|---|
| Lot No. | Lot Number | Sample (g) | Correlation Coefficient | BET Surface Area (m$^2$/g) |
| 04GSp | A6 | 0.4332 | 0.99921 | 2.4 |
| 05GSp | A7 | 0.3652 | 0.99910 | 1.9 |
| 06GSp | A8 | 0.6866 | 0.99984 | 3.0 |
| 07GSp | A9 | 0.2754 | 0.99914 | 3.1 |

TABLE N

| | | Spherulite Morphology | | |
|---|---|---|---|---|
| Arena Lot | Lot Number | Sample (g) | Correlation Coefficient | BET Surface Area (m$^2$/g) |
| 5015-10-01 | H1 | 0.8891 | 0.99967 | 10.0 |
| 5015-10-02 | H2 | 0.6766 | 0.99967 | 13.5 |
| 5015-10-03 | H3 | 0.7002 | 0.99966 | 11.8 |
| 5015-10-04 | H4 | 0.9420 | 0.99964 | 12.0 |
| 5015-10-05 | H5 | 0.7658 | 0.99955 | 10.9 |
| 5015-10-06 | H6 | 0.9662 | 0.99965 | 12.3 |

Those skilled in the art will recognize that various modifications, additions, substitutions, and variations to the illustrative examples set forth herein can be made without departing from the spirit of the invention and are, therefore, considered within the scope of the invention.

What is claimed is:

1. A method for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid that is substantially free of radial clusters or spherulites, said method comprising the steps of:
   a) forming a first mixture comprising L-arginine salt of (R)-2-(7-(4-cyclopentyl-3-(trifluoromethyl)benzyloxy)-1,2,3,4-tetrahydrocyclopenta[b]indol-3-yl)acetic acid, a water-miscible anti-solvent, and H$_2$O;
   b) heating the first mixture to a first heating temperature to form a second mixture; wherein said first heating temperature is about 79° C. to about 85° C.;
   c) adding a first additional amount of said water-miscible anti-solvent to said second mixture while maintaining said first heating temperature to form a suspension;
   d) cooling the suspension to a first cooling temperature and thereafter heating to a second heating temperature; wherein said first cooling temperature is about 18° C. to about 22° C., and said second heating temperature is about 69° C. to about 73° C.;
   e) cycling Step d) optionally one or more times, wherein the first cooling temperature at each cycle may be the same or different and the second heating temperature at each cycle may be the same or different; and
   f) cooling said suspension to a final cooling temperature to form said crystalline free-plate habit of L-arginine salt of (R)-2-(7-(4-cyclopentyl-3-(trifluoromethyl)benzyloxy)-1,2,3,4-tetrahydrocyclopenta[b]indol-3-yl) acetic acid; wherein said final cooling temperature is about 18° C. to about 22° C.

2. A method according to claim 1, for preparing a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid that is substantially free of radial clusters or spherulites, said method comprising the steps of:
   a) hydrolyzing a compound of Formula (IIa):

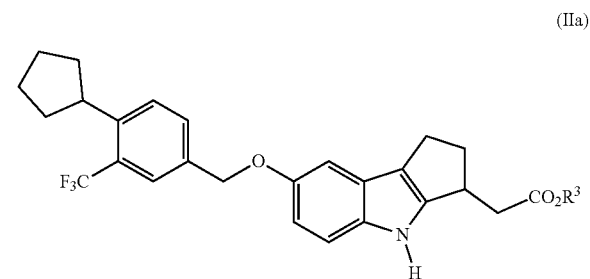

(IIa)

wherein R$^3$ is C$_1$-C$_6$ alkyl; in the presence of a hydrolyzing mixture comprising a lipase and a hydrolyzing-step solvent to form (R)-2-(7-(4-cyclopentyl-3-(trifluoromethyl)benzyloxy)-1,2,3,4-tetrahydrocyclopenta[b]indol-3-yl)acetic acid;
   b) forming a first mixture comprising L-arginine salt of (R)-2-(7-(4-cyclopentyl-3-(trifluoromethyl)benzyloxy)-1,2,3,4-tetrahydrocyclopenta[b]indol-3-yl)acetic acid, a water-miscible anti-solvent, and H$_2$O;
   c) heating the first mixture to a first heating temperature to form a second mixture; wherein said first heating temperature is about 79° C. to about 85° C.;
   d) adding a first additional amount of said water-miscible anti-solvent to said second mixture while maintaining said first heating temperature to form a suspension;
   e) cooling said suspension to a first cooling temperature and thereafter heating to a second heating temperature; wherein said first cooling temperature is about 18° C. to about 22° C., and said second heating temperature is about 69° C. to about 73° C.;
   f) cycling Step e) optionally one or more times, wherein said first cooling temperature at each cycle may be the same or different and said second heating temperature at each cycle may be the same or different; and
   g) cooling said suspension to a final cooling temperature to form said crystalline free-plate habit of L-arginine salt of (R)-2-(7-(4-cyclopentyl-3-(trifluoromethyl)benzyloxy)-1,2,3,4-tetrahydrocyclopenta[b]indol-3-yl) acetic acid; wherein said final cooling temperature is about 18° C. to about 22° C.

3. The method according to claim 2, wherein said hydrolyzing-step solvent comprises acetonitrile.

4. The method according to claim 2, wherein:
said compound of Formula (IIa) is:

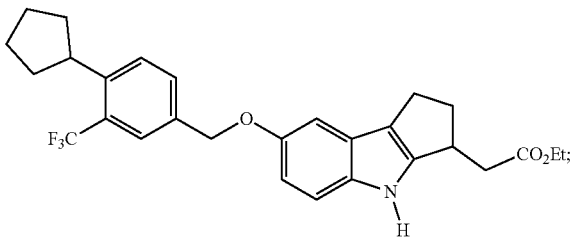 [SMILES: CCOC(=O)CC1CCc2c1[nH]c1ccc(OCc3ccc(C4CCCC4)c(C(F)(F)F)c3)cc21]

said lipase is immobilized *Candida antarctica* lipase B; and
said hydrolyzing-step solvent comprises acetonitrile.

5. The method of claim 2, wherein said hydrolyzing is conducted in the presence of a phosphate buffer at a pH of about 6.9 to about 8.1, wherein said phosphate buffer is a potassium phosphate buffer.

6. The method of claim 2, wherein said hydrolyzing is conducted at a temperature of about 35° C. to about 45° C.

7. The method of claim 2, wherein after said hydrolyzing, said (R)-2-(7-(4-cyclopentyl-3-(trifluoromethyl)benzyloxy)-1,2,3,4-tetrahydrocyclopenta[b]indol-3-yl)acetic acid is present in an amount of at least 40% as determined by HPLC.

8. The method of claim 2, wherein forming said first mixture in Step b) comprises the step of adding L-arginine and H$_2$O, either together or separately in any order, to a salt-forming mixture comprising (R)-2-(7-(4-cyclopentyl-3-(trifluoromethyl)benzyloxy)-1,2,3,4-tetrahydrocyclopenta[b]indol-3-yl)acetic acid and said water-miscible anti-solvent to form said first mixture.

9. The method of claim 2, wherein said water-miscible anti-solvent comprises a solvent selected from the group consisting of: acetonitrile, acetone, tetrahydrofuran, and C$_2$-C$_4$ alkanol.

10. The method of claim 2, wherein said water-miscible anti-solvent comprises 2-propanol.

11. The method of claim 10, wherein prior to adding said L-arginine and H$_2$O, said salt-forming mixture comprises (R)-2-(7-(4-cyclopentyl-3-(trifluoromethyl)benzyloxy)-1,2,3,4-tetrahydro-cyclopenta[b]indol-3-yl)acetic acid and 2-propanol in a weight ratio of about 1.0:6.0 to about 1.0:8.0.

12. The method of claim 8, wherein the molar ratio between (R)-2-(7-(4-cyclopentyl-3-(trifluoromethyl)benzyloxy)-1,2,3,4-tetrahydrocyclopenta[b]indol-3-yl)acetic acid and L-arginine is about 1.0:0.93 to about 1.0:1.01.

13. The method of claim 8, wherein the weight ratio of L-arginine and H$_2$O is about 1.0:1.2 to about 1.0:1.5.

14. The method of claim 8, wherein said salt-forming mixture prior to said adding L-arginine is at a temperature of about 18° C. to about 30° C.

15. The method of claim 10, wherein said salt-forming mixture comprises (R)-2-(7-(4-cyclopentyl-3-(trifluoromethyl)benzyloxy)-1,2,3,4-tetrahydro-cyclopenta[b]indol-3-yl)acetic acid, 2-propanol, and water in a weight ratio of about 1.0:6.0:0.25 to about 1.0:8.0:0.7.

16. The method of claim 8, wherein said salt-forming mixture during said adding L-arginine is at a temperature of about 18° C. to about 30° C.

17. The method of claim 8, wherein the weight ratio of L-arginine salt of (R)-2-(7-(4-cyclopentyl-3-(trifluoromethyl)benzyloxy)-1,2,3,4-tetrahydrocyclo-penta[b]indol-3-yl)acetic acid to said first additional amount of 2-propanol is about 1.00:5.95 to about 1.00:6.25.

18. The method of claim 2, wherein said first additional amount of said water-miscible anti-solvent is added during a first time point and a second time point.

19. The method of claim 18, wherein about 8% to about 12% of said first additional amount of said water-miscible anti-solvent is added at said first time point.

20. The method of claim 18, wherein said first additional amount of said water-miscible anti-solvent is added at said first time point to form a cloudy mixture.

21. The method of claim 18, wherein prior to said second time point, a seed crystal of L-arginine salt of (R)-2-(7-(4-cyclopentyl-3-(trifluoromethyl)benzyloxy)-1,2,3,4-tetrahydrocyclopenta[b]indol-3-yl)acetic acid is optionally added.

22. The method of claim 18, wherein said first additional amount of said water-miscible anti-solvent is added at said second time point at a rate to complete the addition in about 1.00 hour or greater.

23. The method of claim 2, wherein cooling said suspension to said first cooling temperature in Step e) is conducted at a rate of about 9° C./hour to about 11° C./hour.

24. The method of claim 2, wherein said cycling in Step f) comprises said cycling Step e) two times.

25. The method of claim 24, wherein said cycling Step e) two times comprises cooling the suspension to a first cycling cooling temperature, heating the suspension to a first cycling heating temperature, cooling the suspension to a second cycling cooling temperature, and heating the suspension to a second cycling heating temperature.

26. The method of claim 25, wherein said first cycling cooling temperature is about 16° C. to about 26° C., said first heating cycling temperature is about 55° C. to about 65° C., said second cycling cooling temperature is about 26° C. to about 36° C., and said second cycling heating temperature is about 45° C. to about 55° C.

27. The method of claim 2, wherein said cycling in Step f) comprises said cycling Step e) three times.

28. The method of claim 27, wherein said cycling Step e) three times comprises: cooling the suspension to a first cycling cooling temperature, heating the suspension to a first cycling heating temperature, cooling the suspension to a second cycling cooling temperature, heating the suspension to a second cycling heating temperature, cooling the suspension to a third cycling cooling temperature, and heating the suspension to a third cycling heating temperature.

29. The method of claim 28, wherein said first cycling cooling temperature is about 16° C. to about 26° C., said first heating cycling temperature is about 66° C. to about 76° C., said second cycling cooling temperature is about 16° C. to about 26° C., said second cycling heating temperature is about 55° C. to about 65° C., said third cycling cooling temperature is about 26° C. to about 36° C., and said third cycling heating temperature is about 45° C. to about 55° C.

30. The method of claim 1, wherein said first additional amount of said water-miscible anti-solvent is added during a first time point and a second time point.

31. The method of claim 30, wherein about 8% to about 12% of said first additional amount of said water-miscible anti-solvent is added at said first time point.

32. The method of claim 30, wherein said first additional amount of said water-miscible anti-solvent is added at said first time point to form a cloudy mixture.

33. The method of claim 30, wherein prior to said second time point, a seed crystal of L-arginine salt of (R)-2-(7-(4- cyclopentyl-3-(trifluoromethyl)benzyloxy)-1,2,3,4-tetrahydrocyclopenta[b]indol-3-yl)acetic acid is optionally added.

34. The method of claim 30, wherein said first additional amount of said water-miscible anti-solvent is added at said second time point at a rate to complete the addition in about 1.00 hour or greater.

35. The method of claim 1, wherein cooling said suspension to said first cooling temperature in Step d) is conducted at a rate of about 9° C./hour to about 11° C./hour.

36. The method of claim 1, wherein said cycling in Step e) comprises said cycling Step d) two times.

37. The method of claim 36, wherein said cycling Step d) two times comprises cooling the suspension to a first cycling cooling temperature, heating the suspension to a first cycling heating temperature, cooling the suspension to a second cycling cooling temperature, and heating the suspension to a second cycling heating temperature.

38. The method of claim 37, wherein said first cycling cooling temperature is about 16° C. to about 26° C., said first heating cycling temperature is about 55° C. to about 65° C., said second cycling cooling temperature is about 26° C. to about 36° C., and said second cycling heating temperature is about 45° C. to about 55° C.

39. The method of claim 1, wherein said cycling in Step e) comprises said cycling Step d) three times.

40. The method of claim 39, wherein said cycling Step d) three times comprises: cooling the suspension to a first cycling cooling temperature, heating the suspension to a first cycling heating temperature, cooling the suspension to a second cycling cooling temperature, heating the suspension to a second cycling heating temperature, cooling the suspension to a third cycling cooling temperature, and heating the suspension to a third cycling heating temperature.

* * * * *